United States Patent
Bronkhof et al.

(10) Patent No.: US 10,072,267 B2
(45) Date of Patent: Sep. 11, 2018

(54) FUNGAL HIGH-LEVEL PROTEIN PRODUCTION SYSTEM

(71) Applicant: DANISCO US INC., Palo Alto, CA (US)

(72) Inventors: Jurian Alexander Bronkhof, Apeldoom (NL); Jean-Paul Meijnen, Rhenen (NL); Carola Bianca Michielse, Kranenburg (DE); Ismail Atalay Van Der Burgt, Wageningen (NL); Jacob Visser, Wageningen (NL); Johannes Heinrich Visser, Wijchen (NL)

(73) Assignee: DANISCO US INC CA (US)

(*) Notice: Subject to any disclaimer, the term of this patent is extended or adjusted under 35 U.S.C. 154(b) by 0 days.

(21) Appl. No.: 15/439,226

(22) Filed: Feb. 22, 2017

(65) Prior Publication Data

US 2017/0240909 A1     Aug. 24, 2017

Related U.S. Application Data

(60) Provisional application No. 62/298,351, filed on Feb. 22, 2016.

(51) Int. Cl.
| | |
|---|---|
| *C12N 15/80* | (2006.01) |
| *C12N 9/24* | (2006.01) |
| *C12N 9/34* | (2006.01) |
| *C12N 9/38* | (2006.01) |
| *C07K 14/37* | (2006.01) |
| *C12P 21/02* | (2006.01) |

(52) U.S. Cl.
CPC ............. *C12N 15/80* (2013.01); *C07K 14/37* (2013.01); *C12N 9/248* (2013.01); *C12N 9/2428* (2013.01); *C12N 9/2468* (2013.01); *C12P 21/02* (2013.01); *C12Y 302/01003* (2013.01); *C12Y 302/01015* (2013.01); *C12Y 302/01037* (2013.01)

(58) Field of Classification Search
None
See application file for complete search history.

(56) References Cited

U.S. PATENT DOCUMENTS

| | | | |
|---|---|---|---|
| 6,015,707 A | 1/2000 | Emalfarb et al. | |
| 6,573,086 B1 | 6/2003 | Emalfrab et al. | |
| 2014/0295504 A1 | 10/2014 | Dufresne et al. | |

FOREIGN PATENT DOCUMENTS

| | | |
|---|---|---|
| EP | 3000880 A1 | 3/2016 |
| JP | 2003180365 A | 7/2003 |
| KR | 20110021522 A | 3/2011 |
| WO | 2008083271 A2 | 7/2008 |
| WO | 2010107303 A2 | 9/2010 |
| WO | 2014081700 A1 | 5/2014 |

OTHER PUBLICATIONS

Houghten et al. (Vaccines, 1986, Edited by Fred Brown: Cold Spring Harbor Laboratory).*
Pranavas et al SUMO Protocols, Edited by Helle D.Ulrich, Human Press 2009, Chapter 20, pp. 303-317.*
Chymkowitch et al., SUMO-Regulated Transcription: Challenging the Dogma, Bioessays Journal, vol. 37 (2015), pp. 1095-1105.
Hirohama et al., Spectomycin B1 as a Novel SUMOylation Inhibitor That Directly Binds to SUMO E2, ACS Chem. Biol., vol. 8 (2013), pp. 2635-2642.
Muller et al., SUMO, Ubiquitin's Mysterious Cousin, Nature Reviews, vol. 2 (2001), pp. 202-210.
Visser et al., Development of a Mature Fungal Technology and Production Platform for Industrial Enzymes Based on a Myceliophthora Thermophila Isolate, Previously Known as Chrysosporium Lucknowense C1, Industrial Biotechnology, vol. 7, No. 3 (2011), pp. 214-223.
Wang et al., Human SUMO Fusion systems enhance protein expression and solubility, protein EXPR. PURIF., vol. 73, No. 2 (2010), pp. 1-2.
Wilkinson et al., Mechanisms, Regulation and Consequences of Protein SUMOylation, Biochem. J., vol. 428 (2010), pp. 133-145.
Wong et al., SUMOylation in Aspergillus Nidulans: SUMO Inactivation, Overexpression and Live-Cell Imaging, Fungal Genet. Biol., vol. 45, No. 5 (2008), pp. 728-737.
PCT International Application Written Opinion for Application No. PCT/US17/018901, Sonnerat Isabelle, Authorized Officer; ISA/EP, Aug. 31, 2017.
Zuo et al., Enhanced Expression and Purification of Membrane Proteins by SUMO Fusion in *Escherichia coli*, Journal of Structural and Functional Genomics, vol. 6 (2005), pp. 103-111.

* cited by examiner

*Primary Examiner* — Padmavathi Baskar

(57) ABSTRACT

Provided are cells having an increased protein production characterized in that said cell comprises modified SUMOylation, a process for producing such a cell or expression system and the use of such a cell in producing a protein of interest.

6 Claims, 6 Drawing Sheets

Specification includes a Sequence Listing.

Total protein  15,6  35,5 g/L

FIG. 8

```
<MultipleProteinSequenceAlignment (5x158) >
       .  001     .  002     .  003     .  004     .  005
-MSLCQNrlqeerkqwrkdhpfgfYARPQKNAQGVLDLKVWECGIPGKEKTMW Mycthe
-MALCQNrlqeerkqwrkdhpfgfYARPQKNQQGVLDLKIWECGIPGKEKTIW Neucra
-MSLCLNrlteerkqwrkdhpfafYAKPHRTAQGVLDMKRWECGIPGKKGTIW Aspnid
MSSLCLQrlqeerkkwrkdhpfgfYAKPVKKADGSMDLQKWEAGIPGKEGTNW Saccer
MSNLAQArlheerkqwrkdhpfgfYARPTKAADGTLNIMSWEVGIPKAGTDW Cryneo
 ..*:...**.****:*******:***:*.:...:*.::::..**.*****..*.*
       .  001     .  002     .  003     .  004     .  005
            RLQEERKQWRKDHPFGF                          motif1
            RLqEERKqWRkDHPFgF                          consensus1

.  006     .  007     .  008     .  009     .  010     .
EGGLFKLVVTFPDEYPTkppkckftpplfhpnvypsgtvclsilNEEEAWKPA Mycthe
EGGLFKLTVTFPDEYPTkppkckfvpplfhpnvypsgtvclsilNEEEAWKPA Neucra
EGGLFKLDVTFPDEYPTkppkckfvpalfhpnvypsgtvclsilNEDEAWKPA Aspnid
AGGVYPITVEYPNEYPSkppkvkfpagfyhpnvypsgticlsilNEDQDWRPA Saccer
EGGIYVVKMNFPDEFPTkppkckfdpplfhpnvypsgticlsilDEEKSWKPS Cryneo
 **::.:.:.:*:*:*;**** **..::**********:*****:*::.*:*:
  .  006     .  007     .  008     .  009     .  010     .
            KPPKCKFTPPLFHPNVYPSGTVCLSIL        motif2
            KPPKCkFvpplfHPNVYPSGTvCLSIL        consensus2

011      .  012     .  013     .  014     .  015     .  0
ITIKQILLGVQDLLNDPNPESPAQAEAYNMYKKDRVQYERRIRQIVRENAAP Mycthe
ITMKQILLGIQDLLNDPNPESPAQAEAYNLFKKDRQEYERRIKRVVRENAAP Neucra
ITIKQILLGIQDLLDDPNPESPAQAEAYNMYKKDRAAYEKRVKQVVKENPAL Aspnid
ITLKQIVLGVQDLLDSPNPNSPAQEPAWRSFSRNKAEYDKKVLLQAKQYSK- Saccer
ITVKQICLGIQDLLEHANVNDPAQVEAYHMFKNDRTSYDKRIRQQAVERRPK Cryneo
 **:***.**:****:,. * ::***,,*::,::::,..*::::...:.:,...
 011      .  012     .  013     .  014     .  015     .  0
```

FUNGAL HIGH-LEVEL PROTEIN PRODUCTION SYSTEM

CROSS REFERENCE TO RELATED APPLICATIONS

This application claims the benefit of U.S. Provisional Application No. 62/298,351, filed on Feb. 22, 2016, which is herein incorporated by reference in its entirety.

FIELD OF THE INVENTION

The present invention is in the area of protein production systems, more in particular to fungal production systems capable of producing high-levels of protein. The invention is based on the finding that modification of SUMOylation results in an increase in protein production. This invention renders these mutant fungal systems suitable for protein production in industry.

SEQUENCE LISTING

The content of the electronically submitted sequence listing in ASCII text filed herewith (File Name: NB36013WOPCT_SEQLIST_ST25.txt; Size: 143,201 bytes; and date of creation Feb. 22, 2017) forms part of the specification and is incorporated herein by reference in its entirety.

BACKGROUND

The production of enzymes used in industrial applications is a growing market that is driven by the need to move from a fossil-based to a bio-based economy. The increasing demand for these enzymes makes the cost of enzyme production an important expense. The reduction of the cost of enzyme production calls for the exploration of novel enzymes, as well as reliable methods for high-yield production processes. In order to set up cost-effective enzyme production processes, high-level protein production and secretion are key requirements.

Fungi have been used as hosts for the production of a variety of enzymes. Strains belonging to genera, but not limited to *Chrysosporium, Thielavia, Talaromyces, Thermomyces, Thermoascus, Neurospora, Aureobasidium, Filivasidium, Piromyces, Corynascus, Cryptococcus, Acremonium, Tolypocladium, Scytalidium, Schizophyllum, Sporotrichum, Penicillium, Gibberella, Myceliophthora, Mucor, Aspergillus, Fusarium, Humicola* and *Trichoderma* plus anamorphs and teleomorphs thereof have been applied in the industrial production of a wide range of enzymes. Strains have been developed that secrete up to 100 g/L or more protein in the fermentation broth, see for instance Visser et al., (Development of a mature fungal technology and production platform for industrial enzymes based on a *Myceliophthora thermophila* isolate, previously known as *Chrysosporium lucknowense* C1, Industrial Biotechnology, 2011. 7(3): p. 214-223) and European patent application no. 2408910. The protein-secreting capacity of these fungi make them attractive hosts for the targeted production of specific enzymes or enzyme mixes.

SUMMARY OF THE INVENTION

Provided herein are modified cells having increased protein production. Provided are modified cells which have been modified to result in altered SUMOylation. The increase in protein production may be an increase of overall protein production of at least 1.1 fold as compared to the total protein production of the parental cell that lacks the modification of SUMOylation. The increase in protein production may be an increase of production of a protein of interest at least 1.1 fold as compared to the production of said protein by the parental cell that lacks the modification of SUMOylation.

Provided herein are modified cells wherein SUMOylation has been modified by genetic modification of at least one gene encoding an endogenous protein of the SUMOylation machinery. The genetic modification may be a point mutation, insertion and/or deletion. The genetic modification may be a targeted modification. The genetic modification may be a modification of an expression regulating sequence or the coding sequence. In embodiments, SUMOylation is modified by reducing Ubc9 production and/or activity. In embodiments, Ubc9 is modified by a gene disruption located in the coding sequence or in the promoter sequence of the ubc9 gene. In embodiments, the ubc9 gene has a wild type counterpart that has at least 50% sequence identity to SEQ ID NO: 1 [*M. thermophila*]. In embodiments, the ubc 9 gene has a wild-type counterpart encoding a protein comprising PFAM domain PF00179. In embodiments, the ubc 9 gene has a wild-type counterpart encoding a protein comprising a sequence that has at least 75% identity to one or more of the sequence motifs of SEQ ID NO: 42 or 43.

Modified cells provided herein may be fungal cells, such as filamentous fungal cells. Modified cells may be fungal cells of the genus selected form the group consisting of *Chrysosporium, Thielavia, Neurospora, Aureobasidium, Filibasidium, Piromyces, Corynascus, Cryptococcus, Acremonium, Tolypocladium, Scytalidium, Schizophyllum, Sporotrichum, Penicillium, Gibberella, Myceliophthora, Mucor, Aspergillus, Fusarium, Humicola, Trichoderma, Talaromyces* and *Rasamsonia*. In embodiments, the cell is or is derived from *Myceliophthora thermophila*. In embodiments, the cell is or is derived from a strain selected from the group consisting of C1 (deposited with the International Depository of the All Russian Collection of micro-organisms of the Russian Academy of Sciences under accession number VKM F-3500D), UV18-25 (deposited at VKM under accession number VKM F-3631 D), UV18#100f (deposited at CBS under accession number CBS122188), W1L (deposited at CBS under accession number CBS122189) and W1L#100L (strain deposited at CBS under accession number CBS122190). In embodiments, the cell is a *Myceliophthora thermophila* cell. In embodiments, the cell is not derived from C1 or is not derived from UV18-25 or is not derived from UV18#100f or is not derived from W1L or is not derived from W1L#100L. In embodiments, the cell is not derived from W1L#100.1Δalp1Δchi1Δpyr5. In embodiments, the cell is or is derived from *Trichoderma*, and in embodiments the cell is or is derived from *Trichoderma reesei*. In embodiments, the cell is or is derived from *Aspergillus*, and in embodiments, the cell is or is derived from *Aspergillus niger*.

Modified cells provided herein may further comprise an exogenous expression construct that encodes at least one protein of interest. In embodiments, the protein of interest is a heterologous protein. In embodiments, the protein of interest is an acetyl esterase, aminopeptidase, amylase, arabinase, arabinofuranosidase, carboxypeptidase, catalase, cellulase, chitinase, chymosin, cutinase, deoxyribonuclease, epimerase, esterase, α-galactosidase, β-galactosidase, α-glucanase, glucan lysase, endo-β-glucanase, glucoamylase, glucose oxidase, α-glucosidase, β-glucosidase, glucuronidase, hemicellulase, hexose oxidase, hydrolase, invertase, isomerase, laccase, lipase, lyase, mannosidase, oxidase, oxidoreductase, pectate lyase, pectin acetyl esterase, pectin depolymerase, pectin methyl esterase, pectinolytic enzyme, peroxidase, phenoloxidase, phytase, polygalacturonase, protease, rhamno-galacturonase, ribonuclease, thaumatin, transferase, transport protein, transglutaminase, xylanase, hexose oxidase, a functional fragment thereof, or a mixture of one or more thereof. In embodiments, the protein of interest is a peptide hormone, growth factor, clotting factor, chemokine, cytokine, lymphokine, antibody, receptor, adhesion molecule, microbial antigen, a functional fragment thereof, or a mixture of one or more thereof. In embodiments, the protein is an enzyme for degrading lignocellulosic material or an active fragment thereof. Accordingly, in some embodiments, the protein of interest is not an enzyme for degrading lignocellulosic material or an active fragment thereof. In embodiments, the protein of interest is a cellobiohydrolase, xylanase, endoglucanase, β-glucosidase, β-xylosidase, an accessory enzyme, glucoamylase, alpha-amylase, alpha-glucosidase, phytase, protease, aminopeptidase, mannanase, laccase, catalase, glucose or hexose oxidase, oligosaccharide oxidase, lipase, or a mixture of one or more thereof.

Also provided herein are processes for producing a modified cell having increased protein production as compared to the parent cell that has not been modified, comprising introducing at least one genetic modification in a gene encoding a SUMOylation protein. In embodiments, the genetic modification is a point mutation, insertion and/or deletion. In embodiments, the genetic modification is targeted. In embodiments, the resulting genetic modification is a modification of an expression regulating sequence or the coding sequence. In embodiments, the expression regulating sequence is a promoter sequence. In embodiments, the genetic modification results in a reduced Ubc9 production and/or activity. In embodiments, the genetic modification encompasses a gene disruption located in the promoter sequence of the ubc9 gene. In embodiments, the ubc9 gene has a wild type counterpart that has at least 50%, at least 60%, at least 70%, at least 80%, at least 85%, at least 80%, at least 95%, at least 99%, or 100% sequence identity to the promoter region or the coding region or both of SEQ ID NO: 1 [ubc9 of M. thermophila]. In embodiments, the ubc9 gene has a wild type counterpart that comprises a sequence with at least 50%, at least 60%, at least 70%, at least 80%, at least 85%, at least 80%, at least 95%, at least 99%, or 100% sequence identity to SEQ ID NO: 47 or 48. In embodiments, the ubc 9 gene has a wild type counterpart that comprises a sequence with at least 50%, at least 60%, at least 70%, at least 80%, at least 85%, at least 80%, at least 95%, at least 99%, or 100% sequence identity to the promoter or coding portion of SEQ ID NO: 45.

Also provided herein are processes for producing an expression system comprising the step of transducing a modified cell provided herein, or a modified cell obtained by a process provided herein. In embodiments, the cell is transduced with at least one exogenous expression construct encoding at least one protein of interest. In embodiments, the at least one protein of interest is heterologous to the cell.

Also provided is a process for producing a protein of interest, comprising the step of culturing a modified cell provided herein, or a modified cell or expression system provided herein or obtained by a process provided herein.

Provided herein is a cell broth produced by a modified cell disclosed herein as well as a composition comprising a modified cell disclosed herein or a cell broth. Such a composition may optionally further comprise a substrate comprising lignocellulosic material.

Also provided herein is use of a modified cell disclosed herein in a process for producing at least one protein of interest. In embodiments, the protein of interest is encoded by a heterologous expression construct. In embodiments, the protein of interest is heterologous to the cell.

BRIEF DESCRIPTION OF THE DRAWINGS

FIG. 8. Multiple sequence alignment of Ubc9 protein sequences from M. thermophila ("Mycthe"; SEQ ID NO: 2); N. crassa ("Neurcra"; SEQ ID NO: 9); A. nidulans ("Aspnid"; SEQ ID NO: 11); S. cerevisiae ("Saccer"; SEQ ID NO: 15); C. neoformans ("Cryneo"; SEQ ID NO: 13); and conserved motifs (motif 1/consensus 1: SEQ ID NO: 42; motif 2: SEQ ID NO: 43; consensus 2: SEQ ID NO: 44).

Figure 1:
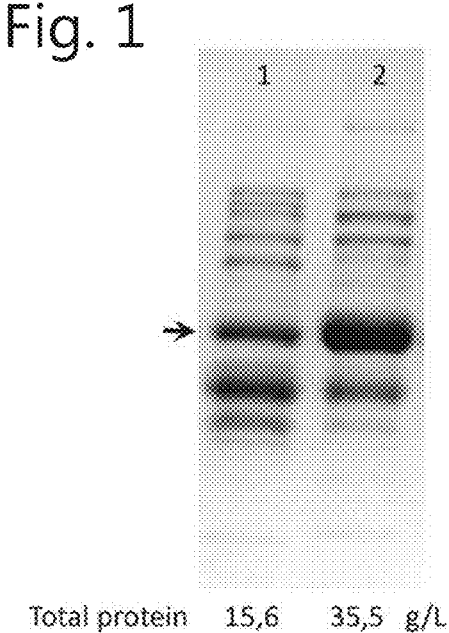
FIG. 1. SDS-PAGE analysis of end-of-fermentation broth of:
W1L#100.1Δalp1Δchi1Δpyr5[eg2/pyr5] (lane 1); and
W1L#100.1Δalp1Δchi1Δpyr5[eg2/pyr5]ubc9- (lane 2).
Equal loading of protein content (~1 g/L) per lane. Arrow head indicates Eg2 protein.

Table 4 provides an overview of SEQ ID Nos 1-7.

DETAILED DESCRIPTION

As used herein, unless otherwise specified, reference to a percent (%) identity refers to an evaluation of homology which is performed using: 1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schaffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402); 2) a BLAST 2 alignment (using the parameters described below); 3) PSI-BLAST with the standard default parameters (Position-Specific Iterated BLAST; and/or 4) CAZy homology determined using standard default parameters from the Carbohydrate Active EnZymes database (Coutinho, P. M. & Henrissat, B. (1999) Carbohydrate-active enzymes: an integrated database approach. In "Recent Advances in Carbohydrate Bioengineering", H. J. Gilbert, G. Davies, B. Henrissat and B. Svensson eds., The Royal Society of Chemistry, Cambridge, pp. 3-12) and/or applying a similar strategy using databases such as the Foly database (website: foly.esil.univ-mrs.fr) and the PeroxiBase (website: peroxibase.isb-sib.ch).

It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues or variants. The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174:247-250. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

Unless otherwise indicated herein, identity with a given SEQ ID NO means identity based on the full and contiguous length of said sequence (i.e. over its whole length or as a whole).

As used herein, the term "contiguous" or "consecutive", with regard to nucleic acid or amino acid sequences described herein, means to be connected in an unbroken sequence. For example, for a first sequence to comprise 30 contiguous (or consecutive) amino acids of a second sequence, means that the first sequence includes an unbroken sequence of 30 amino acid residues that is 100% identical to an unbroken sequence of 30 amino acid residues in the second sequence. Similarly, for a first sequence to have "100% identity" or being "100% identical" with a second sequence means that the first sequence exactly matches the second sequence with no gaps between nucleotides or amino acids.

A nucleic acid molecule encoding a protein as disclosed herein refers to the nucleotide sequence of the nucleic acid strand that encodes the protein. It will be appreciated that a double stranded DNA which encodes a given amino acid sequence comprises a single strand DNA and its complementary strand having a sequence that is a complement to the single strand DNA. As such, nucleic acid molecules can be either double-stranded or single-stranded, and include those complementary strands. Methods to deduce a complementary sequence are known to those skilled in the art. It should be noted that since nucleic acid sequencing technologies are not entirely error-free, the sequences presented herein, at best, represent apparent sequences of the proteins disclosed herein.

As used herein, reference to hybridization conditions refers to standard hybridization conditions under which nucleic acid molecules are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., (see specifically, pages 9.31-9.62). In addition, formulae to calculate the appropriate hybridization and wash conditions to achieve hybridization permitting varying degrees of mismatch of nucleotides are disclosed, for example, in Meinkoth et al., 1984, *Anal. Biochem.* 138, 267-284; Meinkoth et al., ibid.

More particularly, moderate stringency hybridization and washing conditions, as referred to herein, refer to conditions which permit isolation of nucleic acid molecules having at least about 70% nucleotide sequence identity with the nucleic acid molecule being used to probe in the hybridization reaction (i.e., conditions permitting about 30% or less mismatch of nucleotides). High stringency hybridization and washing conditions, as referred to herein, refer to conditions which permit isolation of nucleic acid molecules having at least about 80% nucleotide sequence identity with the nucleic acid molecule being used to probe in the hybridization reaction (i.e., conditions permitting about 20% or less mismatch of nucleotides). Very high stringency hybridization and washing conditions, as referred to herein, refer to conditions which permit isolation of nucleic acid molecules having at least about 90% nucleotide sequence identity with the nucleic acid molecule being used to probe in the hybridization reaction (i.e., conditions permitting about 10% or less mismatch of nucleotides). As discussed above, one of skill in the art can use the formulae in Meinkoth et al., ibid. to calculate the appropriate hybridization and wash conditions to achieve these particular levels of nucleotide mismatch. Such conditions will vary, depending on whether DNA:RNA or DNA:DNA hybrids are being formed. Calculated melting temperatures for DNA:DNA hybrids are 10° C. less than for DNA:RNA hybrids. Preferably, stringent hybridization conditions for DNA:DNA hybrids include hybridization at an ionic strength of 6×SSC (0.9 M Na$^+$) at a temperature of between about 20° C. and about 35° C. (lower stringency), more preferably, between about 28° C. and about 40° C. (more stringent), and even more preferably, between about 35° C. and about 45° C. (even more stringent), with appropriate wash conditions. Preferably, stringent hybridization conditions for DNA:RNA hybrids include hybridization at an ionic strength of 6×SSC (0.9 M Na$^+$) at a temperature of between about 30° C. and about 45° C., more preferably, between about 38° C. and about 50° C., and even more preferably, between about 45° C. and about 55° C., with similarly stringent wash conditions. These values are based on calculations of a melting temperature (Tm) for molecules larger than about 100 nucleotides, 0% formamide and a G+C content of about 40%. Alternatively, Tm can be calculated empirically as set forth in Sambrook et al., supra, pages 9.31 to 9.62. In general, the wash conditions should be as stringent as possible, and should be appropriate for the chosen hybridization conditions. For example, hybridization conditions can include a combination of salt and temperature conditions that are approximately 20-25° C. below the calculated Tm of a particular hybrid, and wash conditions typically include a combination of salt and temperature conditions that are approximately 12-20° C. below the calculated Tm of the particular hybrid.

One example of hybridization conditions suitable for use with DNA:DNA hybrids includes a 2-24 hour hybridization in 6×SSC (50% formamide) at about 42° C., followed by washing steps that include one or more washes at room temperature in about 2×SSC, followed by additional washes at higher temperatures and lower ionic strength (e.g., at least one wash as about 37° C. in about 0.1×-0.5×SSC, followed by at least one wash at about 68° C. in about 0.1×-0.5×SSC).

Reference to a gene includes all nucleotide sequences related to a natural (i.e. wild-type) gene, such as regulatory regions that control production of the protein encoded by that gene (such as, but not limited to, transcription, translation or post-translation control regions) as well as the coding region itself. Genes can include or exclude one or more introns or any portions thereof or any other sequences which are not included in the cDNA for that protein. The phrases "nucleic acid molecule" and "gene" can be used interchangeably when the nucleic acid molecule comprises a gene as described above.

Modified genes include natural genes modified by substitution, insertion, and/or deletion of single or multiple nucleotide sequences, which can occur within the coding sequence including exons of regions encoding a polypeptide, or in flanking regions, such as regulatory regions typically upstream (e.g., promoters, enhancers, and related sequences), downstream (e.g., transcriptional termination, and poly(A) signals), or internal regions (e.g., introns) that affect the transcription, translation, and/or activation of a polypeptide or regulatory molecule of interest. Activation of a polypeptide, for example, may require removal of one or more N-terminal, C-terminal, or internal polypeptide regions, and/or post-translational modification of specific amino acid residues, such as by glycosylation, amidation, etc., that may alter the targeting, degradation, catalytic activity, of an enzyme.

A nucleic acid molecule as disclosed herein can be produced using recombinant DNA technology (e.g., polymerase chain reaction (PCR) amplification, cloning, etc.) or chemical synthesis. A nucleic acid modification can be produced using a number of methods known to those skilled in the art (see, for example, Sambrook et al.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Another method for modifying a recombinant nucleic acid molecule encoding a protein is gene shuffling (i.e., molecular breeding) (See, for example, U.S. Pat. No. 5,605,793 to Stemmer, incorporated herein by reference; Minshull and Stemmer; 1999, *Curr. Opin. Chem. Biol.* 3:284-290; Stemmer, 1994, *P.N.A.S. USA* 91:10747-10751). This technique can be used to efficiently introduce multiple simultaneous changes in the protein.

A nucleic acid molecule as disclosed herein may be a recombinant nucleic acid molecule which comprises the nucleic acid molecule described above which is operatively linked to at least one expression control sequence. More particularly, a recombinant nucleic acid molecule typically comprises a recombinant vector and any one or more of the nucleic acid molecules as described herein. As used herein, a recombinant vector is an engineered (i.e., artificially produced) nucleic acid molecule that is used as a tool for manipulating a nucleotide sequence of choice and/or for introducing such a nucleotide sequence into a host cell. The recombinant vector is therefore suitable for use in cloning, sequencing, and/or otherwise manipulating the nucleotide sequence of choice, such as by expressing and/or delivering the nucleotide sequence of choice into a host cell to form a recombinant cell. Such a vector typically contains nucleotide sequences that are not naturally found adjacent to nucleotide sequence to be cloned or delivered, although the vector can also contain regulatory nucleotide sequences (e.g., promoters, untranslated regions) which are naturally found adjacent to nucleotide sequences disclosed herein or which are useful for expression of the nucleic acid molecules disclosed herein (discussed in detail below). The vector can be either RNA or DNA, either prokaryotic or eukaryotic, and typically is a plasmid. The vector can be maintained as an extrachromosomal element (e.g., a plasmid) or it can be integrated into the chromosome of a recombinant host cell, although it is preferred if the vector remains separate from the genome. The entire vector can remain in place within a host cell, or under certain conditions, the plasmid DNA can be deleted, leaving behind the nucleic acid molecule disclosed herein. An integrated nucleic acid molecule can be under chromosomal promoter control, under native or plasmid promoter control, or under a combination of several promoter controls. Single or multiple copies of the nucleic acid molecule can be integrated into the chromosome. A recombinant vector disclosed herein can contain at least one selectable marker.

A recombinant vector used in a recombinant nucleic acid molecule disclosed herein may be an expression vector. As used herein, the phrase "expression vector" is used to refer to a vector that is suitable for production of an encoded product (e.g., a protein of interest, such as an enzyme as disclosed herein). A nucleotide sequence encoding the product to be produced may be inserted into a recombinant vector to produce a recombinant nucleic acid molecule. The nucleotide sequence encoding the protein to be produced is inserted into the vector in a manner that operatively links the nucleotide sequence to regulatory sequences in the vector, which enable the transcription and translation of the nucleotide sequence within the recombinant host cell. Typically, a recombinant nucleic acid molecule includes at least one nucleic acid molecule as disclosed herein operatively linked to one or more expression control sequences (e.g., transcription control sequences or translation control sequences). As used herein, the phrase "recombinant molecule" or "recombinant nucleic acid molecule" primarily refers to a nucleic acid molecule or nucleotide sequence operatively linked to a transcription control sequence, but can be used interchangeably with the phrase "nucleic acid molecule", when such nucleic acid molecule is a recombinant molecule as discussed herein. As used herein, the phrase "operatively linked" refers to linking a nucleic acid molecule to an expression control sequence in a manner such that the molecule can be expressed when transfected (i.e., transformed, transduced, transfected, conjugated or conduced) into a host cell. Transcription control sequences are sequences that control the initiation, elongation, or termination of transcription. Particularly important transcription control sequences are those that control transcription initiation, such as promoter, enhancer, operator and repressor sequences. Suitable transcription control sequences include any transcription control sequence that can function in a host cell or organism into which the recombinant nucleic acid molecule is to be introduced. Transcription control sequences may also include any combination of one or more of any of the foregoing.

Recombinant nucleic acid molecules can also contain additional regulatory sequences, such as translation regulatory sequences, origins of replication, and other regulatory sequences that are compatible with the recombinant cell. A recombinant molecule, including those that are integrated into the host cell chromosome, preferably also contains secretory signals (i.e., signal segment nucleotide sequences) to enable an expressed protein to be secreted from the cell that produces the protein. Suitable signal segments include a signal segment that is naturally associated with the protein to be expressed or any heterologous signal segment capable of directing the secretion of the protein as disclosed herein. A recombinant molecule may comprise a leader sequence to enable an expressed protein to be delivered to and inserted into the membrane of a host cell. Suitable leader sequences include a leader sequence that is naturally associated with the protein, or any heterologous leader sequence capable of directing the delivery and insertion of the protein to the membrane of a cell.

The term "transfection" is generally used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells or plants and describes an inherited change due to the acquisition of exogenous nucleic acids by the microorganism that is essentially synonymous with the term "transfection." Transfection techniques include, but are not limited to, transformation, particle bombardment, electroporation, microinjection, lipofection, adsorption, infection and protoplast fusion.

The term "co-transfection" refers to the simultaneous transfection with two separate nucleic acid molecules. For instance, co-transfection may refer to the simultaneous transfection with one nucleic acid molecule comprising a particular gene, and another nucleic acid molecule comprising a particular marker-gene.

A transgene is understood herein as a gene or modified gene that has been introduced in a cell preferably via recombinant technologies known to the skilled person. The transgene may be either homologous, i.e. normally occurring in the cell, or heterologous, i.e. not normally occurring in the cell. Preferably, the transgene encodes a protein of interest as part of an expression construct and is or is to be transduced in a cell or host cell for the recombinant production of said protein of interest. A transgene may encode a heterologous or a homologous protein. It will be appreciated that a transgene encoding a homologous protein as part of an expression construct that does not normally occur in the cell (eg. comprising a different promoter than that normally associated with the protein coding sequence) is a heterologous transgene.

A reporter transgene or marker gene is to be understood herein as a transgene encoding an indicator protein, i.e. a protein to be detected as indicator for instance for protein expression levels.

A heterologous sequence is to be understood herein as a sequence at a particular position that does not occur at said position in nature. In other words, a specific nucleic acid sequence comprising a heterologous sequence is a nucleic acid sequence that does not normally occur in nature but is introduced therein via random or targeted genetic modification.

A heterologous protein is understood herein as a protein which is not naturally produced by a particular cell for which the protein is indicated as being heterologous.

A homologous protein is understood herein as a protein that is naturally produced by a particular cell for which the protein is indicated as being homologous. A homologous protein may be either an endogenous protein of a cell or exogenous protein, i.e. being recombinantly produced by a cell in case the cell has been transduced with an expression vector encoding the homologous protein.

It will be appreciated that "engineered" may be used herein to refer to artificially produced cells (eg. genetically modified cells) or nucleic acid or protein sequences.

The word "approximately" or "about" when used in association with a numerical value (approximately 10, about 10) preferably means that the value may be the given value of more or less 10% of the value.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one".

All patent and literature references cited in the present specification are hereby incorporated by reference in their entirety.

A microbial production system able to produce and secrete high amounts of a specific enzyme, particularly without the presence of high levels of other proteins, including proteins which have a negative impact on the activity of the desired protein, would have utility for both research and industrial applications. It may enable simplified screening of hosts functionally expressing a desired enzyme. It may furthermore enable production of relatively pure enzyme. It may also enable simplified large scale purification of the desired enzyme. These advantages would greatly contribute to e.g. easy generation of artificial enzyme mixes tailored for different applications, e.g. for, but not limited to plant biomass hydrolysis (biofuels and chemicals), textile finishing, applications in paper and pulp, and feed and food industry. Relatively pure enzymes, produced using the methods described, are also enabling the design of efficient processes for, but not limited to biocatalysis, bioconversion and bioremediation, either in solution (e.g. in water or mixed solvents) or in immobilized formats.

Mutants of a fungal strain with unexpectedly high protein production capacity, while maintaining good growth characteristics and amenability to genetic modification were identified. These mutants are useful as a microbial production system. Disclosed herein is the discovery that modification of an enzyme in the SUMOylation machinery is responsible for the increase in protein production. Protein or enzyme SUMOylation is a post-translational modification mechanism involving the covalent attachment of a member of the SUMO-(small ubiquitin-like modifier)-proteins to lysine residues of the protein or enzyme to be modified (SUMOylated) via enzymatic cascade analogous to, but distinct from, the ubiquitination pathway (Wilkinson and Henley, *Biochem. J.* 2010, 428(2): 133-145). Examples of SUMO-proteins are Smt3, SUMO-1, SUMO-2, SUMO-3 and SUMO-4. It has been reported that the effect of protein SUMOylation of the substrate protein may result in altered (increased or decreased) activity, functionality and/or protein interaction of the substrate protein. SUMO-conjugation proceeds via E1, E2 and E3 enzymes. Via the E1 "activating" enzyme, SUMO proteins are activated in an ATP-dependent manner. The activated SUMO protein is then transferred to the substrate protein via an E2 "conjugating" enzyme, often in conjugation with an E3 "ligase" enzyme. SUMO proteases play a role in both de-SUMOylation of the SUMOylated substrate proteins and in activation of precursor SUMO proteins. Multiple E1 activating enzymes, E3 ligases and SUMO proteases are known, however, Ubc9 is the only known E2 conjugating enzyme and is highly conserved across organisms (see, for example, FIG. 8). Known yeast E1 activating enzymes are Aos1 and Uba2. Known mammalian E1 activating enzymes are SAE1 and SAE2. Known yeast E3 ligases are Siz1, Siz2, Cst9 and Mms21. Known mammalian E3 ligases are PIAS1, PIAS3, PIAS4, PIASxα, PIASxβ, PIASy, RanBP2, Pc2, Mms21, HDAC4, HDAC7, MUL1, Rhes, TOPORS, TLS, FUS, RSUME, ZMIZ1, NSE2, and TRAF7. Known yeast SUMO proteases are Ulp1 and Ulp2. Known mammalian SUMO proteases are SENP-1, SENP-2, SENP-3, SENP-4, SENP-5, SENP-6, SENP-7, DESI-1, DESI-2 and USPL1 (see, for example, Chymokowitch et al., *Bioessays*. 2015, 37(10): 1095-105; and Wilkinson and Henley, *Biochem. J.* 2010, 428(2): 133-145).

Therefore, provided is a modified cell having an increased protein production, wherein said cell has been modified to result in altered SUMOylation. SUMOylation may be altered by modification of a protein of the SUMOylation machinery and/or its encoding gene, or by exposure, incubation or insertion of SUMOylation modifying agents, preferably resulting in a reduction of SUMOylation within the cell. Examples of SUMOylation modifying agents are ginkgolic acid, kerriamycin B, spectomycin B1, chaetochromin A, viomellein and/or a derivative therefrom. Spectomycin B1 and related natural products disclosed in the paper of Hirohama et al., (*ACS Chem, Biol.* 2013, 8, 2635-2642) inhibit SUMOylation by inhibition of Ubc9.

Modification of SUMOylation in a cell may be confirmed using commercially available kits (eg. from Abcam, Cambridge, Mass.) and/or methods known in the art. Methods known in the art include, for example, ATP:PPi isotope exchange assay, determination of E1-catalyzed ATP:AMP exchange rates with thin layer chromatography, or determination of E1-SUMO conjugates by gel-based assay (Alontaga, et al., July 2012, Biochemical Analysis of Protein SUMOylation in *Curr Protoc Mol Biol, Chapter* 10: Unit 10.29).

In embodiments, the modified cell shows an increased protein production as compared to its parental cell as detected under substantially the same or comparable conditions. The increase in protein production may be an increase in total or overall protein production. In embodiments, the modified cell shows an increased protein production of at least 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 5, 6, 7, 8, 9, 10, 15, 20, 25, 30, 35, 40, 45 or at least 50 fold as compared to the parental cell. The "parental cell" is to be understood herein as the ancestor wherefrom the modified cell is directly derived by altering SUMOylation as defined herein. Preferably, the modified cell is directly derived from the parental cell (i) by genetic modification of at least one gene encoding an endogenous protein of the SUMOylation machinery, and/or (ii) by exposure, incubation or insertion of at least one SUMOylation modifying agents, preferably an inhibitor of at least one endogenous protein of the SUMOylation machinery.

Increase in protein production can be measured by any suitable technique known in the art. Protein production can be measured by detecting total or a particular type of protein produced and/or secreted by the cell during a particular period of cell culture. Total or overall protein production can be measured using commercially available assays such as the colorimetric Bradford and Lowry method and the method using commercially available colorimetric methods such as the BCA assay (e.g. Pierce; Biorad). The increase in protein production may be measured by detecting the amount of extracellular protein encoded by detecting the amount of protein present in the culture or fermentation medium of the cell after a defined time. The increase in protein production may be measured by detecting the amount or activity of a particular protein (cellular or extracellular) via methods known in the art.

One of skill in the art will also appreciate that an increase in protein production may enable desirable alterations in production processes. Such improvements may be demonstrated by improvements in production parameters measured by methods known to those of skill in the art. For example, increased protein production may result in increased titer, increased volumetric productivity, increased specific productivity, and/or increased yield. Increased titer may be measured, for example, by amount of protein or enzyme activity per volume of fermentation broth or fermentation supernatant (e.g. gram protein/liter or activity units/liter) at a given time point during fermentation. Increased volumetric productivity may be measured, for example by rate of protein or enzyme activity per volume of fermentation broth or fermentation supernatant (e.g. gram protein/liter/hour or activity units/liter/hour). Increased specific productivity (including, for example, maximum specific productivity) may be measured, for example, by rate of protein or enzyme activity produced per cell mass (e.g., gram protein/gram dry cell weight/hour or activity units/gram dry cell weight/hour). Increased yield may be measured, for example, by amount of protein or enzyme activity produced per amount of carbon or carbon source (e.g., glucose) consumed during fermentation (e.g. gram protein/gram glucose or activity units/gram glucose or gram of carbon in protein/gram carbon fed). Accordingly, provided herein are production processes comprising fermentation of the modified cells herein to produce a product wherein at least one production parameter is increased. Such increase may be at least about 1%, at least about 5%, at least about 10%, at least about 25%, at least about 30%, at least about 40%, at least about 50%, at least about 60%, at least about 70%, at least about 80%, at least about 90%, or at least about 100%.

The increase in protein production may be an increase production of a protein of interest of at least 1.1 fold as compared to the production of said protein by the parental cell that lacks the modification of SUMOylation. Preferably, the modified cell shows an increased production of the protein of interest of at least about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 5, 6, 7, 8, 9, 10, 15, 20, 25, 30, 35, 40, 45 or at least about 50 fold as compared to the parental cell. Such protein of interest may be a protein encoded by a transgene acting as a reporter (denominated herein as the reporter protein) that has been introduced in the modified cell in order to detect protein production capacity of the modified cell. In establishing the increase in protein production caused by modification of SUMOylation, both the parental cell and the modified cell comprise the reporter gene, and production of the encoded protein is compared between these cells are kept under substantially the same cultural conditions. Reporter gene production can be measured by a suitable method in the art to identify the amount of reporter gene produced, e.g. fluorescence may be measured in case the reporter gene is a fluorescent protein or enzyme activity may be measured in case the reporter gene is an enzyme.

A suitable reporter transgene comprises a coding sequence of a reporter protein, operably linked to a promoter sequence that allows for expression of the coding sequence of the reporter transgene in the modified cell and its parental cell. For instance, in case the modified cell is a fungal cell of the strains *Myceliophthora thermophila*, the promoter sequence may be a promoter sequence as disclosed in WO2010/107303 A2, which is incorporated herein by reference. The reporter protein may be a secreted protein, and protein levels can be measured by detecting the levels of extracellular protein. The reporter gene may be linked, e.g., physically linked, to a gene encoding a selectable marker such as, but not limited to, the amdS selectable marker. A reporter gene exemplified herein and suitable for use in a fungal host cell, such as a fungal host cell of the strain *M. thermophila*, is represented by SEQ ID NO: 4, which comprises a chi1 promoter sequence and a cellulase (Eg2) encoding sequence. A further reporter gene exemplified herein and suitable for use in a fungal host cell, such as a fungal host cell of the strain *M. thermophila*, is represented by SEQ ID NO: 5, which comprises a chi1 promoter sequence or a cbh1 promoter sequence and a polygalacturonase (AnPGII) encoding sequence. A further reporter gene exemplified herein and suitable for use in a fungal host cell, such as a fungal host cell of the strain *M. thermophila*, is represented by SEQ ID NO: 6, which comprises a chi1 promoter sequence and a β-xylosidase (Bxl1) encoding sequence. A further reporter gene exemplified herein and suitable for use in a fungal host cell, such as a fungal host cell of *M. thermophila*, comprises a chi1 promoter sequence or a cbh1 promoter sequence and a sequence encoding a glucoamylase, such as a *T. reesei* glucoamylase. A further reporter gene exemplified herein and suitable for use in a fungal host cell, such as a fungal host cell of *M. thermophila*, comprises a chi1 promoter sequence or a cbh1 promoter sequence and sequence encoding phytase, for example a *Buttiauxella* sp. phytase variant (SEQ ID Nos 53 and 54, respectively). An example sequence encoding a phytase suitable for expression in a fungal cell may comprise the sequence of nucleotides 1905-3184 of SEQ ID NO: 40. Accordingly, suitable proteins of interest include, but are not limited to, Eg2, Bxl1, AnPGII, *T. reesei* glucoamylase, and *Buttiauxella* sp. phytase variant.

It will be appreciated that a protein of interest can also be measured using an assay specific to the protein. Such assays are known to those of skill in the art and may include, for example, binding assays, HPLC, ELISA, gel densitometry, or methods useful for determination of total protein levels. Also, as demonstrated in the Examples, increase in production of an enzyme protein of interest may be measured using an activity assay appropriate for the protein of interest. One of ordinary skill in the art will readily be able to select an appropriate measurement method for the desired protein.

In an embodiment, SUMOylation has been altered in the modified cell by genetic modification of at least one gene of the SUMOylation pathway, such as a gene encoding an endogenous SUMOylation enzyme or a gene encoding an endogenous SUMO protein. In embodiments, the genetic modification may be a targeted genetic modification of at least one gene of the SUMOylation pathway, such as a gene encoding an endogenous SUMOylation enzyme or a gene encoding an endogenous SUMO protein. Examples of proteins of the SUMOylation machinery are: Ubc9, Smt3, SUMO-1, SUMO-2, SUMO-3 and SUMO-4, Siz1, Siz2, Cst9, Mms21, PIAS1, PIAS3, PIAS4, PIASxα, PIASxβ, PIASy, RanBP2, Pc2, Mms21, HDAC4, HDAC7, MUL1, Rhes, TOPORS, TLS, FUS, RSUME, ZMIZ1, NSE2, TRAF7, Ulp1, Ulp2, Aos1, Uba2, SENP-1, SENP-2, SENP-3, SENP-4, SENP-5, SENP-6, SENP-7, DESI-1, DESI-2 and USPL1. The genetic modification may encompass one or more point mutations, one or more insertions of a heterologous sequence and/or one or more deletions of (part of) the endogenous sequence of the gene encoding said SUMOylation enzyme or protein. The point mutations(s), insertion(s) and/or deletion(s) may be located in the coding sequence and/or in a regulating sequence. Examples of an expression regulation sequence are a promoter sequence, a terminator sequence, a promoter activating sequence and a sequence encoding transcription factors. The modification may result in removal or disruption of the whole or part of the gene encoding the endogenous SUMOylation enzyme or protein, or replacing all or part of the gene for instance with a gene encoding a selection marker. An example of a suitable selection marker is the AmdS selectable marker. The modification may encompass "knocking out" the endogenous copy of the gene. A "knock out" of a gene refers to a molecular biological technique by which the gene in the organism is made inoperative, so that the expression of the gene is substantially reduced or eliminated. Further encompassed are point mutations resulting in a reduced or eliminated enzyme or protein production and/or activity.

The genetic modification may result in altered production, activity or both an altered production and activity of the encoding SUMOylation enzyme or protein. The genetic modification may result in a reduced or even abolished production and/or activity of the encoded SUMOylation enzyme or protein, and may result in reduced or abolished SUMOylation.

Such genetic modification can be made using methods known to those of skill in the art equipped with the sequence of a gene encoding a SUMOylation enzyme or protein. Expression regulating sequences are readily identifiable by those of skill in the art. Suitable methods for genetic modification include those known to those of skill in the art and include, but are not limited to, those exemplified herein, homologous recombination, RNA silencing, and CRISPR/Cas systems (Timberlake, et al. 1989, Science 244(4910): 1313-1317.; Moore, p. 36-66, in Biotecnology Vol III: Fundamentals in Biotechnol. Eds. Doelle, Robek, Berovic (2009); Singh, et al. 2017, Gene 599: 1-18). Suitable reagents and methods are likewise known in the art and/or are commercially available (see, for example, WO2016100568A1, WO2016100272A1 and WO2016100571A1, each of which is incorporated herein by reference). For example, purified Cas9 protein and guide RNAs, or kits to make guide RNAs, can be obtained from PNA BIO (www.pnabio.com; Newbury Park, Calif.), NEB (www.neb.com; Ipswich, Mass.), ThermoFisher (www.thermofisher.com; Waltham, Mass.), and IDT (www.idtdna.com or www.idtdna.com/site/order/oligoentry/index/crispr/2 nm; Coralville, Iowa).

Production of endogenous SUMOylation enzymes or protein can be detected by techniques known in the art. The genetic modification of the modified cell may result in a reduction of total amount of transcripts of the modified SUMOylation enzyme or protein as can be detected by a suitable assay known in the art, for instance via RNA-seq as exemplified herein (referred is to Example 1 of this disclosure). The amount of said transcripts in the modified cell may be reduced by at least about 0.2, 0.3, 0.4, 0.5, 0.6, 0.7, 0.8. 0.9, 1, 1.5, 2, 2.5, 3, 4, 5, 6, 7, 8, 9, 10, 15, 20, 25, 30, 45, 50, 60, 70, 80, 90, or at least 100 fold as compared to the amount of said transcripts in the parental cell. In combination with the indicated reduction defined above, the genetic modification may be such that the amount of said transcripts is not reduced to zero, but the residual amount of said transcripts is at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% of the amount of said transcripts present in the parental cell.

The genetically modified cell structurally differs from the parental cell in that it comprises a genetic modification. The modified cell may have been directly obtained from the parental cell by introducing the genetic modification. The modified gene may be any one of the genes encoding the proteins selected from the group consisting of Ubc9, Smt3, SUMO-1, SUMO-2, SUMO-3 and SUMO-4, Siz1, Siz2, Cst9, Mms21, PIAS1, PIAS3, PIAS4, PIASxα, PIASxβ, PIASy, RanBP2, Pc2, Mms21, HDAC4, HDAC7, MUL1, Rhes, TOPORS, TLS, FUS, RSUME, ZMIZ1, NSE2, TRAF7, Ulp1, Ulp2, SENP-1, SENP-2, SENP-3, SENP-4, SENP-5, SENP-6, SENP-7, DESI-1, DESI-2 and USPL1, and homologs of any of these proteins or enzymes. Homologs can be identified in a particular cell of interest using methods known in the art, for example, sequence alignments, generation of phylogenetic trees and analysis. The genetic modification may encompass random or site-directed mutation, deletion, disruption, silencing of coding sequences and/or expression regulatory sequences of genes encoding one or more SUMOylation proteins that result in an increase in protein production by the cell comprising the modification as defined herein, i.e. as compared to protein production by its parental cell when tested under substantially the same conditions.

The genetic modification may comprise or consist of a modification of the gene encoding Ubc9. The endogenous ubc9 gene may any one known to one of skill in the art, for example, the ubc9 gene encoding Ubc9 of *Myceliophthora thermophila* (SEQ ID NO: 2), *Neurospora crassa* Ubc9 (nucleic acid SEQ ID NO: 8; protein SEQ ID NO: 9; Accession Nos.: NCU04302; XM_955999), *Aspergillus nidulans* Ubc9 (nucleic acid SEQ ID NO: 10; protein SEQ ID NO: 11; Accession No.: AN_4399), *Cryptococcus neoformans* (nucleic acid SEQ ID NO: 12; protein SEQ ID NO: 13; Accession No: CNAG_04328), *Saccharomyces cerevisae* Ubc9 (nucleic acid SEQ ID NO: 14; protein SEQ ID NO: 15; Accession Nos: YDL064W; Z74112.1), *Aspergillus niger* Ubc9 (nucleic acid SEQ ID NO: 45; protein SEQ ID NO: 46), and *Trichoderma reesei* Ubc9 (promoter sequence SEQ ID NO: 47; coding SEQ ID NO: 48; cDNA SEQ ID NO: 49, protein SEQ ID NO: 50). Sequence information may be found, for example, in public databases, such as in JGI MycoCosm (genome.jgi.doe.gov/programs/fungi/index.jsf); National Center for Biotechnology Information ("NCBI"; www.ncbi.nlm.nih.gov); *Aspergillus* Genome Database ("AsGD"; www.aspergillusgenome.org); or *Saccharomyces* Genome Database ("SGD"; www.yeastgenome.org). The genetic modification may be in a gene encoding a protein having comprising at least 70%, at least 75%, at least 80%, at least 85%, at least 90%, or at least 95% sequence identity to, or comprising, the sequence of one or more or both of the following sequence motifs: RLQEERKQWRKDHPFGF (SEQ ID NO: 42) and KPPKCKFTPPLFHPNVYPSGTVCLSIL (SEQ ID NO: 43). The genetic modification may be a modification of a regulating region of the ubc9 gene, for example in the promoter sequence of the ubc9 gene, for example by an expression cassette insertion in the ubc9 promoter region, upstream of the protein coding sequence. An example of an insertion cassette for disruption of the ubc9 promoter sequence in *M. thermophila* is represented by SEQ ID NO: 3. Examples of target sequences for disruption of the ubc9 promoter sequence in *T. reesei* are represented by SEQ ID Nos: 30, 31, and 32. An example of an insertion cassette for disruption of the ubc9 promoter sequence in *A. niger* is represented by SEQ ID NO: 26. Also contemplated herein are other genetic modifications resulting in modification of ubc9 expression, Ubc9 production or activity, such as inactivating mutants of Ubc9 or gene disruptions in the ubc9 coding sequence, preferably resulting in reduced or abolished Ubc9 production and/or activity.

The modified cell may be characterized in that it comprises an endogenous ubc9 (ubiquitin conjugating enzyme or E2 enzyme) gene that has been modified to increase protein production. The endogenous ubc9 gene comprising the modification in the modified cell may have a wild type (unmodified) counterpart that has at least 40%, 50%, 60%, 70%, 80%, 85%, 90%, 91%, 92%, 93%, 94%, 95%, 96%, 97%, 98%, 99% or 100% sequence identity to SEQ ID NO: 1 over its whole length, or that has at least 40%, 50%, 60%, 70%, 80%, 85%, 90%, 91%, 92%, 93%, 94%, 95%, 96%, 97%, 98%, 99% or 100% sequence identity to SEQ ID NO: 1 delimited by the nucleotides on positions 1070 and 2195 (i.e. SEQ ID NO: 1 (1070-2195)) over its whole length, or that has at least 40%, 50%, 60%, 70%, 80%, 85%, 90%, 91%, 92%, 93%, 94%, 95%, 96%, 97%, 98%, 99% or 100% sequence identity to the sequence of SEQ ID NO: 1 delimited by the nucleotides on positions 1302 and 1994 (i.e. SEQ ID NO: 1 (1302-1994) representing the open reading frame) over its whole length. The endogenous ubc9 gene comprising the modification in the modified cell may have a wild type counterpart comprising a sequence that has at least the modified cell may have a wild type (unmodified) counterpart that has at least 40%, 50%, 60%, 70%, 80%, 85%, 90%, 91%, 92%, 93%, 94%, 95%, 96%, 97%, 98%, 99% or 100% sequence identity to SEQ ID NO: 47 or to SEQ ID NO: 48 over its whole length. The endogenous ubc9 gene comprising the modification in the modified cell may have a wild type counterpart comprising a sequence that has at least the modified cell may have a wild type (unmodified) counterpart that has at least 40%, 50%, 60%, 70%, 80%, 85%, 90%, 91%, 92%, 93%, 94%, 95%, 96%, 97%, 98%, 99% or 100% sequence identity to the promoter or coding portion of SEQ ID NO: 45.

The endogenous ubc9 gene comprising the genetic modification in the modified cell may encode an Ubc9 protein having a sequence that has at least 40%, 50%, 60%, 70%, 80%, 85%, 90%, 91%, 92%, 93%, 94%, 95%, 96%, 97%, 98%, 99% or 100% sequence identity to SEQ ID NO: 2 over its whole length. The endogenous ubc9 gene comprising the genetic modification in the modified cell may encode an Ubc9 protein having a sequence that has at least 40%, 50%, 60%, 70%, 80%, 85%, 90%, 91%, 92%, 93%, 94%, 95%, 96%, 97%, 98%, 99% or 100% sequence identity to SEQ ID NO: 50 over its whole length. The endogenous ubc9 gene comprising the genetic modification in the modified cell may encode an Ubc9 protein having a sequence that has at least 40%, 50%, 60%, 70%, 80%, 85%, 90%, 91%, 92%, 93%, 94%, 95%, 96%, 97%, 98%, 99% or 100% sequence identity to SEQ ID NO: 46 over its whole length.

Equipped with this disclosure, one of skill in the art can readily identify a ubc9 sequence in an organism of interest. For example, an alignment of over 600 publicly available Ubc9 orthologs revealed two prominent stretches of extended and strong sequence conservation, named herein motif 1 (17 aa; SEQ ID NO: 42) and motif 2 (27 aa; SEQ ID NO: 43) (see FIG. 8). Both stretches are located within the "ubiquitin-conjugating enzyme" protein domain (PF00179; pfam.xfam.org/) that characterize ubc proteins. These stretches may be used to identify ubc9 from other proteins that contain the PF00179 domain.

The modified cell may have an insertion or disruption of an endogenous ubc9 gene promoter sequence. The ubc9 promoter sequence may be disrupted by insertion of an expression cassette, for example, the ubc9 promoter sequence is disrupted by insertion of an expression cassette on a position that is analogous to nucleotides within the promoter sequence of the ubc9 gene of *M. thermophila* that are represented by the nucleotides on position 1257 and 1258 of SEQ ID NO: 1. Promoter sequence disruption at this position was found to result in an unexpected increase in overall protein production, more in particular in expression of transduced reporter genes that encode extracellularly secreted proteins. Without wishing to be bound by any theory, disruption of the promoter sequence is likely to impair functional expression of the encoded Ubc9 protein, which, possibly via its crucial role in post-translational modification-pathways, results in an increase in net protein production. It will be appreciated that endogenous ubc9 gene modification is not limited to promoter sequence disruption. Contemplated herein are ubc9 gene modifications resulting in impairing or abolishing functional expression of the encoded ubc9 protein. Moreover, contemplated herein are SUMOylation enzyme, protein or gene modifications resulting in an overall increase in protein production.

In another embodiment, or in combination with the embodiment defined above, the modified cell is exposed to one or more biological or chemical agents that alter SUMOylation, such as SUMOylation enzyme inhibitors or activators. The modified cell may be exposed to at least one inhibitor of a SUMOylation enzyme at a concentration effective to inhibit activity of said enzyme. The inhibitor may be any one selected from the group consisting ginkgolic acid, kerriamycin B, spectomycin B1, chaetochromin A, viomellein and/or a derivative therefrom. Spectomycin B1 and related natural products disclosed in the paper of Hirohama et al., (*ACS Chem, Biol.* 2013, 8, 2635-2642) inhibit SUMOylation by inhibition of Ubc9. Therefore, the modified cell may be exposed to Spectomycin B1 and/or related natural products disclosed in the paper of Hirohama et al., (*ACS Chem, Biol.* 2013, 8, 2635-2642) at a concentration effective to inhibit activity of said enzyme. The modified cell may be exposed to an agent that alters SUMOylation in a concentration of said agent that results in an increase in protein production as defined herein, i.e. as compared to its parental cell when tested under substantially the same conditions. The modified cell exposed to one or more SUMOylation enzyme inhibitors or activators as defined herein may be structurally similar to the parental cell and only differs therefrom in that it is exposed to said inhibitor(s) or activator(s). The modified cell may be exposed to an inhibitor to result in a reduced enzyme activity by at least about 0.2, 0.3, 0.4, 0.5, 0.6, 0.7, 0.8. 0.9, 1, 1.5, 2, 2.5, 3, 4, 5, 6, 7, 8, 9, 10, 15, 20, 25, 30, 45, 50, 60, 70, 80, 90, or at least about 100 fold as compared to the enzyme activity of the parental cell. In combination with the indicated reduction defined above, the resulting enzyme activity may be such that the amount of enzyme activity is not reduced to zero, but the residual enzyme activity is at least about 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10% of the activity in the parental cell.

As modified cells provided herein show high protein production capacity, modified cells provided herein may be used in industrial protein production, such as, but not limited to, production of pharmaceutical proteins and/or industrial enzymes (also denominated herein "proteins of interest"). A protein of interest may be an endogenous protein or an exogenous protein, i.e. encoded by a transgene. The transgene may encode a homologous or a heterologous protein. The modified cell encoding and producing a protein of interest (or a protein mixture of interest) is also denominated herein as an expression system.

In the embodiment of the invention wherein the protein of interest is a transgene, the modified cell comprises an exogenous expression construct or vector that encodes at least one protein of interest, encoded by a transgene comprised on the expression construct or vector. The expression construct may comprise portions of a gene or polynucleotide encoding the protein of interest that are not part of the coding region for the protein (e.g., introns or regulatory regions of a gene encoding the protein) and may be double stranded, single stranded and can include DNA, RNA, or derivatives of either DNA or RNA, including cDNA, probes and primers, including guide sequences. Optionally, the expression construct encodes for one or more industrial enzymes. The expression construct may be a chimeric expression construct or vector encoding at least two proteins of interest.

It will be appreciated by one skilled in the art that use of recombinant DNA technologies can affect control of expression of transfected expression vectors (encoding either homologous or heterologous proteins) by manipulating, for example, the number of copies of sequences encoding the protein of interest within the host cell, the efficiency with which those sequences encoding the protein of interest are transcribed, the efficiency with which the resultant transcripts are translated, and the efficiency of posttranslational modifications. The transgene may comprise translation enhancing and/or regulating sequences such as promoter sequences suitable for expression in the host cell of interest. Such promoter sequence may be a promoter sequence for expression of proteins in *Myceliophthora thermophila*, such as *Myceliophthora thermophila* C1, are disclosed in WO2010/107303 A2, which is incorporated herein by reference. For example, such promoter sequence may comprise a *Myceliophthora thermophila* chit promoter sequence, such as SEQ ID NO: 51, or a *Myceliophthora thermophila* cbh promoter sequence, such as SEQ ID NO: 52, or a promoter sequence having at least about 85%, at least about 90%, at least about 95% or at least about 99% identity to SEQ ID NO: 51 or 52. Suitable promoter sequences for expression of proteins in *Trichoderma* may include, but are not limited to, a *T. reesei* cbh1, cbh2, egl1, egl2, egl3, egl4, egl5, pki1, gpd1, xyn1, or xyn2 promoter. Additionally, the promoter sequence may be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

The protein or proteins of interest may be an enzyme mixture or multi-enzyme composition. In other words, the modified cell may be further modified to produce further enzymes or enzyme mixtures or multi-enzyme compositions that are beneficial for industrial purposes.

The protein of interest may be, for example, a hemicellulase, a peroxidase, a protease, a cellulase, a xylanase, a lipase, a phospholipase, an esterase, a cutinase, a pectinase, a keratinase, a reductase, an oxidase, a phenol oxidase, a lipoxygenase, a ligninase, a pullulanase, a tannase, a pentosanase, a mannanase, a beta-glucanase, an arabinosidase, a hyaluronidase, a chondroitinase, a laccase, an amylase, a glucoamylase, a mixture thereof, a functional fragment thereof, or a mixture of one or more of the enzymes or functional fragments thereof. Non-limiting examples of proteins may further include proteins or enzymes involved in starch metabolism, proteins or enzymes involved in glycogen metabolism, acetyl esterases, aminopeptidases, amylases, arabinases, arabinofuranosidases, carboxypeptidases, catalases, cellulases, chitinases, chymosin, cutinase, deoxyribonucleases, epimerases, esterases, α-galactosidases, β-galactosidases, α-glucanases, glucan lysases, endo-β-glucanases, glucoamylases, glucose oxidases, a-glucosidases, β-glucosidases, glucuronidases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, peroxidases, phenoloxidases, phytases, polygalacturonases, proteases, rhamno-galacturonases, ribonucleases, thaumatin, transferases, transport proteins, transglutaminases, xylanases, hexose oxidase (D-hexose: 02-oxidoreductase, EC 1.1.3.5), variants thereof, functional fragments thereof, or combinations thereof. The protein of interest may also be a peptide hormone, a growth factor, a clotting factor, a chemokine, a cytokine, a lymphokine, an antibody, a receptor, an adhesion molecule, a microbial antigen (e.g., HBV surface antigen, HPV E7, etc.), or a variant, functional fragment, or a mixture of two or more, three or more, four or more, five or more, or six or more of the above substances. Mixtures of enzymes may include, for example, combinations disclosed in PCT Application Publication Nos WO2008/153903, WO2012/125951 and/or WO2012/125937, each of which is incorporated herein by reference.

The modified cell may be a cell that encodes (either endogenous and/or transgenically) and produces a multi-enzyme composition suitable for degrading a lignocellulosic and/or hemicellulosic material. Such multi-enzyme composition may comprise at least one cellobiohydrolase, at least one xylanase, at least one endoglucanase, at least one β-glucosidase, at least one β-xylosidase, and at least one accessory enzyme. In embodiments, the multi-enzyme composition may lack enzymes which lead to the formation of cellobionolactone/cellobionic acid and/or gluconolactone/gluconic acid. A xylanase may be an endoxylanase, an exoxylanase, or a β-xylosidase. An accessory enzyme can have the same or similar function or a different function as an enzyme or enzymes in a core set of enzymes. Suitable accessory enzymes have been described elsewhere herein, and can generally include cellulases, xylanases, ligninases, amylases, lipidases, or glucuronidases, for example. Some accessory enzymes for example can include enzymes that when contacted with biomass in a reaction, allow for an increase in the activity of enzymes (e.g., hemicellulases) in the multi-enzyme composition. An accessory enzyme or enzyme mix may be composed of enzymes from (1) commercial suppliers; (2) cloned genes expressing enzymes; (3) complex broth (such as that resulting from growth of a microbial strain in media, wherein the strains secrete proteins and enzymes into the media); (4) cell lysates of strains grown as in (3); and, (5) plant material expressing enzymes capable of degrading lignocellulose. In some embodiments, the accessory enzyme is a glucoamylase, a pectinase, or a ligninase. Accessory enzymes include an enzyme selected from the group consisting of: cellulase, glucosidase, lytic polysaccharide monooxygenase (or GH61 or polypeptide having cellulolytic enhancing activity), xylanase, xylosidase, ligninase, glucuronidase, arabinofuranosidase, arabinase, arabinogalactanase, ferulic acid esterase, lipase, pectinase, glucomannase, amylase, laminarinase, xyloglucanase, galactanase, galactosidase, glucoamylase, pectate lyase, chitosanase, exo-β-D-glucosaminidase, cellobiose dehydrogenase, and acetyl xylan esterase. In embodiments, the accessory enzymes are present in an enzyme mixture in the absence of enzymes which lead to the formation of cellobionolactone/cellobionic acid and/or gluconolactone/gluconic acid. The multi-enzyme composition may further comprise at least one hemicellulase. A hemicellulase may be selected from the group consisting of a xylanase, an arabinofuranosidase, an acetyl xylan esterase, a glucuronidase, an endo-galactanase, a mannanase, an endo-arabinase, an exo-arabinase, an exo-galactanase, a ferulic acid esterase, a galactomannanase, a xyloglucanase, and mixtures thereof. A xylanase may be selected from the group consisting of endoxylanases, exo-xylanases, and β-xylosidases. The multi-enzyme composition may further comprise at least one cellulase.

Multi-enzyme compositions contemplated herein may be obtained from the modified cell as a crude fermentation product optionally subjected to a purification step. The multi-enzyme composition may further comprise one or more accessory enzymes. Accessory enzymes may include at least one enzyme selected from the group consisting of: cellulase, glucosidase, lytic polysaccharide monooxygenase (or GH61 or polypeptide having cellulolytic enhancing activity), xylanase, xylosidase, ligninase, glucuronidase, arabinofuranosidase, arabinase, arabinogalactanase, ferulic acid esterase, lipase, pectinase, glucomannanase, amylase, laminarinase, xyloglucanase, galactanase, galactosidase, glucoamylase, pectate lyase, chitosanase, exo-β-D-glucosaminidase, cellobiose dehydrogenase, acetylxylan esterase and acetylesterase. In some embodiments, the accessory enzyme is produced by culturing the modified cell on a substrate to produce the enzyme. The multi-enzyme composition may further comprise at least one protein for degrading an arabinoxylan-containing material or a fragment thereof that has biological activity. The multi-enzyme composition may further comprise at least one endoxylanase, at least one β-xylosidase, and at least one arabinofuranosidase. An arabinofuranosidase may comprise an arabinofuranosidase with specificity towards single substituted xylose residues, an arabinofuranosidase with specificity towards double substituted xylose residues, or a combination thereof.

Multi-enzyme compositions may also include cellulases, hemicellulases (such as xylanases, including endoxylanases, exoxylanases, and β-xylosidases; mannanases, including endomannanases, exomannanases, and β-mannosidases), ligninases, amylases, glucuronidases, proteases, esterases (including ferulic acid esterase), lipases, glucosidases (such as β-glucosidase), and xyloglucanases.

Also contemplated is a modified cell that produces mixtures that comprise enzymes that are capable of degrading cell walls and releasing cellular contents. Such cell may be a bacterial cell, or a cell of an alga, fungus, or a plant which produces the enzymes naturally or by virtue of being genetically modified to express the enzyme or enzymes.

In an embodiment, the multi-enzyme composition is employed in a process to obtain fermentable products, such as sugars, from degrading biomass and/or lignocellulosic material, such as biomass rich in hemicellulose, as defined herein. Said lignocellulosic material may be, for example, agro-waste or a residue produced by agriculture and forestry. The lignocellulosic material may be, for example, corn stover, bagasse, or wheat straw. The lignocellulosic material may be pretreated lignocellulosic material. Pretreated lignocellulosic material may be produced, for example, by subjecting a biomass material to elevated temperature and the addition of dilute acid, concentrated acid or dilute alkali solution. Pretreated lignocellulosic material may be produced, for example, by subjecting a biomass material to low ammonia concentration under conditions of high solids. The lignocellulosic material may be partially or completely degraded to fermentable sugars. Economical levels of degradation at commercially viable costs are contemplated. Due in part to the many components that comprise biomass and lignocellulosic materials, enzymes or a mixture of enzymes capable of degrading xylan, lignin, protein, and carbohydrates are needed to achieve saccharification. The one or more additional enzymes may include enzymes or compositions thereof with, for example, oxidoreductases, cellobiohydrolase, endoglucanase, β-glucosidase, xylanase and other hemicellulase activities. These enzyme compositions are suitable for degrading biomass, such as biomass rich in hemicellulose, such as pulp, as defined herein.

The multi-enzyme composition is to dissolve pulp for the production of chemicals such as, but not limited to, rayon, cellophane and several chemicals such as cellulose esters (acetates, nitrates, propionates and butyrates) and cellulose ethers (carboxymethyl cellulose and methyl and ethyl cellulose) and ethanol (for instance as bioethanol biofuel). Also contemplated is a multi-enzyme composition for paper and pulp bleaching. The multi-enzyme composition may be used to improve bleachability of pulp in the pulp and paper industry.

The modified cell (e.g., a host cell or production organism) may include any microorganism such as a protist, an alga, a fungus, or other eukaryotic microbe, plant, insect, or animal cell and may be a yeast or a filamentous fungus. The modified cell may be any fungal (e.g., filamentous fungi or yeast or mushrooms), alga, plant, insect, or animal cell that can be transfected. The modified cell is may be a cultured cell. Suitable genera of yeast include, but are not limited to, *Saccharomyces, Schizosaccharomyces, Candida, Hansenula, Pichia, Kluyveromyces*, and *Phaffia*. Suitable yeast species include, but are not limited to, *Saccharomyces cerevisiae, Schizosaccharomyces pombe, Candida albicans, Hansenula polymorpha, Pichia pastoris, Pichia canadensis, Kluyveromyces marxianus* and *Phaffia rhodozyma*.

Suitable fungal genera include, but are not limited to, *Chrysosporium, Thielavia, Neurospora, Aureobasidium, Filibasidium, Piromyces, Corynascus, Cryptococcus, Acremonium, Tolypocladium, Scytalidium, Schizophyllum, Sporotrichum, Penicillium, Gibberella, Myceliophthora, Mucor, Aspergillus, Fusarium, Humicola*, and *Trichoderma, Talaromyces, Rasamsonia* and anamorphs and teleomorphs thereof. Suitable fungal species include, but are not limited to, *Aspergillus niger, Aspergillus oryzae, Aspergillus nidulans, Aspergillus japonicus, Absidia coerulea, Rhizopus oryzae, Myceliophthora thermophila, Neurospora crassa, Neurospora intermedia, Trichoderma reesei, Trichoderma longibrachiatum, Penicillium canescens, Penicillium solitum, Penicillium funiculosum, Acremonium alabamense, Thielavia terrestris, Sporotrichum thermophile, Sporotrichum cellulophilum, Chaetomium globosum, Corynascus heterothallicus, Talaromyces emersonii, Rasamsonia emersonii* and *Talaromyces flavus*.

The modified cell may be a (further) genetically modified cell or microorganism, i.e. comprising (further) genetic modifications in addition to the possible modification of the gene encoding a SUMOylation enzyme or SUMO-protein and introduction of transgenes encoding one or more proteins of interest as detailed herein. The cell may be further modified in order to produce reduced amounts or to lack the production of enzymes that interfere/compete with the expression and/or secretion of the protein of interest and/or with the production or enzymatic activity of the protein of interest. For instance, such cell may be modified in order to downregulate the interfering enzyme activity. Downregulation may be achieved, for example, by introduction of inhibitors (chemical or biological) of the enzyme activity, by manipulating the efficiency with which those nucleic acid molecules are transcribed, the efficiency with which the resultant transcripts are translated, and the efficiency of post-translational modifications, or by gene mutation, disruption or deletion. Alternatively, the activity of the enzyme production or activity may be upregulated in case the enzyme production or activity has a positive effect on the production or activity of the enzyme of interest. Such enzymes may be accessory enzymes, for instance in case the enzyme of interest is for degrading lingo-cellulosic material. Also contemplated herein is downregulating activity of one or more enzymes while simultaneously upregulating activity of one or more enzymes to achieve the desired outcome.

The modified cell may be a fungal cell, or even a filamentous fungal cell. The modified cell may be a fungal cell from the genus selected form the group consisting of *Chrysosporium, Thielavia, Neurospora, Aureobasidium, Filibasidium, Piromyces, Corynascus, Cryptococcus, Acremonium, Tolypocladium, Scytalidium, Schizophyllum, Sporotrichum, Penicillium, Gibberella, Myceliophthora, Mucor, Aspergillus, Fusarium, Humicola, Trichoderma, Talaromyces* and *Rasamsonia*. The modified cell may be a *Myceliophthora thermophila* cell, such as of the strain C1 (VKM F-3500 D) or a mutant strain derived therefrom (e.g., UV13-6 (Accession No. VKM F-3632 D); NG7C-19 (Accession No. VKM F-3633 D); UV18-25 (VKM F-3631D), UV18#100f (CBS122188), W1L (CBS122189), or W1L#100L (CBS122190)). The strain may be a strain with reduced expression of protease and (hemi-)cellulase, and may even be free of protease and (hemi-)cellulase expression. The strain may be W1 L#100.1Δpyr5Δalp1, also denominated as the LC strain (Visser H, et al., Ind. Biotechnol. 7:214-222, 2011 and WO2010/107303, which is incorporated herein by reference. As described in U.S. Pat. No. 6,015,707 or U.S. Pat. No. 6,573,086 a strain called C1 (Accession No. VKM F-3500 D), was isolated from samples of forest alkaline soil from Sola Lake, Far East of the Russian Federation. This strain was deposited at the All-Russian Collection of Microorganisms of Russian Academy of Sciences (VKM), (www.vkm.ru; Bakhurhina St. 8, Moscow, Russia, 113184; Prospekt Nauki No. 5, Pushchino, Moscow Region, 142290, Russia) under the terms of the Budapest Treaty on the International Regulation of the Deposit of Microorganisms for the Purposes of Patent Procedure on Aug. 29, 1996 (by A. P. Sinitsyn, O. N. Okunev, I. V. Solov'eva, V. M. Chernoglasov, M. A. Emalfarb, A. Ben-Bassat; "FermTech" LTD Acad. Kapitsky str. 32-2, Moscow, 117647, Russia), as *Chrysosporium lucknowense* Garg 27K, VKM F-3500 D. Various mutant strains of C1 have been produced and these strains have also been deposited at the All-Russian Collection of Microorganisms of Russian Academy of Sciences (VKM) (Bakhurhina St. 8, Moscow, Russia, 113184; Prospekt Nauki No. 5, Pushchino, Moscow Region, 142290, Russia), under the terms of the Budapest Treaty on the International Regulation of the Deposit of Microorganisms for the Purposes of Patent Procedure on Sep. 2, 1998 (by O. N. Okunev, A. P. Sinitsyn, V. M. Chernoglasov, and M. A. Emalfarb; "FermTech" LTD, Acad. Kapitsy str., 32-2, Moscow, 117647, Russia) or at the Centraal Bureau voor Schimmelcultures (CBS), (Uppsalalaan 8, 3584 CT Utrecht, The Netherlands) for the purposes of Patent Procedure on Dec. 5, 2007 (by Dyadic Nederland B. V., Nieuwe Kanaal 7s, 6709 PA Wageningen, Nederland). For example, Strain C1 was mutagenised by subjecting it to ultraviolet light to generate strain UV13-6 (Accession No. VKM F-3632 D; deposited with VKM on Sep. 2, 1998). This strain was subsequently further mutated with N-methyl-N'-nitro-N-nitrosoguanidine to generate strain NG7C-19 (Accession No. VKM F-3633 D; deposited with VKM on Sep. 2, 1998). This latter strain in turn was subjected to mutation by ultraviolet light, resulting in strain UV18-25 (Accession No. VKM F-3631 D; deposited with VKM on Sep. 2, 1998). UV18-25 has been mutated with ultraviolet light and selected for low protease activity, denoted herein as UV18#100f (CBS122188; deposited with CBS Dec. 5, 2007). Strain UV18-25 has also been mutated with ultraviolet light and selected for low cellulose activity resulting in strain W1L (Accession No. CBS122189; deposited with CBS Dec. 5, 2007), which was subsequently subjected to mutation by ultraviolet light, and selected for low protease activity resulting in strain W1L#100L (Accession No. CBS122190; deposited with CBS Dec. 5, 2007). Strain C1 was initially classified as a *Chrysosporium lucknowense* based on morphological and growth characteristics of the microorganism, as discussed in detail in U.S. Pat. No. 6,015,707, U.S. Pat. No. 6,573,086 and patent PCT/NL2010/000045, each incorporated herein by reference. The C1 strain was subsequently reclassified as *Myceliophthora thermophila* based on genetic tests. *C. lucknowense* has also appeared in the literature as *Sporotrichum* thermophile. In a further embodiment, the modified cell is a strain showing high levels of cellulose production (HC strain), such as, but not limited to, C1, UV13-6, NG7C-19, UV18-25 or UV18#100f (Accession No. CBS122189), or derivatives thereof. A modified cell derived from UV18#100f and having a modified SUMOylation machinery as further detailed herein, such as a promoter insertion in the ubc9 gene as defined herein, is in particular of interest in the production of cellulase. The cell of the HC strain as detailed herein having a modified SUMOylation machinery may further be genetically modified to reduce protease expression. The modified cell may further be genetically modified resulting in a reduced or eliminated activity of enzymes that cause the formation of cellobionolactone/cellobionic acid and/or gluconolactone/gluconic acid. Such further genetically modified cell or microorganism may be a fungal cell lacking functional genes encoding enzymes causing the formation of cellobionolactone/cellobionic acid and/or gluconolactone/gluconic acid e.g., may be generated by gene deletion, gene disruption, gene silencing or mutation; or by deletion, disruption or mutation of gene expression regulatory sequences such as promoter sequences, terminator sequences, promoter activating sequences and sequences encoding transcription factors; or by random or site-directed mutation of the genes encoding the enzymes causing the formation of cellobionolactone/cellobionic acid and/or gluconolactone/gluconic acid. The further modified fungus may be a modified fungus wherein the one or more genes encoding enzymes responsible for the production of one or more products selected from cellobionolactone, cellobionic acid, gluconolactone, and gluconic acid encode a cellobiose dehydrogenase (CDH) is deleted, disrupted or mutated. The one or more genes may encode an enzyme having an amino acid sequence of the cellobiose dehydrogenase (CDH) selected from a group of polypeptides having at least 90%, 95%, or 99% identity with any of the endogenous CDH1, CDH2 and CDH3 of *Myceliophthora thermophila* C1 as disclosed in WO2013/159005A2, which is incorporated herein by reference. The further modified fungus may be a further modified fungus wherein the gene encoding the cellobiose dehydrogenase (CDH) CDH1, CDH2, or CDH3 is deleted, disrupted or mutated. The further modified fungus may be a fungus wherein CDH activity is reduced from about 50% to about 100%, or at least 75%, 90%, or 95%, when measured by a ferricyanide reduction assay as disclosed in WO2013/159005A2, incorporated by reference. The gene encoding CDH1 or encoding CDH2 in *Myceliophthora thermophila* C1 may be knocked out. The genes encoding CDH1 and CDH2 in *Myceliophthora thermophila* C1 may be both knocked out (double knock out), such as described in WO2013/159005A2 and WO2012/061432A1 which are incorporated herein by reference.

In embodiments, the host cell is a modified *Trichoderma reesei* cell. The modified cell may comprise a deletion of one or more or all of the cbh1, cbh2, egl1 and egl2 genes (as described in US2015/0030717A1, incorporated herein by reference). The modified cell may comprise deletion of an endo-glucosaminidase gene. In embodiments, the deletion prevents deglycoslylation of secreted proteins.

Further suitable cells include insect cells (most particularly *Drosophila melanogaster* cells, *Spodoptera frugiperda* Sf9 and Sf21 cells and *Trichoplusia* High-Five cells), nematode cells (particularly *C. elegans* cells), avian cells, amphibian cells (particularly *Xenopus laevis* cells), reptilian cells, and mammalian cells (most particularly human, simian, canine, rodent, bovine, or sheep cells, e.g. NIH3T3, CHO (Chinese hamster ovary cell), COS, VERO, BHK, HEK, and other rodent or human cells).

The present invention also contemplates genetically modified organisms such as algae, and plants having a modified SUMOylation machinery as detailed herein. The plants may be used for production of the enzymes, and/or as the lignin, lignocellulosic, cellulosic and/or hemicellulosic material used as a substrate for saccharification processes. Methods to generate recombinant plants are known in the art. For instance, numerous methods for plant transformation have been developed, including biological and physical transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pp. 67-88. In addition, vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pp. 89-119.

The most widely utilized method for introducing an expression vector into plants is based on the natural transformation system of *Agrobacterium*. See, for example, Horsch et al., *Science* 227:1229 (1985). Descriptions of *Agrobacterium* vector systems and methods for *Agrobacterium*-mediated gene transfer are provided by numerous references, including Gruber et al., supra, Miki et al., supra, Moloney et al., *Plant Cell Reports* 8:238 (1989), and U.S. Pat. Nos. 4,940,838 and 5,464,763, both incorporated by reference.

Another generally applicable method of plant transformation is microprojectile-mediated transformation, see e.g., Sanford et al., *Part. Sci. Technol.* 5:27 (1987), Sanford, J. C., *Trends Biotech.* 6:299 (1988), Sanford, J. C., *Physiol. Plant* 79:206 (1990), Klein et al., *Biotechnology* 10:268 (1992). Another method for physical delivery of DNA to plants is sonication of target cells. Zhang et al., *Bio/Technology* 9:996 (1991). Alternatively, liposome or spheroplast fusion have been used to introduce expression vectors into plants. Deshayes et al., *EMBO J.*, 4:2731 (1985), Christou et al., *Proc Natl. Acad. Sci. USA* 84:3962 (1987). Direct uptake of DNA into protoplasts using $CaCl_2$ precipitation, polyvinyl alcohol or poly-L-ornithine have also been reported. Hain et al., *Mol. Gen. Genet.* 199:161 (1985) and Draper et al., *Plant Cell Physiol.* 23:451 (1982). Electroporation of protoplasts and whole cells and tissues have also been described. Donn et al., In Abstracts of VII$^{th}$ International Congress on Plant Cell and Tissue Culture IAPTC, A2-38, p. 53 (1990); D'Halluin et al., *Plant Cell* 4:1495-1505 (1992) and Spencer et al., *Plant Mol. Biol.* 24:51-61 (1994).

Further provided is a process for producing a modified cell as defined herein. As detailed herein above, the modified cell is modified to have modified SUMOylation machinery, either by genetic modification of at least one enzyme or protein of the SUMOylation machinery or by exposing the cell to a SUMOylation enzyme modifier, to increase protein production. Said process may comprise the step of disruption of an expression regulating sequence or the coding sequence of a SUMOylation machinery protein, for example, the ubc9 promoter sequence, by insertion, deletion, or point mutation. Said process may comprise at least one step of targeted genetic modification, wherein said step may be a step in inserting an expression cassette. It will be appreciated that a "targeted" genetic modification utilizes the sequence information of the gene so targeted to create the modification. For example, a targeted genetic modification may employ introduction of an insertion cassette sequence or an antisense sequence or a guide sequence having a sufficient degree of complementarity or homology (as appropriate for the modification strategy) to the targeted gene sequence to direct the modification to the unique gene of interest. Said process may comprise the step of disruption of an expression regulating sequence or the coding sequence of a SUMOylation machinery protein, for example, the ubc9 promoter sequence, by insertion of an expression cassette, wherein the ubc9 promoter sequence is disrupted by insertion of an expression cassette on a position that is homologous to position within the promoter sequence of the ubc9 gene of *M. thermophila* that is represented by the nucleotides on position 1257 and 1258 of SEQ ID NO: 1. A homologous position is to be understood herein as a position within a consecutive sequence or stretch of at least 10, 11, 12, 13, 14, 15, or 20 nucleotides that shares at least 50%, 60%, 70%, 80%, 90 or at least 100% sequence identity to SEQ ID NO: 1, wherein said position may be a position in the middle or centre of the consecutive stretch. Cells or host cells for use as a starting material in the process detailed herein and optional genes to be modified in this process are detailed herein above. The method of the invention may also comprise the step of incubating or exposing the cell to one or more modifiers, such as inhibitors, of at least one SUMOylation enzyme or SUMO protein, such as detailed herein above.

Also provided is a composition comprising the modified cell as defined herein above. Such composition may be a fermentation broth that may be a crude fermentation broth. The fermentation broth may further comprise an endogenous or exogenous (homogenous or heterogenous) protein or mixture of proteins of interest. Such protein or mixture of proteins may be enzyme(s) for degrading lingo-cellulosic material as detailed herein above.

Also provided is a process for producing an expression system comprising the step of transducing a modified cell as defined herein, or a cell obtained by a process for producing such modified cell as defined herein, comprising at least one exogenous expression construct encoding at least one protein of interest. The protein of interest may be a secreted protein, i.e. a protein that is secreted in the extracellular environment after production by the cell. The cell transduced with multiple different expression constructs each expressing different proteins of interest and/or the cell be transduced with a single expression construct encoding multiple different proteins of interest. Optionally, process results in a cell that comprises multiple exogenous expression constructs and/or comprises expression construct or expression constructs encoding for more than one protein. The encoded proteins may be heterologous or homologous. Optionally, the process result is a cell that is capable of producing a mixture of proteins of interest. It will be appreciated by one skilled in the art that use of recombinant DNA technologies can improve control of expression of transfected nucleic acid molecules by manipulating, for example, the number of copies of the nucleic acid molecules within the host cell, the efficiency with which those nucleic acid molecules are transcribed, the efficiency with which the resultant transcripts are translated, and the efficiency of posttranslational modifications. Additionally, the promoter sequence might be genetically engineered to improve the level of expression as compared to the native promoter. Recombinant techniques useful for controlling the expression of nucleic acid molecules include, but are not limited to, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites), modification of nucleic acid molecules to correspond to the codon usage of the host cell, and deletion of sequences that destabilize transcripts.

The present invention is not limited to fungi and also contemplates genetically modified organisms such as algae and plants transformed with one or more nucleic acid molecules disclosed herein. The plants may be used for production of the enzymes, and/or as the lignocellulosic material used as a substrate in the methods of the invention. Methods to generate recombinant plants are known in the art. For instance, numerous methods for plant transformation have been developed, including biological and physical transformation protocols. References thereof are indicated herein above.

The protein or protein mixture of interest may be an industrial applicable protein or protein mixture as further detailed herein above.

Also provided is a process for producing a protein or protein mixture of interest, comprising the step of culturing a modified cell as defined herein, or a modified cell obtained by a process for producing such modified cell or an expression system as defined herein, under conditions effective to produce the protein. The protein may be an endogenous protein or endogenous protein mixture or a protein or protein mixture encoded by an exogenous expression construct as further detailed herein above. When the cell has been transduced with multiple different expression constructs each expressing different proteins of interest and/or the cell has been transduced with a single expression construct encoding multiple different proteins of interest, the process for producing a protein or protein mixture of interest as defined herein would result in the production of protein mixtures.

In some instances, the protein may be recovered (i.e. isolated and/or purified), and in others, the cell may be harvested in whole, either of which can be used in a composition. The invention also provides for a composition comprising the modified cell. In case the cell is a microorganism, the cell may be cultured in the appropriate fermentation medium, i.e. a fermentation medium in which the microorganism is capable of producing the proteins of interest. The microorganisms can be cultured by any fermentation process which includes, but is not limited to, batch, fed-batch, cell recycle, and continuous fermentation. In general the fungal strains are grown in fermenters, optionally centrifuged or filtered to remove biomass, and optionally concentrated, formulated, and dried to produce a protein or a multi-protein composition that is a crude fermentation product. Suitable conditions for culturing filamentous fungi are described, for example, in U.S. Pat. No. 6,015,707 and U.S. Pat. No. 6,573,086, which are herein incorporated by reference.

Protein recovering refers to the process of collecting the whole culture medium containing the protein and need not imply additional steps of separation or purification. Proteins produced can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential precipitation or solubilization. Proteins may be retrieved, obtained, and/or used in "substantially pure" form. As used herein, "substantially pure" refers to a purity that allows for the effective use of the protein in any method according to the present invention. For a protein to be useful in further applications, it may be substantially free of contaminants, other proteins and/or chemicals that might interfere or that would interfere with its use in a further application. A "substantially pure" protein, as referenced herein, may be a protein that can be produced by any method (i.e., by direct purification from a natural source, recombinantly, or synthetically), and that has been purified from other protein components such that the protein comprises at least about 80% weight/weight of the total protein in a given composition (e.g., the protein of interest is about 80% of the protein in a solution/composition/buffer), at least about 85%, at least about 90%, at least about 91%, at least about 92%, at least about 93%, at least about 94%, at least about 95%, at least about 96%, at least about 97%, at least about 98%, at least about 99% or 100% weight/weight of the total protein in a given composition.

Further provided is a use of a modified cell as defined herein in a process for producing at least one protein of interest as defined herein.

The invention is further explained in the following examples. These examples do not limit the scope of the invention, but merely serve to clarify.

EXAMPLES

Example 1: Improved Protein Production of M. thermophila C1 Strains: Disrupting the Ubc9 Promoter Region The inventors found an unexpectedly high protein producing Myceliophthora thermophila C1 strain after two rounds of subsequent co-transformation starting with W1L#100.1Δalp1Δchi1Δpyr5 (yielding a second generation transformant) using a specific cellulase expression cassette (as described in EP patent application 2408910). Genetic analysis of the transformant revealed an integration event into the promoter region of the gene annotated as ubiquitin-conjugating enzyme, E2 (ubc9) (NCBI accession number XP_003662268.1, Interpro ID IPR000608, Prosite Accession PS50127, containing the Pfam domain PF00179) represented herein by SEQ ID NO: 1, which likely impairs functional expression. Ubc9 was shown to play a role in SUMOylation of target proteins In order to gain more insight into the high-protein-production phenotype of the second generation transformant, differential gene expression (RNA-seq) analysis was performed with the second generation transformant and compared to W1L#100.1Δalp1Δchi/Δpyr5. Carbon-limited fed-batch cultivations with both strains were performed using glucose as carbon feed. From these cultivations, mycelium samples were taken at 4 hours, 90 hours and 162 hours after starting the feed. From these samples, total RNA was isolated with the SV Total RNA Isolation System (Promega Corporation, USA) using ground mycelium as starting material. Isolated total RNA was subsequently sent for sequencing using the Illumina platform. Paired-end stranded RNA sequencing data was analysed and visualized using a combination of standard tools (TopHat, Cuffdiff) and custom-made scripts. Expression as measured in FPKM (Fragments per Kilobase Million) and obtained from 126 nt long, paired-end Illumina RNA-seq reads (total library size 4.7-8.2M mate-pairs each) is presented in Table 1. The results from the differential gene expression analysis, revealed a downregulation of gene ubc9, a SUMO-conjugating enzyme involved in the SUMO-conjugation pathway. Reduction of expression of ubc9 is consistently shown in all time-points, with reduction levels of 95.4 to 99%, corresponding to a reduction of at least 4.3 fold (at t=4 h).

TABLE 1

FPKM values obtained with differential gene expression analysis using RNA-sequencing.

|  | W1L#100.1Δalp1Δchi1Δpyr5 | Second generation transformant |
|---|---|---|
| 4 hours | 83.0 | 3.8 |
| 90 hours | 126.3 | 1.3 |
| 162 hours | 95.4 | 2.9 |

Example 2: Targeted Disruption of the Ubc9 Gene Promoter Region of M. thermophila C1 Strains To test the effect of the integration event on protein production, the amdS selection marker was inserted at the same locus in a *Myceliophthora thermophila* C1 strain, i.e. inserted in ubc9 promoter region between the nucleotides on position 1257 and 1258 of SEQ ID NO: 1. More in particular the strain used was derived from W1L#100.1ΔalplΔchilΔpyr5. W1L#100.1ΔalplΔchilΔpyr5 is derived from W1L#100.1 (deposited under no CBS122190) by disruption of the alp1 and chit gene as described in WO2010/107303, incorporated herein by reference (more in particular, in Example 5 of WO2010/107303).

Transformants were produced by co-transfection of W1L#100.1 ΔalplΔchilΔpyr5 with an expression cassette encoding Eg2 (represented herein by SEQ ID NO: 4) and a pyr5 selection marker (represented herein by SEQ ID NO: 7). The obtained transformant is denominated W1L#100.1ΔalplΔchilΔpyr5[eg2/pyr5]. Subsequently, the Ubc9-amdS insertion cassette represented by SEQ ID NO: 3 was targeted to the specific ubc9 locus in W1L#100.1ΔalplΔchilΔpyr5[eg2/pyr5] analogous to the procedure to make gene deletions that was described previously by Visser et al. (2011). The amdS insertion cassette was constructed consisting of the acetamidase (amdS) selection marker gene (including its own promoter and terminator sequences) from *Aspergillus nidulans*, flanked by sequences of 1257 and 1380 bp (upstream and downstream flanks, respectively) of the ubc9 insertion site (nucleotide position 1257-1258 of SEQ ID NO: 1). The insertion cassettes further comprise cbh repeats which are not relevant for the present Examples but can be used for optional selection marker sequence removal in future applications. The insertion of amdS occurs upon homologous recombination of the flanking sequences carrying the same sequence as the insertion site in the genome. This way, the amdS selection marker was inserted into the W1L#100.1ΔalplΔchilΔpyr5[eg2/pyr5] genome at the specified locus.

Transformants were screened using colony PCR, which was set up to amplify part of the amdS gene combined with a part of the insertion site. Only when the amdS gene was properly inserted at the correct locus, amplification was possible. This way, transformants carrying a correctly inserted amdS could be distinguished from transformants having the selection marker integrated elsewhere in the genome.

Confirmed transformant strains were grown in microtiter plates and shake flasks to test the effect of the insertion of amdS on extracellular protein production. Improved protein production and secretion was confirmed by visual observation with SDS-PAGE. Subsequent fermentation experiments (carbon-limited fed-batch cultivations using glucose as the carbon feed) further confirmed the improved protein production. Protein concentration measurements with the BCA assay (Pierce BCA Protein Assay kit (ThermoFisher Scientific)) on extracellular protein content showed higher protein production levels of the transformant strain, with protein levels increasing from 15.6 to 35.5 g/L (FIG. 1). In addition, the Qp max was determined for both strains (Table 2). The Qp is the specific protein production rate (gram protein/gram biomass/hour), which was calculated by dividing the total protein production rate (in gram/hour) by the amount of biomass (cell dry weight) present at that time in the reactor. The total protein production rate is calculated from the slope of the total protein produced in time. The Qp max increased from 0.011 g/g/h in the parental strain to 0.015 g/g/h in the ubc9 modified strain.

TABLE 2

Total protein and Qp with and without disruption in the ubc9 promoter region

| Strain | Total protein (g/L) | Qp max (gram protein/ gram biomass/ hour) |
|---|---|---|
| W1L#100.1ΔalplΔchilΔpyr5[eg2/pyr5] | 15.6 | 0.011 |
| W1L#100.1ΔalplΔchilΔpyr5[eg2/pyr5] ubc9::amdS | 35.5 | 0.015 |

Example 3: Improved Heterologous Protein Production with *M. thermophila* C1 Strains: Disrupting the Ubc9 Promoter Region In order to demonstrate that the genetic modification of ubc9 promoter (Pubc9) results in improved production levels of proteins from microorganisms other than *M. thermophila* C1, the Pubc9 mutation—as described in Example 1—was introduced into strain W1L#100.1ΔalplΔchilΔpyr5 expressing the heterologous protein Bxl1 (β-xylosidase) from *Talaromyces wortmanii* W1L#100.1ΔalplΔchilΔpyr5 [TwBxl1/pyr5] and PGII (polygalacturonase) from *Aspergillus niger* (W1L#100.1ΔchilΔpyr5 [AnPGII/pyr5]).

Transformants were produced by co-transfecting a pyr5 selection marker (represented herein by SEQ ID NO: 7) with the expression cassette encoding TwBxl1 or AnPGII in W1 L#100.1ΔalplΔchilΔpyr5, thereby producing transformant W1L#100.1ΔalplΔchilΔpyr5[TwBxl1/pyr5] or W1L#100.1ΔalplΔchilΔpyr5[AnPGII/pyr5]. This expression cassette (represented herein by SEQ ID NO: 6 and 5, respectively) further comprised a chit gene promoter, and the cbh1 terminator sequence, which are commonly used to obtain high expression levels of the corresponding genes (Visser et al., 2011). Subsequently, Ubc9-amdS insertion cassette represented by SEQ ID NO: 3 was targeted to the ubc9 promoter in strains W1 L#100.1ΔalplΔchilΔpyr5 [TwBxl1/pyr5] and W1 L#100.1ΔalplΔchilΔpyr5[AnPGII/pyr5] as further detailed in Example 2.

Transformants were screened using colony PCR, which was set up to amplify part of the amdS gene combined with a part of the insertion site. Only when the amdS gene was properly inserted at the correct locus, amplification was possible. This way, a transformant carrying a correctly inserted amdS could be distinguished from transformants having the selection marker integrated elsewhere in the genome.

Figure 2:
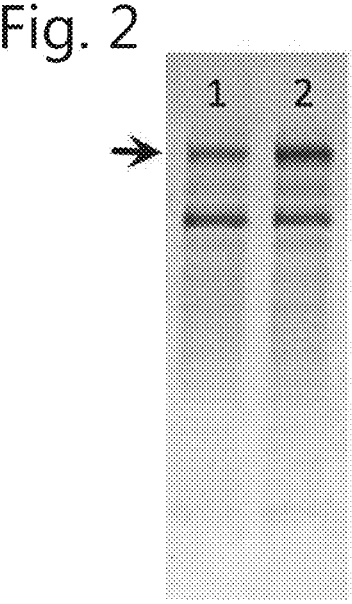
FIG. 2. SDS-PAGE analysis of microtiterplate broth of:
W1L#100.1Δalp1Δchi1Δpyr5[Twbxl1/pyr5] (lane 1); and,
W1L#100.1Δalp1Δchi1Δpyr5[TwBxl1/pyr5]ubc9- (lane 2)
TwBxl1 protein indicated by arrow head.
Figure 3:
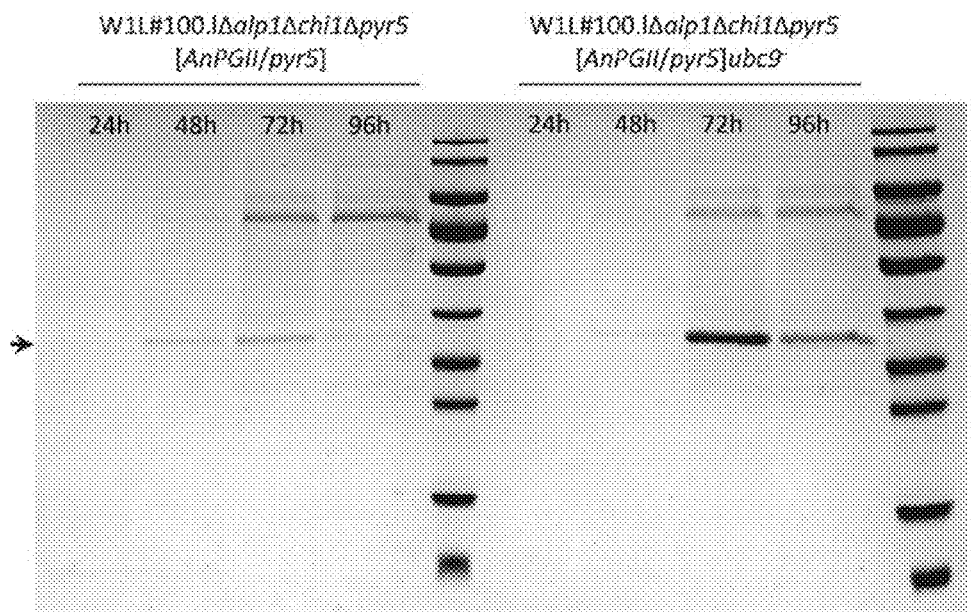
FIG. 3. SDS-PAGE analysis of shake flask cultures of:
W1L#100.1Δalp1Δchi1Δpyr5[AnPGII/pyr5]; and,
W1L#100.1Δalp1Δchi1Δpyr5[AnPGII/pyr5]ubc9-Arrow head indicates AnPGII protein.
Figure 4:
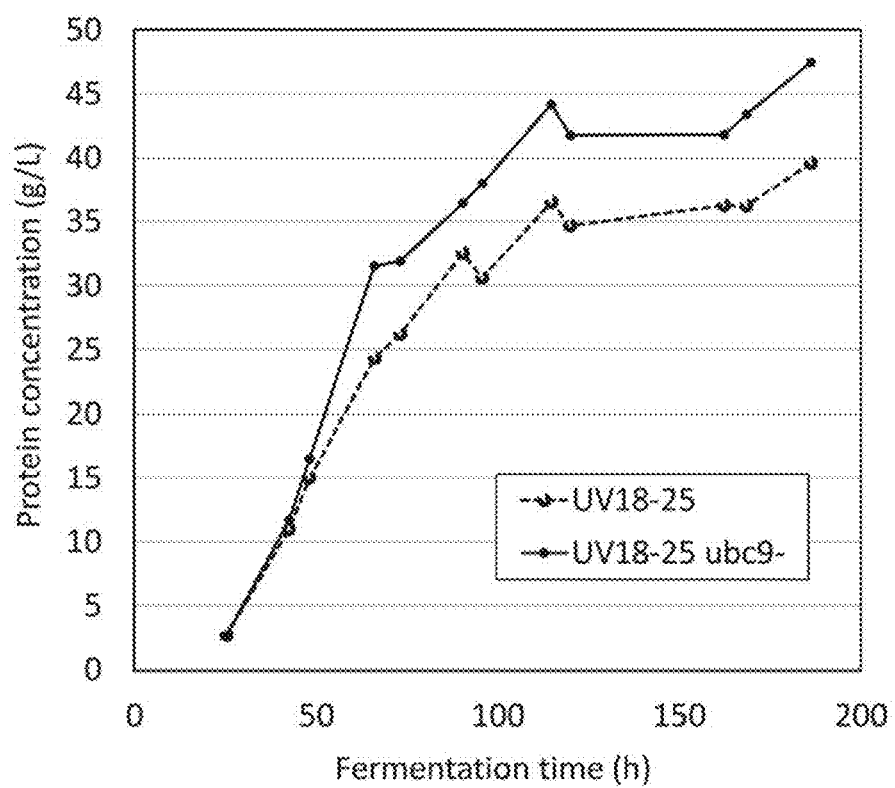
FIG. 4. Total protein concentration of UV18-25 and UV18-25ubc9- during fermentation in time (h).

Confirmed transformant strains were grown in microtiter plates and shake flasks to test the effect of the insertion of amdS on extracellular protein production. Improved protein production and secretion was confirmed by visual observation with SDS-PAGE (FIGS. 2 and 3).

Example 4: Improved Protein Production of *M. thermophila* HC C1 Strains: Disrupting the Ubc9 Promoter Region In order to demonstrate that the genetic modification of Pubc9 (the promoter region of ubc9) in another *M. thermophila* lineage also results in improved production levels, the Pubc9 mutation—as described in Example 1—was introduced into HC-strain UV18-25.

Introducing the amdS selection marker represented by SEQ ID NO: 3 into the ubc9 promoter region in strain UV18-25 is further detailed in Example 2.

Transformants were screened using colony PCR, which was set up to amplify part of the amdS gene combined with a part of the insertion site. Only when the amdS gene was properly inserted at the correct locus, amplification was possible. This way, transformants carrying a correctly inserted amdS could be distinguished from transformants having the selection marker integrated elsewhere in the genome.

A confirmed transformant strain was grown in microtiter plates and shake flasks to test the effect of the insertion of amdS on extracellular protein production. Improved protein production and secretion was confirmed by visual observation with SDS-PAGE.

The confirmed transformant strain was tested in fermentation experiments (as described in Example 2) to confirm the improved protein production. Protein concentration measurements with the BCA assay (as described in Example 2) on extracellular protein content showed higher protein production levels of the transformant strain, with protein levels increasing from 39.6 to 47.5 g/L. In addition, the maximum specific protein production rate (Qp max) was determined for both strains, as described in Example 2 (Table 3).

TABLE 3

Total protein concentration (g/L) and Qp max (g/g/h) obtained from Labfors (2.5 L) fermentations

|  | Total protein (g/L) | Qp max (gram protein/ gram biomass/ hour) |
|---|---|---|
| UV18-25 | 39.6 | 0.016 |
| UV18-25 ubc9::amdS | 47.5 | 0.016 |

Figure 5:
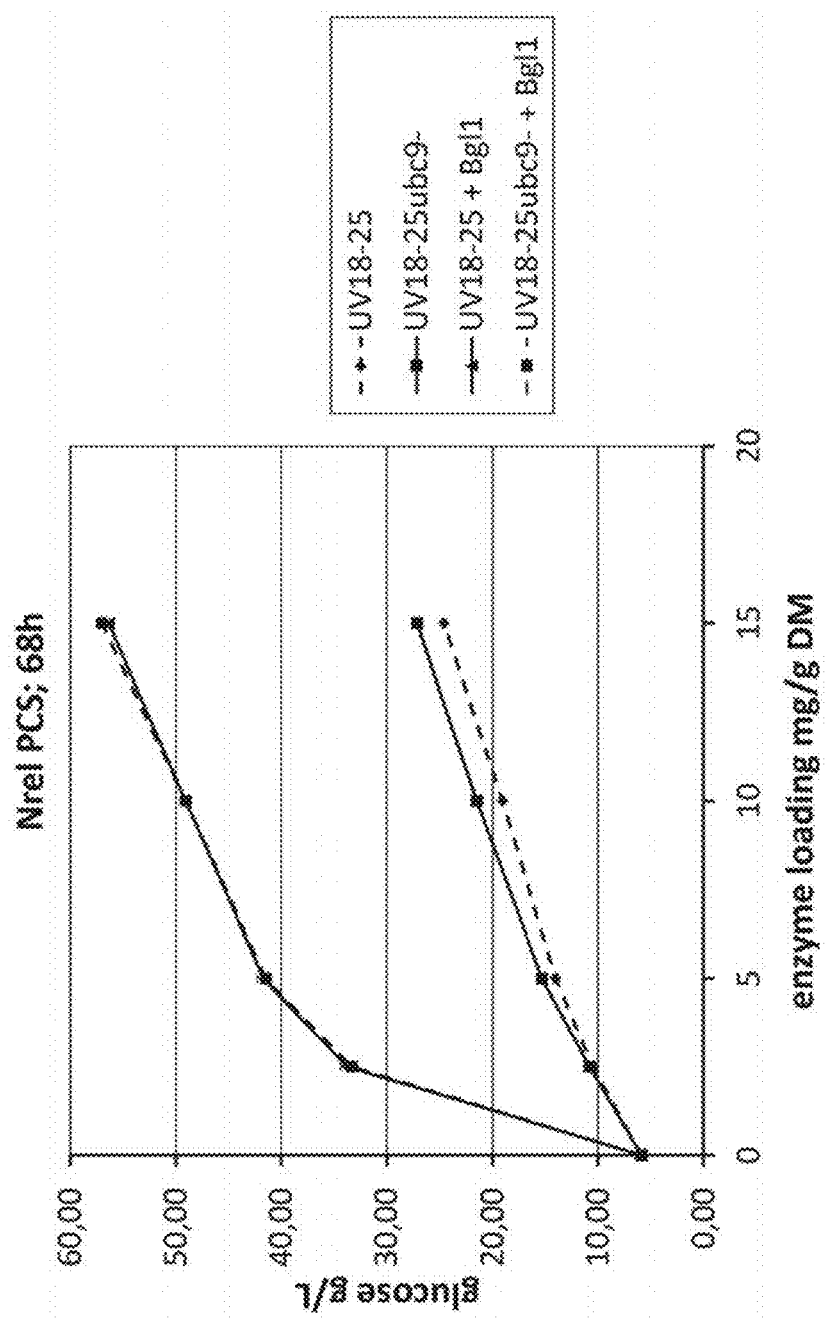
FIG. 5. Glucose release after 68 h of incubation of the end-of-fermentation broth of UV18-25 and UV18-25ubc9- on NREL PCS substrate with and without the addition of Bgl1 to the enzyme mixture.

Enzyme cocktails from strains UV18-25 and a UV18-25 ubc9::amdS were tested for saccharification efficiency. NREL pre-treated corn stover (Schell et al., J Appl Biochem Biotechnol, 105:69-86, 2003) was used as a substrate. Saccharification reactions were carried out in a total volume of 10 mL in 50 mL Greiner tubes using the substrate at a dry matter content of 20%. Saccharification reactions were performed at pH 5 using an acetate buffer at a final concentration of 100 mM. A predetermined amount of sodium hydroxide was added to each reaction to set the pH at 5. An additional reaction (15 mg/g) was included to monitor the pH every 24 hours. When the pH of this additional reaction deviated by more than 0.1 pH units, 2M NaOH was added to correct the pH to its initial starting pH. The volume needed to adjust the pH was subsequently added to the other reaction tubes and mixed immediately. Sodium azide was dosed at 0.02% (w/w). Enzyme mixtures were tested at enzyme loadings of 2.5-5-10 and 15 mg/g DM (dose-response). Purified Bgl1 from $M.$ $thermophila$ C1 (SEQ ID NO: 16) was added to each reaction (10% of the baseline loading). Enzyme loadings were applied using BCA determined values described above. The reactions were incubated at 52° C. at 300 rpm. After 24, and 68 h, 0.2 ml samples were taken and filtrated using a micro plate (pvdf), followed by analysis of the supernatants. Glucose concentrations were measured using GOPOD assay kit (Megazyme, Co. Wicklow, Ireland). All experiments have been performed in duplicate. The saccharification efficiency of the protein mixtures of UV18-25 ubc9::amdS is shown in FIG. 5.

TABLE 4

Sequence overview for SEQ ID ONs 1-7

| SEQ ID NO | Name | Specific regions Name | position |
|---|---|---|---|
| 1 | ubc9 gene with flanking sequence | 5'UTR | 1070-1301 |
|  |  | ubc9 ORF | 1302-1994 |
|  |  | 3'UTR | 1995-2195 |
|  |  | Integration site | 1257-1258 |
| 2 | Protein sequence Ubc9 |  |  |
| 3 | ubc9-amdS insertion cassette | ubc9 upstream flank | 7-1263 |
|  |  | cbh repeat | 1269-1860 |
|  |  | amdS | 1871-4592 |
|  |  | cbh repeat | 4594-5184 |
|  |  | ubc downstream flank | 5193-6572 |
| 4 | Expression cassette eg2 | Pchi-ext: | 31-1074 |
|  |  | Pchi: | 1075-1849 |
|  |  | eg2: | 1850-3467 |
|  |  | Tcbh: | 3468-4483 |
| 5 | Expression cassette AnPG11 | Pchi-ext | 4-1047 |
|  |  | 'Pchi | 1048-1822 |
|  |  | AnPG11 | 1823-2913 |
|  |  | Tcbh' | 2920-3935 |

TABLE 4-continued

Sequence overview for SEQ ID ONs 1-7

| SEQ ID NO | Name | Specific regions Name | position |
|---|---|---|---|
| 6 | Expression cassette TwBxl1 | Pchi-ext | 31-1074 |
| | | 'Pchi | 1075-1848 |
| | | TwBxl1 | 1850-4245 |
| | | Tcbh' | 4252-5267 |
| 7 | pyr5 selection marker | pyr5 | 1173-1877 |

Example 5: Disruption of the Ubc9 Gene Promoter Region of M. thermophila C1 Strains Expressing Heterologous Glucoamylase Transformants were produced by co-transfection of strains W1L#100.1 Δalp1Δchi1Δpyr5 and strain UV18#100.fΔalp1Δpyr5 with an expression cassette encoding Trichoderma reesei glucoamylase (designated as "DP1"), of which the DNA coding sequence was modified for expression in C1 strains (represented herein by SEQ ID NO: 17 and SEQ ID NO: 18, respectively), and a pyr5 selection marker (represented herein by SEQ ID NO: 7). The expression cassette used for the W1L#100.lΔalp1Δchi1Δpyr5 strain included a chit promoter sequence (SEQ ID NO: 51) and the expression cassette used for the UV18#100.fΔalp1Δpyr5 strain included a cbh1 promoter sequence (SEQ ID NO: 52). Obtained transformants were screened for glucoamylase activity using the β-amylase assay kit (Betamyl-3) from Megazyme (Co. Wiklow, Ireland). The transformants with the highest glucoamylase activity were selected and denominated W1L#100.lΔalp1Δchi1Δpyr5[DP1/pyr5] and UV18#100.fΔalp1Δpyr5[DP1/pyr5], respectively. Subsequently, the ubc9 promoter region in these transformants was modified analogous to that described in Example 2.

After confirming that the ubc9 promoter region was modified by colony PCR (as described in Example 2), the modified strains and their glucoamylase expressing parental strains were grown in Minifors (1 L) or Labfors (2.5 L) fermenters in carbon-limited fed-batch cultivations using glucose as the carbon source to test for extracellular glucoamylase production. Glucoamylase activity assays were performed using p-Nitrophenyl α-D-glucopyranoside (pNPG; Sigma N-1377) as a substrate. The levels of glucoamylase produced by M. thermophila C1 were calculated by converting glucoamylase units (GAU) measured with the pNPG assay into gram glucoamylase per liter (g/L). To this end, a conversion factor was determined by performing the same pNPG assay on a sample of T. reesei-produced glucoamylase for which the protein concentration was known. This conversion factor was subsequently used to convert GAU measured in M. thermophila cultures to glucoamylase concentrations. The ubc9 modified M. thermophila strains showed higher glucoamylase production levels (Tables 5B and 6B).

Total protein concentrations (measured with the BCA assay as described in Example 2) were higher from the W1L#100.lΔalp1Δchi1Δpyr5[DP1/pyr5] ubc9 modified strain (Table 5A). Total protein levels from the UV18#100.fΔalp1Δpyr5[DP1/pyr5] ubc9 modified strain did not increase in Minifors (1 L) fermentations, but did show increased protein levels in Labfors (2.5 L) fermentations (Table 6A). In addition, the Qp max were calculated (as described in Example 2) which are reported in Table 7.

TABLE 5A

Total protein concentrations produced with strain W1L#100.lΔalp1Δchi1Δpyr5 expressing DP1 with and without ubc9 gene promoter disruption

| | 1 liter* | 2.5 liter |
|---|---|---|
| W1L#100.lΔalp1Δchi1Δpyr5 [DP1] | 6.59 g/L | 20.09 g/L |
| W1L#100.lΔalp1Δchi1Δpyr5 [DP1] ubc9::amdS | 25.55 g/L | 26.57 g/L |

*refers to fermentation scale used for evaluation of the strains

TABLE 5B

Glucoamylase concentrations produced with strain W1L#100.lΔalp1Δchi1Δpyr5 expressing DP1 with and without ubc9 gene promoter disruption

| | 1 liter | 2.5 liter |
|---|---|---|
| W1L#100.lΔalp1Δchi1Δpyr5 [DP1] | 4.3 g/L | 16.4 g/L |
| W1L#100.lΔalp1Δchi1Δpyr5 [DP1] ubc9::amdS | 19.2 g/L | 25.6 g/L |

TABLE 6A

Total protein concentrations produced with strain UV18#100.fΔalp1Δpyr5 expressing DP1 with and without ubc9 gene promoter disruption

| | 1 liter | 2.5 liter |
|---|---|---|
| UV18#100.f Δalp1Δpyr5 [DP1] | 53.37 | 72.61 |
| UV18#100.f Δalp1Δpyr5 [DP1] ubc9::amdS | 52.08 | 80.01 |

TABLE 6B

Glucoamylase concentrations produced with strain UV18#100.fΔalp1Δpyr5 expressing DP1 with and without ubc9 gene promoter disruption

| | 1 liter | 2.5 liter |
|---|---|---|
| UV18#100.f Δalp1ΔΔpyr5 [DP1] | 17.0 | 33.1 |
| UV18#100.f Δalp1ΔΔpyr5 [DP1] ubc9::amdS | 24.7 | 34.4 |

TABLE 7

Total protein concentration (g/L) and Qp max
(g/g/h) based on Labfors (2.5 L) fermentations

| Strain | Total protein (g/L) | Qp max (gram protein/ gram biomass/ hour) |
|---|---|---|
| W1L#100.1Δalp1Δchi1Δpyr5 [DP1] | 20.09 | 0.004 |
| W1L#100.1Δalp1Δchi1Δpyr5 [DP1] ubc9::amdS | 26.57 | 0.006 |
| UV18#100.f Δalp1Δpyr5 [DP1] | 72.61 | 0.017 |
| UV18#100.f Δalp1Δpyr5 [DP1] ubc9::amdS | 80.01 | 0.017 |

Example 6: Targeted Disruption of the Ubc9 Gene Promoter Region of M. thermophila C1 Strains Expressing Heterologous Phytase In order to demonstrate that the genetic modification of Pubc9 (the promoter region of ubc9) also results in improved production levels of a heterologous phytase, the Pubc9 mutation was introduced—as described in Example 2—into C1 strains W1L#100.1Δalp1Δchi1Δpyr5 and UV18#100.fΔalp1Δpyr5 expressing a *Buttiauxella* sp phytase variant (protein SEQ ID NO: 21).

Transformants were produced by co-transfection of strains W1L#100.1 Δalp1Δchi1Δpyr5 and UV18#100.fΔalp1Δpyr5 with an expression cassette encoding phytase (represented herein by SEQ ID NO: 53 and SEQ ID NO: 54, respectively) and a pyr5 selection marker (represented herein by SEQ ID NO: 7). The expression cassette used for the W1L#100.1 Δalp1Δchi1Δpyr5 strain included a chit promoter sequence (SEQ ID NO: 51) and the expression cassette used for the UV18#100.fΔalp1Δpyr5 strain included a cbh1 promoter sequence (SEQ ID NO: 52). The obtained transformants having elevated phytase activity greater than the untransformed parent are denominated W1 L#100.1Δalp1Δchi1Δpyr5[phytase/pyr5] and UV18#100.fΔalp1Δpyr5[phytase/pyr5], respectively. Subsequently, the ubc9 promoter region in these transformants was modified analogous to that described in Example 2.

Confirmed ubc9 modified strains and their phytase expressing parental strains were grown in fermenters (carbon-limited fed-batch cultivations with both strains were performed using glucose as carbon feed) to test the effect of the ubc9 promoter modification on extracellular phytase production.

Figure 6:
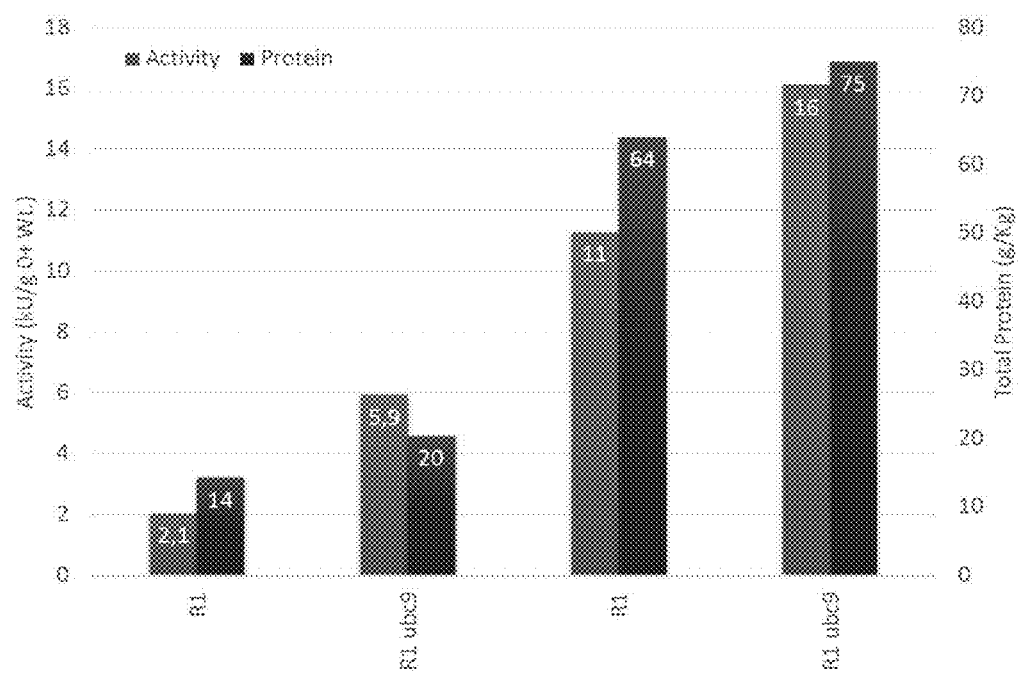
FIG. 6. Phytase activity measurements demonstrating effect of disruption of ubc9 gene promoter in C1 strains
FIG. 7. Diagram of pLH937, described in Example 8.
Figure 7:
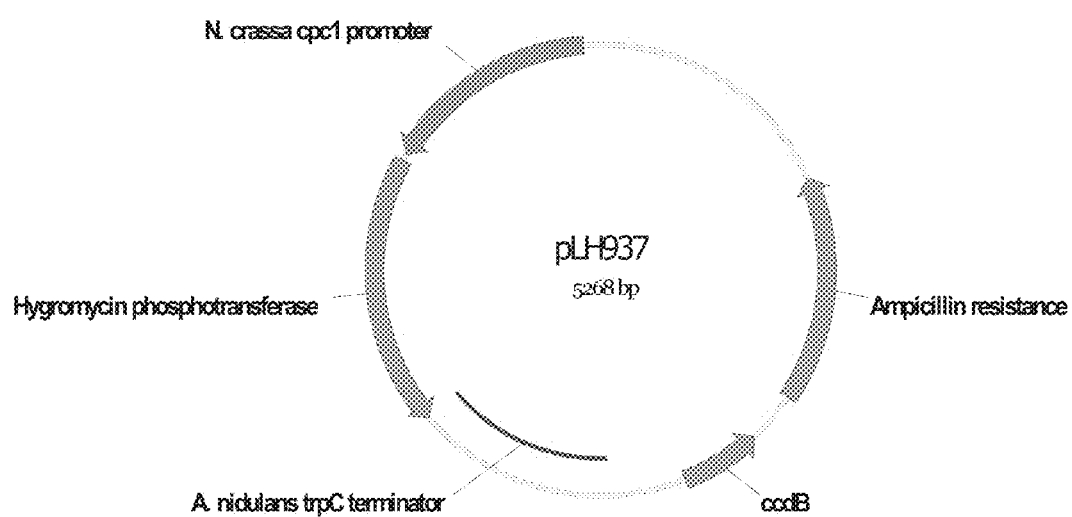

Phytase activity measurements (US2015/0030717, incorporated herein by reference) showed higher activity levels of the ubc9 modified strains, with activity levels increasing from 2.1 to 5.9 kU/g for W1L#100.1Δalp1Δchi1Δpyr5 [phytase/pyr5] and from 11.3 to 16.1 kU/g for UV18#100.fΔalp1Δpyr5[phytase/pyr5] (FIG. 6). In addition, total protein levels were higher from the ubc9 modified strains, with extracellular protein levels increasing from 14 to 20 g/Kg for W1 L#100.1Δalp1Δchi1Δpyr5[phytase/pyr5] and from 64 to 75 g/Kg for UV18#100.fΔalp1Δpyr5 [phytase/pyr5] (FIG. 6).

Example 7: Targeted Disruption of the Ubc9 Gene Promoter Region of *Aspergillus niger* Strains Overexpressing Heterologous Polygalacturonase II

*Aspergillus niger* used in this study are derived from N402 (Bos et al, 1988). *A. niger* strains expressing pGpdA-pgaII$^{C1}$ were obtained by co-transfection of strain AB4.1, a pyrG$^-$ derivative of N402 (van Hartingsveldt et al., 1987) with 5 μg pAB4.1 (van Hartingsveldt et al., 1987) and 50 μg pGpdA-pgaII$^{C1}$. Expression vector pGpdA-pgaII$^{C1}$ (SEQ ID NO: 23) contains the coding sequence for polygalacturonase II from *A. niger* which was codon optimized for expression in *M. thermophila* C1 (SEQ ID NO: 24; protein SEQ ID NO: 25), and the commonly used GpdA promoter to drive gene expression. Transfection of *A. niger* was performed as described (Arentshorst et al., 2012). Transformants were purified by two rounds of purification on selective minimal medium (Bennet and Lasure, 1991). After purification, individual transformants were grown in microtiter plate well (200 μl minimal medium) and the medium was assayed for galacturonase activity using the PAHBAH assay (see below). Strains showing PgaII expression were grown on complete medium (Arentshorst et al., 2012) and incubated for 4-5 days before conidiospore isolation. Spores were counted using a Biorad Cell counter and stored at 4° C. in 0.9% NaCl. Spore suspensions were used to inoculate shake flask cultures (50 ml minimal medium in 300 ml Erlenmeyer flasks) at a density of 1.0×10$^6$ spores/ml and grown for 36 h at 37° C. at 250 rpm.

Ubc9-promoter (gene identifier An04g01350 in AspGD) knock-in strains were obtained by transfection with amdS selection of the ubc9 knock-in cassette (SEQ ID NO: 26) to *A. niger* strains AN[PGAII]_HIGH and AN[PGAII]_LOW. The knock-in fragment was designed such that the amdS selection marker was introduced 45 base pairs upstream of the ubc9 start-ATG, which is similar to the strategy used to knock in the amdS selection marker in *M. thermophila*. The knock-in cassette contains the amdS marker flanked by 956 bp of the 5' ubc9 upstream region and 983 bp of the ubc9 upstream and coding region. The 5863 bp fragment was used for transfection of strains AN[PGAII]_HIGH and AN[PGAII]_LOW. Transformant strains were selected on media for amdS selection as described in Arentshorst et al., 2012. Transformants were purified twice on selective minimal acetamide plates, before selected strains were grown on complete medium to obtain spores to inoculate liquid cultures.

Genomic DNA was isolated as described previously (Meyer et al., 2010) and used in a diagnostic PCR using primers ubc9P1f and ubc9P4r. PCR was performed with Phire Hot Start II DNA polymerase or Phusion DNA polymerase (Thermo Scientific). ubc9P1f (GATAGTGCT-TAGCGACACCCG; SEQ ID NO: 27) anneals to the amdS marker and ubc9P4r (TCGGCCACAAATCTCAGTGA; SEQ ID NO: 28) anneals to the 3' ubc9 region. Successful integration of the knock-in fragment in the ubc9 promoter is expected to result in a PCR fragment of 2222 bp, while no product is formed when the fragment inserts ectopically.

Southern blot analysis was performed according to (Sambrook and Russell 2001). α-$^{32}$P-dCTP-labelled probes were synthesized using the Decalabel DNA labelling kit (Thermo Scientific, Waltham, Mass.), according to the instructions of the manufacture. Genomic DNA of *A. niger* strains was digested with BamHI and labeled with a 1000 nucleotide probe covering the ubc9 coding region. Restriction enzymes were obtained from Thermo Scientific and used according to instructions of the manufacturer.

Bioreactor cultivations were performed as described before (Jorgensen et al., 2010; Nitsche et al., 2012, using 0.75% (w/v) glucose as a carbon source.

The PAHBAH non-reducing sugar assay was performed to determine the relative polygalacturonase activity using polygalacturonic acid as a substrate (as described by M.

Lever, 1972). Enzyme activity of the samples is defined as the amount of galacturonic acid per liter that is released in 5 minutes divided by the incubation time per liter reaction volume (see formula). Enzyme activity is shown in units per gram protein (U/g). Enzyme activity is determined on diluted samples which were within the range of the standard curve (0-2 mM galacturonic acid).

$$\text{Enzymatic activity} = \frac{X * Vr * De * 1000}{Ve * T}$$

X=mmol galacturonic acid per liter
Vr=reaction volume in liters
De=enzyme dilution before adding to reaction mix
Ve=enzyme volume added to reaction mix in ml
Ec=enzyme/protein concentration in stock solution in mg/ml
T=incubation time Medium samples from *A. niger* transformants obtained after co-transfection of pAB4.1 with pGpdA-pgaII$^{C1}$ were assayed for endo-polygalacturonase activity after cultivation in microtiter plates using the PAHBAH non-reducing sugar assay and PGA as a substrate. 12 transformants with activities at least 3-fold higher compared to the untransformed strains were selected and grown again in shake flask cultures for a reliable quantitative activity measurement. Based on these activity measurements two strains were selected, An[PgaII]_high (110±10 AU) and An[PgaII]_low (30±3 AU), which displayed activities on PGA well above the parental strain N402 (4±1 AU). Strains An[PgaII]_high and An[PgaII]_low were selected as a high polygalacturonases and low galacturonase producing *A. niger* strains and used for subsequent experiments.

Strain An[PgaII]_high and strain An[PgaII]_low were transformed with the ubc9::amdS promoter knock-in construct and transformants able to grow on acetamide plates were selected and purified. Genomic DNA of transformants was isolated and analyzed by diagnostic PCR and Southern blot to identify transformants in which the ubc9::amdS promoter knock-in fragment was integrated at the intended site. Two transformants in the An[PgaII]_high background (An[PgaII]_high ubc9::amdS #8 and #17) and one transformant in the An[PgaII]_low background (An[PgaII]_low ubc9::amdS #1) were found to contain the fragment at the expected site and did not contain additional inserts.

The selected strains An[PgaII]_high and An[PgaII]_low and derivatives An[PgaII]_high ubc9::amdS #8 and #17 and An[PgaII]_low ubc9::amdS #1 respectively, were grown in shake flask cultures as described before and assayed for endo-polygalacturonase activity using the PAHBAH assay.

The relative non-reducing activity on PGA of the five strains are given in Table 8. Enzyme production with cultivation of An[PgaII]_high and derivative An[PgaII]_high ubc9::amdS #17 in bioreactors is shown in Table 9.

TABLE 8

Relative non-reducing activity on PGA in culture medium samples of selected transformants after shake flask cultivation (48 h, 30° C.)

| Strain | enzyme activity (AU) | Fold-increase compared to parental strain |
|---|---|---|
| An[PgaII]_high | 184 ± 31 | n.a. |
| An[PgaII]_high ubc9::amdS #8 | 186 ± 28 | 1.01 |
| An[PgaII]_high ubc9::amdS #17 | 179 ± 27 | 0.97 |
| An[PgaII]_low | 30.2 ± 10.4 | n.a. |
| An[PgaII]_low ubc9::amdS #1 | 32.3 ± 12.5 | 1.07 |

TABLE 9

Relative non-reducing activity on PGA in culture medium samples of selected transformants during bioreactor cultivation (pH 3.0, 30° C.) mid-exponential growing cells

| Time point* | An[PgaII]_high_1 BR_JR1 | An[PgaII]_high_2 BR_JR2 | An[PgaII]_high Ubc9::amdS #17_1 BR_JR3 | An[PgaII]_high Ubc9::amdS #17_2 BR_JR4 |
|---|---|---|---|---|
| 1 | 220 | 250 | 260 | 260 |
| 2 | 300 | 240 | 260 | 260 |

*to be able to compare different cultures, samples from the bioreactor were taken after addition of approximately 26 ml (time point 1) or 30 ml (time point 2) of base addition. The alkali addition is linear with the biomass accumulation.

Example 8. Disruption of the Ubc9 Promoter in *Trichoderma reesei*

A plasmid, pLH937 (SEQ ID NO: 29), was constructed comprising the following DNA segments:

1. A bacterial vector including the *E. coli* ccdB gene, an ampicillin resistance gene and origin of replication for selection and amplification in *E. coli*.

2. A hygromycin phosphotransferase open reading frame operably fused to the *Neurospora crassa* cpc1 promoter and *A. nidulans* trpC terminator.

Three different Cas9 target sites in the *Trichoderma reesei* ubc9 promoter were selected. These were close to the insertion site that was used in the above Examples with *Myceliophthora thermophila* (C1).

Target site 1:
(SEQ ID NO: 30)
GCAGTTCGACGCTTACCCACCGG

-continued

Target site 2:
(SEQ ID NO: 31)
CGACGCTTACCCACCGGGTGAGG

Target site 3:
(SEQ ID NO: 32)
GCGCGACTACCATCACGTCTCGG

In each case, the first 20 nucleotides represent the protospacer region recognized by Cas9 and the last three nucleotides are the PAM (protospacer adjacent motif). Guide RNAs for assembly with Cas9 were generated based on these target sequences.

A *Trichoderma reesei* strain that secretes an engineered variant (BP17) of a *Buttiauxella* sp. phytase (SEQ ID NO: 33) was used in these experiments. This strain had deletions of the four major secreted cellulase genes (cbh1, cbh2, egl1 and eg/2) as well as a deletion of an endo glucosaminidase gene to prevent deglycosylation of secreted proteins. Strain construction is described in US 2015/0030717A1, Examples 1 and 2. Protoplasts of this strain were prepared using the methods described in US 2015/0030717, incorporated herein by reference.

Co-Transformation of Cas9.RNP Complex and Plasmid pLH937 into *Trichoderma reesei* Protoplasts Cas9 protein was individually mixed with each of the three different guide RNAs and incubated in buffer to allow assembly of Cas9.RNP complexes. Polyethylene glycol (PEG)-mediated transformation of *T. reesei* protoplasts was performed as described in WO2016100568A1 (incorporated herein by reference) to enable uptake of Cas9.RNP and plasmid DNA.

25 ul Cas9.RNP, 3 ul pLH937 plasmid (0.3 ug/uL), 1.2 ul Lipofectamine® CRISPR-MAX Transfection Reagent (Thermo Fisher) were mixed and added to the protoplasts for uptake. After the transformation procedure protoplasts were plated in an overlay of Vogel's agar medium (with 1.1M sorbitol, 2% glucose and 50 ug/mL hygromycin B) poured over solidified Vogel's agar medium (with 1.1M sorbitol and 20% glucose but without hygromycin).

Transformed colonies that arose on the hygromycin selection plates were transferred onto non-selective Vogel's agar without sorbitol or hygromycin and incubated for 4 days at 30 C. The colonies were then passaged twice on selective Vogel's agar with 50 ug/mL hygromycin. Those transformant colonies that grew well were considered to have a stable hygromycin-resistant phenotype. It was expected that many of these stable transformants would have pLH937, or some fragment(s) thereof, integrated at the cas9 target site in the promoter of the ubc9 gene. Genomic DNA was isolated from transformants. PCR was performed using primers nik1 2 kb F (5'-gccatgaacctcaccacacag; SEQ ID NO: 34) and nik1 2 kb R(5'-cggcgtggccctgttctcgag; SEQ ID NO: 35) to amplify a 2 kb region of the *T. reesei* nik1 locus. Agarose gel electrophoresis confirmed that all samples contained gDNA of sufficient quantity and quality to act as template in PCR.

PCR was performed using primers 3078 (5'-aagagatctctgccctcccaggg; SEQ ID NO: 36) and 3079 (5'-gtgatggccggcttccagg; SEQ ID NO: 37) to amplify the promoter region of ubc9 spanning the cas9 target sites. PCR was with Stratagene PfuUltra II Fusion HS DNA polymerase (Agilent, Santa Clara, Calif.) according to the manufacturer's directions at an annealing temperature of 50 C and an extension time of 1 minute. Using these conditions it was expected that no PCR product would be obtained if there was a large insert at the cas9 target site in the ubc9 promoter. Those transformants that gave a PCR product of the size expected for the wild-type ubc9 locus were eliminated from further analysis. All transformants described below gave no PCR product suggesting that they all have the HygR vector inserted at the target site. PCR was performed using primers 3078 and 3145 (5'-ctttgccctcggacgagtgct; SEQ ID NO: 38) to amplify between the flanking region of the ubc9 promoter and 5' end of the hygromycin phosphotransferase (HygR) gene. PCR was performed at an annealing temperature of 50 C and an extension time of 3 minutes. A PCR product would only be obtained if the HygR vector was inserted at the target site in the ubc9 promoter. Using genomic DNA as template the following transformants showed an obvious PCR product; 3140-12, 3140-34, 3141-11, 3141-25, 3141-34, 3142-15, 3142-34, 3140-2, 3140-5 and 3141-1.

PCR was performed using primers 3078 and 3146 (5'-ctgaactcaccgcgacgtctgtc; SEQ ID NO: 39) to amplify between the flanking region of the ubc9 promoter and 3' end of the HygR gene. PCR was performed at an annealing temperature of 50 C and an extension time of 3 minutes. A PCR product would only be obtained if the HygR vector was inserted at the target site in the ubc9 promoter. Using genomic DNA as template the following transformants showed an obvious PCR product; 3140-31, 3141-15, 3141-35, and 3142-12.

PCR was performed with primers 3078 and 3148 (5'-gtgtgcgacagtgcgcgtcc; SEQ ID NO: 41) to amplify between the flanking region of the ubc9 promoter and the *N. crassa* cpc1 promoter. Using genomic DNA from transformant 3140-15 as template, an annealing temperature of 50 C and an extension time of 2 minutes a DNA fragment of approximately 3.5 kb was amplified. A PCR product would only be obtained if the HygR vector was inserted at the target site in the ubc9 promoter. This amplified DNA fragment was sequenced in one direction using primer 3078 as sequencing primer. Sequence analysis confirmed that pLH937 DNA was inserted at the Cas9 target site in the ubc9 promoter. In summary, PCR analysis verified that 15 of the 25 transformants shown in Table 12 had pLH937 DNA inserted into the ubc9 promoter region. The other transformants presumably also had pLH937 DNA inserted into the ubc9 promoter region but, because the extent or arrangement of the inserted pLH937 DNA was unknown, this could not be verified by PCR.

Transformants and the parental strain were cultured for 4 days at 28 C in triplicate in 24 well slow-release microtiter plates incorporating 20% lactose in the plate (WO2014047520A1) and using *Trichoderma* defined medium with 2.5% glucose/sophorose (EP1545217B1) as the liquid medium. Phytase activity was measured in supernatants using pNPP as substrate (US2015/0030717, incorporated herein by reference). The assay was run as an end-point assay and absorbance was read at 405 nm. The average absorbance from triplicate cultures of each strain is shown in Table 10 with the associated standard deviation.

TABLE 10

Phytase activity of *Trichoderma reesei* transformants

| Transformant | Average absorbance | Standard Deviation |
|---|---|---|
| 3140-12 | 0.4 | 0.022 |
| 3140-15 | 0.544 | 0.027 |
| 3140-17 | 0.394 | 0.009 |
| 3140-18 | 0.456 | 0.028 |
| 3140-31 | 0.397 | 0.006 |
| 3140-33 | 0.455 | 0.007 |

TABLE 10-continued

Phytase activity of *Trichoderma reesei* transformants

| Transformant | Average absorbance | Standard Deviation |
|---|---|---|
| 3140-34 | 0.467 | 0.014 |
| 3140-35 | 0.407 | 0.025 |
| 3141-11 | 0.309 | 0.061 |
| 3141-13 | 0.343 | 0.02 |
| 3141-15 | 0.476 | 0.019 |
| 3141-20 | 0.447 | 0.011 |
| 3141-25 | 0.418 | 0.01 |
| 3141-34 | 0.507 | 0.018 |
| 3141-35 | 0.361 | 0.026 |
| 3142-12 | 0.501 | 0.029 |
| 3142-15 | 0.206 | 0.005 |
| 3142-25 | 0.359 | 0.017 |
| 3142-28 | 0.448 | 0.011 |
| 3142-32 | 0.429 | 0.027 |
| 3142-34 | 0.478 | 0.028 |
| 3142-35 | 0.39 | 0.022 |
| 3140-2 | 0.397 | 0.014 |
| 3140-5 | 0.351 | 0.006 |
| 3141-1 | 0.399 | 0.013 |
| Parent strain | 0.474 | 0.004 |

One transformant, 3140-15, clearly produced more secreted phytase activity than the parent strain. This transformant, as well as transformant 3142-32 and the parent strain, were again grown in triplicate in microtiter plates and the phytase activity in culture supernatant determined (see Table 11). Again, transformant 3140-15 produced approximately 15% more phytase than the parent strain.

TABLE 11

Phytase activity of *Trichoderma reesei* transformants

| Transformant | Average absorbance | Standard Deviation |
|---|---|---|
| Parent strain | 0.512 | 0.009 |
| 3142-32 | 0.494 | 0.015 |
| 3140-15 | 0.588 | 0.038 |

The invention claimed is:

1. A modified *Myceliophthora thermophila* cell having increased acetyl esterase, aminopeptidase, amylase, arabinase, arabinofuranosidase, carboxypeptidase, catalase, cellobiohydrolase, cellulase, chitinase, chymosin, cutinase, deoxyribonuclease, epimerase, esterase, a-galactosidase, β-galactosidase, a-glucanase, glucan lyase, endo-β-glucanase, glucoamylase, glucose oxidase, a-glucosidase, β-glucosidase, glucuronidase, hemicellulase, hexose oxidase, hydrolase, invertase, isomerase, laccase, lipase, lyase, lytic polysaccharide monooxygenase, mannosidase, oxidase, oxidoreductase, pectate lyase, pectin acetyl esterase, pectin depolymerase, pectin methyl esterase, pectinolytic enzyme, peroxidase, phenoloxidase, phytase, polygalacturonase, protease, rhamno-galacturonase, ribonuclease, thaumatin, transferase, transport protein, transglutaminase, xylanase, or β-xylosidase protein production, wherein said cell has been modified by a genetic modification of the ubc9 gene to reduce Ubc9 protein production and/or activity, wherein the ubc9 gene has a wild type counterpart encoding an Ubc9 protein that comprises:

(i) a first motif of RLQEERKQWRKDHPFGF (SEQ ID NO: 42) or a version thereof having a T or H instead of Q at position 3 of SEQ ID NO: 42, a K instead of Q at position 8 of SEQ ID NO: 42, and/or an A instead of G at position 16 of SEQ ID NO: 42; and (ii) a second motif of KPPKCKFTPPLFHPNVYPSGTV-CLSIL (SEQ ID NO:43) or a version thereof having a V instead of C at position 5 of SEQ ID NO:43, a V, P, or D instead of T at position 8 of SEQ ID NO:43, an A instead of P at position 9 of SEQ ID NO:43, an A or G instead of P at position 10 of SEQ ID NO:43, an F instead of L at position 11 of SEQ ID NO:43, a Y instead of F at position 12 of SEQ ID NO:43, and/or an I instead of V at position 22 of SEQ ID NO:43.

2. The modified cell of claim 1, wherein the increased protein production is an increase of at least 1.1 fold as compared to the production of said protein by a parental cell that lacks the reduction in Ubc9 protein production and/or activity.

3. The modified cell of claim 1, wherein the genetic modification is a modification of an expression-regulating sequence or the coding sequence of the ubc9 gene.

4. The modified cell of claim 3, wherein the genetic modification reduces Ubc9 protein production.

5. The modified cell of claim 4, wherein the genetic modification disrupts the promoter sequence of the ubc9 gene.

6. The modified cell of claim 1, wherein the ubc9 gene has a wild type counterpart that encodes a Ubc9 protein comprising SEQ ID NO:2.

* * * * *

SEQUENCE LISTING

<160> NUMBER OF SEQ ID NOS: 54

<210> SEQ ID NO 1
<211> LENGTH: 2470
<212> TYPE: DNA
<213> ORGANISM: Myceliophthora thermophila

<400> SEQUENCE: 1

```
ggtaccagaa agcttgcgtt ggggtaggtt atgagcgcaa aggccggggc acgcgtgtac      60
cgaggttaga tgggggggga atccccacgt tgaggatgca agagcagggt cgcaacggat     120
tggtttatcg catcgagctc ttcccaaaag agctggtcgg gcggcgtggg gtgacgaaag     180
taatccgtaa ggtaatattg gactgtcaac tagaaacaca cgttggagaa aatgctaaga     240
gttgggtaaa tgggggcaag agatgatgca tgccgtgggg atgtgcatgt gcagcatgtg     300
ctcgacccgg gcgtccctta tgctccacca ccgaggcccc tttgggatcg tcccgctccc     360
ggattctagg aaccgagaag agggtctgga agaaccaccc tgtcccgcgt caaaggatcc     420
tggcctgctt gcctctttgt actccgtagc tatggcttca gcacaccggt ccccagatcc     480
cgacgctggt cgatccaatc atccaccttt tcgctctacg cagcactgat cctcaacgtt     540
ggttcttttt cgtatgacca gatgtagatg gtggggtgtg ccaccagccc ggactactat     600
gtaaggtacc gagtagtacc tcttctcgtc acattctggg gcgcgcttgtt taaatgattc     660 tacagactcc ttatccgggc gtggcattca ttcaggagag ggtgagctcc taaagcaaac     720
cgaagagagt acctaactcc ctacctcacc tattgattac acgacctcaa gcaagtacct     780
aaggtaaggc atttacctcc tttagataac cggcaccccg cgaaagagac cccggagagt     840
tgccccgcag tgaaaaggct cggaggaagg tagcgtacgg ggtaaagaac ttctagtgaa     900
ttgcagtgca tgcatgcatt gcatgcatgg agaaccagct gttctccgcc ttccatttcg     960
gggctgtgac agaacaaaca aattggtccg tgcgggcgcc cgaatttctg ccttccaagg    1020
gcgttcccgt cacgccgtct cgcagctccc ctcactgcgt tccagaattc cgggcgatat    1080
atcccgtgct tcccatccaa aggctcgact tgcgtggcgc tcattgcatc gcaccctggc    1140
```

-continued

```
tcaggagtgc aaccgaaccg ttgccagctg gcaccatttt cctttgtctc gttatctagt    1200
ctgcccacgg cttctggcgg cagccgacga cctggcccct ctgacatccg aaccattgga    1260
gaaaacccca tattgatcga agttccataa caactgccaa catgtcgcta tgccaaaatc    1320
gtctgcagga ggagcggtac gtcaaccgtc gctgtgcttc cggtaccccc gcgcgcgaca    1380
gcctcactaa cttggcgtcc acggtttagc aagcagtggc gcaaggacca tccgtttggc    1440
ttctatgcgc gaccgcagaa gaatgccagg gcgtgcttg acctcaaggt ctggagtgt    1500 ggtatcccgg gcaaagagaa gaccatgtgg gaaggcggcc tgttcaagct ggtggtgaca    1560
tttcccgacg gtacgcggca tccttcctg cggttctttt acggaaacgt tttacactaa    1620
ctaatcactc gtctcataca gagtatccca cgaaaccccc caagtgtaag tagcccggct    1680
gttgtgcgcc gatgttgaag cgcgggagaa ccacacgact aacattcgcc ctttctgtag    1740
gcaagtttac gccgcctctc ttccacccca acgtctaccc atccggcacc gtctgtttgt    1800
cgattctgaa cgaagaagag gcgtggaagc ccgcgattac catcaagcag atcctgcttg    1860
gcgtccagga cctcctcaac gaccccaacc cagaatctcc cgctcaggcc gaggcataca    1920
acatgtacaa gaaagacaga gtgcagtacg agaggcgcat caggcagatt gtgcgggaga    1980
atgccgcgcc atgaaagggt cttgcaggac tacgtcttgc gcacggccga agggatagaa    2040
ccgggtatgg aattctgatt acggagttat gggataccaa tggcggtggg cgattacagc    2100
atttggagtt cagacggcac gacatcatcg ggatcttctt ctactgcggg ttacgaaacg    2160
cttgatcttg gatccggggg aggctgaggg gtgggatgag atacgccgta ggcagaatta    2220
tgctgcgcga caacagatca ggtgtatgcg atgatttctc ccatcgtggc gtatgcacag    2280
agacaactct tccgcaggga caagaggat cgagactatc accccgtga tatgtcgccc    2340 caaacattga agtggtgttg ccgaagtgtc acatcccttc ccgcggggtc ttggcaatgc    2400
gctcaagcag ccattggctc gccccccacc atggacttgg gggcagctta ctgcagtaag    2460
cctcttgaga                                                          2470
```

<210> SEQ ID NO 2
<211> LENGTH: 157
<212> TYPE: PRT
<213> ORGANISM: Myceliophthora thermophila

<400> SEQUENCE: 2

Met Ser Leu Cys Gln Asn Arg Leu Gln Glu Glu Arg Lys Gln Trp Arg
1               5                   10                  15

Lys Asp His Pro Phe Gly Phe Tyr Ala Arg Pro Gln Lys Asn Ala Gln
                20                  25                  30

Gly Val Leu Asp Leu Lys Val Trp Glu Cys Gly Ile Pro Gly Lys Glu
            35                  40                  45

Lys Thr Met Trp Glu Gly Gly Leu Phe Lys Leu Val Val Thr Phe Pro
        50                  55                  60

Asp Glu Tyr Pro Thr Lys Pro Pro Lys Cys Lys Phe Thr Pro Pro Leu
65                  70                  75                  80

Phe His Pro Asn Val Tyr Pro Ser Gly Thr Val Cys Leu Ser Ile Leu
                85                  90                  95

Asn Glu Glu Glu Ala Trp Lys Pro Ala Ile Thr Ile Lys Gln Ile Leu
                100                 105                 110

Leu Gly Val Gln Asp Leu Leu Asn Asp Pro Asn Pro Glu Ser Pro Ala
            115                 120                 125

Gln Ala Glu Ala Tyr Asn Met Tyr Lys Lys Asp Arg Val Gln Tyr Glu

Arg Arg Ile Arg Gln Ile Val Arg Glu Asn Ala Ala Pro
145             150             155

<210> SEQ ID NO 3
<211> LENGTH: 6574
<212> TYPE: DNA
<213> ORGANISM: Artificial sequence
<220> FEATURE:
<223> OTHER INFORMATION: ubc9-amdS insertion cassette

<400> SEQUENCE: 3

| | | | | | |
|---|---|---|---|---|---|
| ggccgcggta | ccagaaagct | tgcgttgggg | taggttatga | gcgcaaaggc | cggggcacgc | 60 |
| gtgtaccgag | gttagatggg | gggggaatcc | ccacgttgag | gatgcaagag | cagggtcgca | 120 |
| acggattggt | ttatcgcatc | gagctcttcc | caaaagagct | ggtcgggcgg | cgtgggggtga | 180 |
| cgaaagtaat | ccgtaaggta | atattggact | gtcaactaga | aacacacgtt | ggagaaaatg | 240 |
| ctaagagttg | ggtaaatggg | ggcaagagat | gatgcatgcc | gtggggatgt | gcatgtgcag | 300 |
| catgtgctcg | acccgggcgt | cccttatgct | ccaccaccga | ggcccctttg | ggatcgtccc | 360 |
| gctcccggat | tctaggaacc | gagaagaggg | tctggaagaa | ccaccctgtc | ccgcgtcaaa | 420 |
| ggatcctggc | ctgcttgcct | cttttgtactc | cgtagctatg | gcttcagcac | accggtcccc | 480 |
| agatcccgac | gctggtcgat | ccaatcatcc | accttttcgc | tctacgcagc | actgatcctc | 540 |
| aacgttggtt | cttttttcgta | tgaccagatg | tagatggtgg | ggtgtgccac | cagcccggac | 600 |
| tactatgtaa | ggtaccgagt | agtacctctt | ctcgtcacat | tctgggcgcg | cttgtttaaa | 660 |
| tgattctaca | gactccttat | ccgggcgtgg | cattcattca | ggagagggtg | agctcctaaa | 720 |
| gcaaaccgaa | gagagtacct | aactcccctac | ctcacctatt | gattacacga | cctcaagcaa | 780 |
| gtacctaagg | taaggcattt | acctcccttta | gataaccggc | accccgcgaa | agagacccccg | 840 |
| gagagttgcc | ccgcagtgaa | aaggctcgga | ggaaggtagc | gtacgggggta | aagaacttct | 900 |
| agtgaattgc | agtgcatgca | tgcattgcat | gcatggagaa | ccagctgttc | tccgccttcc | 960 |
| atttcgggggc | tgtgacagaa | caaacaaatt | ggtccgtgcg | ggcgcccgaa | tttctgcctt | 1020 |
| ccaagggcgt | tcccgtcacg | ccgtctcgca | gctccccctca | ctgcgttcca | gaattccggg | 1080 |
| cgatatatcc | cgtgcttccc | atccaaaggc | tcgacttgcg | tggcgctcat | tgcatcgcac | 1140 |
| cctggctcag | gagtgcaacc | gaaccgttgc | cagctggcac | cattttcctt | tgtctcgtta | 1200 |
| tctagtctgc | ccacggcttc | tggcggcagc | cgacgacctg | gcccttctga | catccgaacc | 1260 |
| attttcgaag | gtaccacgac | caagaagatc | acggtcgtca | cccagttcct | caagaactcg | 1320 |
| gccggcgagc | tctccgagat | caagcggttc | tacgtccaga | acggcaaggt | catccccaac | 1380 |
| tccgagtcca | ccatcccggg | cgtcgaggggc | aactccatca | cccaggactg | gtgcgaccgc | 1440 |
| cagaaggccg | ccttcggcga | cgtgaccgac | ttccaggaca | agggcggcat | ggtccagatg | 1500 |
| ggcaaggccc | tcgcggggcc | catggtcctc | gtcatgtcca | tctgggacga | ccacgccgtc | 1560 |
| aacatgctct | ggctcgactc | cacctggccc | atcgacggcg | ccggcaagcc | gggcgccgag | 1620 |
| cgcggtgcct | gccccaccac | ctcgggcgtc | ccgctgagg | tcgaggccga | ggccccccaac | 1680 |
| tccaacgtca | tcttctccaa | catccgcttc | ggccccatcg | gctccaccgt | ctccggcctg | 1740 |
| cccgacggcg | gcagcggcaa | ccccaacccg | cccgtcagct | cgtccacccc | ggtcccctcc | 1800 |
| tcgtccacca | catcctccgg | ttcctccggc | ccgactggcg | gcacgggtgt | cgctaagcac | 1860 |
| tatctagact | ggaaacgcaa | ccctgaaggg | attcttcctt | tgagagatgg | aagcgtgtca | 1920 |

```
tatctcttcg gttctacggc aggtttttt  ctgctctttc gtagcatggc atggtcactt    1980
cagcgcttat ttacagttgc tggtattgat ttcttgtgca aattgctatc tgacacttat    2040
tagctatgga gtcaccacat ttcccagcaa cttccccact tcctctgcaa tcgccaacgt    2100
cctctcttca ctgagtctcc gtccgataac ctgcactgca accggtgccc catggtacgc    2160
ctccggatca tactcttcct gcacgagggc atcaagctca ctaaccgcct tgaaactctc    2220
attcttctta tcgatgttct tatccgcaaa ggtaaccgga acaaccacgc tcgtgaaatc    2280
cagcaggttg atcacagagg catacccata gtaccggaac tggtcatgcc gtaccgcagc    2340
ggtaggcgta atcggcgcga tgatggcgtc cagttccttc ccggcctttt cttcagcctc    2400
ccgccatttc tcaaggtact ccatctggta attccacttc tggagatgcg tgtcccagag    2460
ctcgttcatg ttaacagctt tgatgttcgg gttcagtagg tctttgatat ttggaatcgc    2520
cggctcgccg gatgcactga tatcgcgcat tacgtcggcg ctgccgtcag ccgcgtagat    2580
atgggagatg agatcgtggc cgaaatcgtg cttgtatggc gtccacgggg tcacggtgtg    2640
accggctttg gcgagtgcgg cgacggtggt ttccacgccg cgcaggatag gagggtgtgg    2700
aaggacattg ccgtcgaagt tgtagtagcc gatattgagc ccgccgttct tgatcttgga    2760
ggcaataatg tccgactcgg actggcgcca gggcatgggg atgaccttgg agtcgtattt    2820
ccatggctcc tgaccgagga cggatttggt gaagaggcgg aggtctaaca tacttcatca    2880
gtgactgccg gtctcgtata tagtataaaa agcaagaaag gaggacagtg gaggcctggt    2940
atagagcagg aaaagaagga agaggcgaag gactcaccct caacagagtg cgtaatcggc    3000
ccgacaacgc tgtgcaccgt ctcctgaccc tccatgctgt tcgccatctt tgcatacggc    3060
agccgcccat gactcggcct tagaccgtac aggaagttga acgcggccgg cactcgaatc    3120
gagccaccga tatccgttcc tacaccgatg acgccaccac gaatcccaac gatcgcaccc    3180
tcaccaccag aactgccgcc gcacgaccag ttcttgttgc gtgggttgac ggtgcgcccg    3240
atgatgttgt tgactgtctc gcagaccatc agggtctgcg ggacagaggt cttgacgtag    3300
aagacggcac cggctttgcg gagcatggtt gtcagaaccg agtccccttc gtcgtacttg    3360
tttagccatg agatgtagcc cattgatgtt tcgtagccct ggtggcatat gttagctgac    3420
aaaaagggac atctaacgac ttaggggcaa cggtgtacct tgactcgaag ctggtctttg    3480
agagagatgg ggaggccatg gagtggacca acgggtctct tgtgctttgc gtagtattca    3540
tcgagttccc ttgcctgcgc gagagcggcg tcagggaaga actcgtgggc gcagtttgtc    3600
tgcacagaag ccagcgtcag cttgatagtc ccataaggtg gcgttgttac atctccctga    3660
gaggtagagg ggaccctact aactgctggg cgattgctgc ccgtttacag aatgctagcg    3720
taacttccac cgaggtcaac tctccggccg ccagcttgga cacaagatct gcagcggagg    3780
cctctgtgat cttcagttcg gcctctgaaa ggatccccga tttctttggg aaatcaataa    3840
cgctgtcttc cgcaggcagc gtctggactt tccattcatc agggatggtt tttgcgaggc    3900
gggcgcgctt atcagcggcc agttcttccc aggattgagg cattctgtgt tagcttatag    3960
tcaggatgtt ggctcgacga gtgtaaactg ggagttggca tgagggttat gtaggcttct    4020
ttagccccgc atcccctca  ttctcctcat tgatcccggg ggagcggatg tgttgataa    4080
gagactaatt atagggttta gctggtgcct agctggtgat tggctggctt cgccgaattt    4140
tacgggccaa ggaaagctgc agaaccgcgg cactggtaaa cggtaattaa gctatcagcc    4200
ccatgctaac gagtttaaat tacgtgtatt gctgataaac accaacagag ctttactgaa    4260
agatgggagt cacggtgtgg cttccccact gcgattattg cacaagcagc gagggcgaac    4320
```

```
ttgactgtcg tcgctgagca gcctgcagtc aaacatacat atatatcaac cgcgaagacg   4380
tctggccttg tagaacacga cgctccctag caacacctgc cgtgtcagcc tctacggttg   4440
ttacttgcat tcaggatgct ctccagcggg cgagctattc aaaatattca aagcaggtat   4500
ctcgtattgc caggattcag ctgaagcaac aggtgccaag gaaatctgcg tcggttctca   4560
tctgggcttg ctcggtcctg gcgtagatct agaggtacca cgaccaagaa gatcacggtc   4620
gtcacccagt tcctcaagaa ctcggccggc gagctctccg agatcaagcg gttctacgtc   4680
cagaacggca aggtcatccc caactccgag tccaccatcc cgggcgtcga gggcaactcc   4740
atcacccagg actggtgcga ccgccagaag gccgccttcg gcgacgtgac cgacttccag   4800
gacaagggcg gcatggtcca gatgggcaag gccctcgcgg ggcccatggt cctcgtcatg   4860
tccatctggg acgaccacgc cgtcaacatg ctctggctcg actccacctg gcccatcgac   4920
ggcgccggca agccgggcgc cgagcgcggt gcctgcccca ccacctcggg cgtccccgct   4980
gaggtcgagg ccgaggcccc caactccaac gtcatcttct ccaacatccg cttcggcccc   5040
atcggctcca ccgtctccgg cctgcccgac ggcggcagcg gcaaccccaa cccgcccgtc   5100
agctcgtcca ccccggtccc ctcctcgtcc accacatcct ccggttcctc cggcccgact   5160
ggcggcacgg gtgtcgctaa gcactattcg aaggagaaaa ccccatattg atcgaagttc   5220
cataacaact gccaacatgt cgctatgcca aaatcgtctg caggaggagc ggtacgtcaa   5280
ccgtcgctgt gcttccggta cccccgcgcg cgacagcctc actaacttgg cgtccacggt   5340
ttagcaagca gtggcgcaag gaccatccgt ttggcttcta tgcgcgaccg cagaagaatg   5400
cccagggcgt gcttgacctc aaggtctggg agtgtggtat cccgggcaaa gagaagacca   5460
tgtgggaagg cggcctgttc aagctggtgg tgacatttcc cgacggtacg cggcatcctt   5520
tcctgcggtt cttttacgga aacgttttac actaactaat cactcgtctc atacagagta   5580
tcccacgaaa ccccccaagt gtaagtagcc cggctgttgt gcgccgatgt tgaagcgcgg   5640
gagaaccaca cgactaacat tcgcccttc tgtaggcaag tttacgccgc ctctcttcca   5700
ccccaacgtc tacccatccg gcaccgtctg tttgtcgatt ctgaacgaag aagaggcgtg   5760
gaagcccgcg attaccatca agcagatcct gcttggcgtc caggacctcc tcaacgaccc   5820
caacccagaa tctcccgctc aggccgaggc atacaacatg tacaagaaag acagagtgca   5880
gtacgagagg cgcatcaggc agattgtgcg ggagaatgcc gcgccatgaa agggtcttgc   5940
aggactacgt cttgcgcacg gccgaaggga tagaaccggg tatggaattc tgattacgga   6000
gttatgggat accaatggcg gtgggcgatt acagcatttg gagttcagac ggcacgacat   6060
catcgggatc ttcttctact gcgggttacg aaacgcttga tcttggatcc ggggaggct   6120 gaggggtggg atgagatacg ccgtaggcag aattatgctg cgcgacaaca gatcaggtgt   6180
atgcgatgat ttctcccatc gtggcgtatg cacagagaca actcttccgc agggaacaag   6240
aggatcgaga ctatcacccc cgtgatatgt cgccccaaac attgaagtgg tgttgccgaa   6300
gtgtcacatc ccttcccgcg gggtcttggc aatgcgctca agcagccatt ggctcgcccc   6360
ccaccatgga cttgggggca gcttactgca gtaagcctct tgagagacaa atcgagactc   6420
gcaacctcag cttctcagag atgcattgcg ttcctcacct ccagagggcc agctcctcac   6480
gtggtcgctt gtggtccctg cagaccccga acgctgtcaa agccttcgtt cttatcagtc   6540
atgttaaggt aatgacccat gtggaactgt tggc                              6574
```

<210> SEQ ID NO 4

```
<211> LENGTH: 4483
<212> TYPE: DNA
<213> ORGANISM: Artificial sequence
<220> FEATURE:
<223> OTHER INFORMATION: Expression cassette eg2
<220> FEATURE:
<221> NAME/KEY: misc_feature
<222> LOCATION: (1749)..(1749)
<223> OTHER INFORMATION: n is a, c, g, or t
<220> FEATURE:
<221> NAME/KEY: misc_feature
<222> LOCATION: (3668)..(3668)
<223> OTHER INFORMATION: n is a, c, g, or t

<400> SEQUENCE: 4
```

| | | | | | |
|---|---|---|---|---|---|
| ggccgctcta | gaactagtgg | atcccccggg | ctgcagtccc | ttacctatgg | gctcctagtc | 60 |
| tcgttcctct | ttttgataga | tttgtatttt | gcaacgttgc | aaaatgagac | atttcaatca | 120 |
| tatgtagccg | ccagctactg | ttagcgtact | cagcgttgcc | caaacggcgg | tttttctggg | 180 |
| tagcactgtg | ccgcgtgccc | ctgagccgtg | cgtcgcggaa | accccttaa | gtagcaagta | 240 |
| tgttaccgcc | gagaccgaca | atgctgttgg | ttacctcgct | ggtccatgat | tgcaatctag | 300 |
| atatcgtgcg | gggcttttgc | aatcggtttt | ccctacccac | tttcttcttt | tggacacttt | 360 |
| ctcttttgga | aaatgccgaa | atgatgcggc | tcgctcacgc | cccgaagtcc | cgagctgggg | 420 |
| ctagatccgt | gattgcaacg | cggtgcgaac | gcgactgggg | cagacctcgc | tcagccttgg | 480 |
| tcgtgccgga | atggcgggta | cctttaccag | gtcgggatca | attacatagg | atgccatgtg | 540 |
| cgtggatttg | attgcatcgc | tgtccctttt | gtatgtgtcc | gagagcgaga | catcaacgcg | 600 |
| aaaaccggaa | tgctcccaac | gtcgctctct | gttcataggg | tcttttttt | tcttctgctc | 660 |
| catatcatct | gtcttgaact | aagtgatcat | ctgctgtcac | gtcccgccca | atgattgtaa | 720 |
| agaatgataa | gtgatgctcg | ccggggccag | gctctgtgaa | agttccctct | ttggttgacg | 780 |
| atcaggtagc | gccaacgttg | attgggccgc | ccgtaaaatc | cgaccctgtc | tcctttcgtt | 840 |
| gcaagtctcc | gcgagaccgt | gccaagcatg | ttctccggat | ccctcaatta | cataaggttt | 900 |
| ggctccaggg | taggtctgga | agctacccac | ctcggccaag | caaccaatca | caaccagacc | 960 |
| tcgcggcgtt | tcgaccttcc | tggtttgtct | cagggctggc | caacgtcctc | ccgtggcggg | 1020 |
| tgcctggtga | tcgcaggtcg | caggcgagtg | ccgggcacgc | ggagccccg | tcaaagcttg | 1080 |
| acccttttcag | agctaggttt | cattaggcct | tcgaaaacaa | cccaaggccc | cgtcgcaacc | 1140 |
| atcacaaccg | gccgataacc | agatctcggt | aggtccgata | aggatccaaa | atggtgtcgg | 1200 |
| ctgacgttgc | atgtgcccag | gcaggaggat | gatccccagg | gttgttgccg | gcagctcccg | 1260 |
| cacgtcgggg | aggggaggg | ggaggggaaa | gccctaacta | acgttcgttc | tatcacgggc | 1320 |
| cgaccgggcc | atgctttcgg | cttgtgagcg | gtggggtcaa | gggcaacaag | aaatgctaag | 1380 |
| tgcgggacga | agacacgcgg | gcatgaggtc | tcagggtgac | ctgcgcaaaa | ccaagtccca | 1440 |
| ctcgccatgc | ctccagcagc | aacgttgccg | tagaagggtc | aggggggtttg | ttgtagaccc | 1500 |
| acgaccatgc | tgccggcgag | cggagggttg | gcttgctaca | ggcgctgaag | ggtcaactcg | 1560 |
| gtgcccaaag | tggctaccaa | gcgtgccatc | aagggaaatg | agatgatggt | ggctcgtggg | 1620 |
| caaagaaaag | acaagggagg | tgactctaga | gagatgctct | cgagttcacg | ggtataagag | 1680 |
| cactgtgatc | gttcacaaag | ccggcgtact | cctctagagc | atctatcatc | aacatcacca | 1740 |
| gaaaggtcnt | agaccaggtg | gttgccatat | ccagtcgcaa | aagagccaaa | gagcgaagga | 1800 |
| gcacgaaagc | acagcccaat | cattccctgc | tttgctactt | cttctccacc | atgaagtcct | 1860 |
| ccatcctcgc | cagcgtcttc | gccacgggcg | ccgtggctca | aagtggtccg | tggcagcaat | 1920 |

```
gtggtggcat cggatggcaa ggatcgaccg actgtgtgtc gggttaccac tgcgtctacc   1980
agaatgattg gtacagccag tgcgtgcctg gcgcggcgtc gacaacgctc cagacatcta   2040
ccacgtccag gcccaccgcc accagcaccg cccctccgtc gtccaccacc tcgcctagca   2100
agggcaagct caagtggctc ggcagcaacg agtcgggcgc cgagttcggg gagggcaact   2160
accccggcct ctggggaaag cacttcatct tcccgtcgac ttcggcgatt caggtacggg   2220
ccaataataa tatattatta tagcaggcag gagggagcag gagaagaagg gaggggcagg   2280
tggccaacaa tcggaagaag accgggaggc actgaccgtt gattcctttg tgtaatagac   2340
gctcatcaat gatggataca acatcttccg gatcgacttc tcgatggagc gtctggtgcc   2400
caaccagttg acgtcgtcct tcgacgaggg ctacctccgc aacctgaccg aggtggtcaa   2460
cttcgtgacg aacgcgggca agtacgccgt cctggacccg cacaactacg gccggtacta   2520
cggcaacgtc atcacggaca cgaacgcgtt ccggaccttc tggaccaacc tggccaagca   2580
gttcgcctcc aactcgctcg tcatcttcga caccaacaac gagtacaaca cgatggacca   2640
gaccctggtg ctcaacctca accaggccgc catcgacggc atccgggccg ccggcgcgac   2700
ctcgcagtac atcttcgtcg agggcaacgc gtggagcggg gcctggagct ggaacacgac   2760
caacaccaac atggccgcct gacggacccg cagaacaaga tcgtgtacga gatgcaccag   2820
tacctcgact cggacagctc gggcaccac gccgagtgcg tcagcagcaa catcggcgcc   2880
cagcgcgtcg tcggagccac ccagtggctc cgcgccaacg gcaagctcgg cgtcctcggc   2940
gagttcgccg gcgcgccaa cgccgtctgc cagcaggccg tcaccggcct cctcgaccac   3000
ctccaggaca acagcgacgt ctggctgggt gccctctggt gggccgccgg tccctggtgg   3060
ggcgactaca tgtactcgtt cggtaagttt ctcccttgtt cttggctttc ccccagtaa   3120 gggagtcagg caacatgccc aagaccggct cggcttcgct tcaaggcgtt cgttgtacac   3180
actgaagagt tccaacttcc aaccctgttc gtgtcctccg atcagcttcg acggggtgaa   3240
gggggaaggg atttgggagt gaggtggagg tcaaaaggag ggatatcccc agatctccac   3300
aaacggccct gagccaacaa cagcctctgg ggtcaaaatg ggcgccaacc atacggtcat   3360
tcactcagga cacctgctaa cgcgtctctt tttttgttt ccagagcctc cttcgggcac   3420
cggctatgtc aactacaact cgatcctaaa gaagtacttg ccgtaaggat cctaagtaag   3480
taaacgaacc tctctgaagg aggttctgag acacgcgcga ttcttctgta tatagttta   3540 tttttcactc tggagtgctt cgctccacca gtacataaac ctttttttc acgtaacaaa   3600 atggcttctt ttcagaccat gtgaaccatc ttgatgcctt gacctcttca gttctcactt   3660
taacgtantt cgcgttagtc tgtatgtccc agttgcatgt agttgagata aatacccctg   3720
gaagtgggtc tgggcctttg tgggacgag ccctctttct gtggtctgga gagcccgctc   3780
tctaccgcct accttcttac cacagtacac tactcacaca ttgctgaact gacccatcat   3840
accgtacttt atcctgttaa ttcgtggtgc tgtcgactat tctattgct caaatgagaa   3900 gcacattcat cggcgcaggg atacacggtt tatggacccc aagagtgtaa ggactattat   3960
tagtaatatt atatgcctct aggcgcctta acttcaacag gcgagcacta ctaatcaact   4020
tttggtagac ccaattacaa acgaccatac gtgccggaaa ttttgggatt ccgtccgctc   4080
tccccaacca agctagaaga ggcaacgaac agccaatccc ggtgctaatt aaattatatg   4140 gttcatttt tttaaaaaaa tttttcttc ccatttcct ctcgcttttc ttttcgcat   4200 cgtagttgat caaagtccaa gtcaagcgag ctatttgtgc tatagctcgg tggctataat   4260
```

```
cagtacagct tagagaggct gtaaaggtat gataccacag cagtattcgc gctataagcg    4320
gcactcctag actaattgtt acggtctaca gaagtaggta ataaaagcgt taattgttct    4380
aaatactaga ggcacttaga gaagctatct aaatatatat tgaccctagc ttattatccc    4440
tattagtaag ttagttagct ctaacctata gatagccaaa tgc                      4483
```

<210> SEQ ID NO 5
<211> LENGTH: 3935
<212> TYPE: DNA
<213> ORGANISM: Artificial sequence
<220> FEATURE:
<223> OTHER INFORMATION: Expression cassette AnPGII
<220> FEATURE:
<221> NAME/KEY: misc_feature
<222> LOCATION: (1722)..(1722)
<223> OTHER INFORMATION: n is a, c, g, or t
<220> FEATURE:
<221> NAME/KEY: misc_feature
<222> LOCATION: (3120)..(3120)
<223> OTHER INFORMATION: n is a, c, g, or t

<400> SEQUENCE: 5

```
gggctgcagt cccttaccta tgggctccta gtctcgttcc tctttttgat agatttgtat      60
tttgcaacgt tgcaaaatga gacatttcaa tcatatgtag ccgccagcta ctgttagcgt     120
actcagcgtt gcccaaacgg cggttttcct gggtagcact gtgccgcgtg cccctgagcc     180
gtgcgtcgcg gaaaccccct taagtagcaa gtatgttacc gccgagaccg acaatgctgt     240
tggttacctc gctggtccat gattgcaatc tagatatcgt gcggggcttt tgcaatcggt     300
tttccctacc cactttcttc ttttggacac tttctctttt ggaaaatgcc gaaatgatgc     360
ggctcgctca cgccccgaag tcccgagctg gggctagatc cgtgattgca acgcggtgcg     420
aacgcgactg gggcagacct cgctcagcct tggtcgtgcc ggaatggcgg gtacctttac     480
caggtcggga tcaattacat aggatgccat gtgcgtggat ttgattgcat cgctgtccct     540
tttgtatgtg tccgagagcg agacatcaac gcgaaaaccg gaatgctccc aacgtcgctc     600
tctgttcata gggtcttttt ttttcttctg ctccatatca tctgtcttga actaagtgat     660
catctgctgt cacgtcccgc ccaatgattg taaagaatga taagtgatgc tcgccggggc     720
caggctctgt gaaagttccc tctttggttg acgatcaggt agcgccaacg ttgattgggc     780
cgcccgtaaa atccgaccct gtctcctttc gttgcaagtc tccgcgagac cgtgccaagc     840
atgttctccg gatccctcaa ttacataagg tttggctcca gggtaggtct ggaagctacc     900
cacctcggcc aagcaaccaa tcacaaccag acctcgcggc gtttcgacct tcctggtttg     960
tctcagggct ggccaacgtc ctcccgtggc gggtgcctgg tgatcgcagg tcgcaggcga    1020
gtgccgggca cgcggagccc ccgtcaaagc ttgacccttt cagagctagg tttcattagg    1080
ccttcgaaaa caacccaagg ccccgtcgca accatcacaa ccggccgata accagatctc    1140
ggtaggtccg ataaggatcc aaaatggtgt cggctgacgt tgcatgtgcc caggcaggag    1200
gatgatcccc agggttgttg ccggcagctc ccgcacgtcg gggagggga ggggagggg      1260 aaagccctaa ctaacgttcg ttctatcacg ggccgaccgg gccatgcttt cggcttgtga    1320
gcggtggggt caagggcaac aagaaatgct aagtgcggga cgaagacacg cgggcatgag    1380
gtctcagggt gacctgcgca aaaccaagtc ccactcgcca tgcctccagc agcaacgttg    1440
ccgtagaagg gtcaggggt ttgttgtaga cccacgacca tgctgccggc gagcggaggg     1500
ttggcttgct acaggcgctg aagggtcaac tcggtgccca agtggctac caagcgtgcc     1560 atcaagggaa atgagatgat ggtggctcgt gggcaaagaa aagacaaggg aggtgactct    1620
```

```
agagagatgc tctcgagttc acgggtataa gagcactgtg atcgttcaca aagccggcgt    1680
actcctctag agcatctatc atcaacatca ccagaaaggt cntagaccag gtggttgcca    1740
tatccagtcg caaaagagcc aaagagcgaa ggagcacgaa agcacagccc aatcattccc    1800
tgctttgcta cttcttctcc accatgcatt cctttgcttc cctcctcgct tacggcctcg    1860
tggctggtgc tacgttcgct tcggcctccc ccatcgaggc ccgcgacagc tgcaccttca    1920
ctactgccgc tgccgccaag gccggtaagg ctaagtgctc caccatcacc ctcaacaaca    1980
tcgaggtgcc cgctggcacg accctggacc tcaccggtct gacttcgggc accaaggtca    2040
tcttcgaggg cacgaccact tttcagtacg aggagtgggc tggcccccctc atctcgatgt    2100
cgggcgagca tatcaccgtc actggtgcct cgggccacct catcaactgc gacggcgctc    2160
gctggtggga tggtaagggc acctccggta agaagaagcc gaagttcttc tacgcccacg    2220
gcctggactc cagctcgatc accggcctca acatcaagaa cacgcccctc atggccttct    2280
ccgtgcaggc caacgacatc accttcaccg acgtcactat caacaacgcc gacggcgaca    2340
cccagggcgg tcacaacact gacgccttcg acgtgggtaa ctcggtcggc gtcaacatca    2400
tcaagccgtg ggtccacaac caggacgatt gcctcgcggt caacagcggc gagaacatct    2460
ggttcactgg cggcacgtgc atcggcggtc acggcctgag catcggctcc gtcggtgacc    2520
gcagcaacaa cgtcgtcaag aacgtcacga tcgagcactc caccgtgtcc aacagcgaga    2580
acgccgtccg gatcaagacc atctccggcg ccacgggcag cgtcagcgag atcacctaca    2640
gcaacatcgt catgagcggc atctccgact acggcgtcgt catccagcag gactacgagg    2700
acggcaagcc caccggtaag cccactaacg gtgtgactat ccaggacgtc aagctggaga    2760
gcgtgacggg tagcgtcgac agcggcgcca ccgagatcta cctcctgtgc ggttcgggca    2820
gctgctccga ctggacctgg gatgacgtca aggtgaccgg cggcaagaag agcactgcct    2880
gcaagaactt cccgtccgtc gctagctgct aagaattcgg atcctaagta agtaaacgaa    2940
cctctctgaa ggaggttctg agacacgcgc gattcttctg tatatagttt tatttttcac    3000
tctggagtgc ttcgctccac cagtacataa accttttttt tcacgtaaca aaatggcttc    3060
ttttcagacc atgtgaacca tcttgatgcc ttgacctctt cagttctcac tttaacgtan    3120
ttcgcgttag tctgtatgtc ccagttgcat gtagttgaga taaataccccc tggaagtggg    3180
tctgggcctt tgtgggacgg agccctcttt ctgtggtctg gagagcccgc tctctaccgc    3240
ctaccttctt accacagtac actactcaca cattgctgaa ctgacccatc ataccgtact    3300
ttatcctgtt aattcgtggt gctgtcgact attctatttg ctcaaatgga gagcacattc    3360
atcggcgcag ggatacacgg tttatggacc ccaagagtgt aaggactatt attagtaata    3420
ttatatgcct ctaggcgcct taacttcaac aggcgagcac tactaatcaa cttttggtag    3480
acccaattac aaacgaccat acgtgccgga aattttggga ttccgtccgc tctccccaac    3540
caagctagaa gaggcaacga acagccaatc ccggtgctaa ttaaattata tggttcatt    3600
ttttaaaaa aatttttttct tcccattttc ctctcgcttt tcttttttcgc atcgtagttg    3660
atcaaagtcc aagtcaagcg agctatttgt gctatagctc ggtggctata atcagtacag    3720
cttagagagg ctgtaaaggt atgataccac agcagtattc gcgctataag cggcactcct    3780
agactaattg ttacggtcta cagaagtagg taataaaagc gttaattgtt ctaaatacta    3840
gaggcactta gagaagctat ctaaatatat attgacccta gcttattatc cctattagta    3900
agttagttag ctctaaccta tagatagatg catgc                                3935
```

<210> SEQ ID NO 6
<211> LENGTH: 5267
<212> TYPE: DNA
<213> ORGANISM: Artificial sequence
<220> FEATURE:
<223> OTHER INFORMATION: Expression cassette TwBxl1
<220> FEATURE:
<221> NAME/KEY: misc_feature
<222> LOCATION: (4452)..(4452)
<223> OTHER INFORMATION: n is a, c, g, or t

<400> SEQUENCE: 6

```
ggccgctcta gaactagtgg atccccgggg ctgcagtccc ttacctatgg gctcctagtc      60
tcgttcctct ttttgataga tttgtatttt gcaacgttgc aaaatgagac atttcaatca     120
tatgtagccg ccagctactg ttagcgtact cagcgttgcc caaacggcgg ttttctgggg     180
tagcactgtg ccgcgtgccc ctgagccgtg cgtcgcggaa accccttaa gtagcaagta     240
tgttaccgcc gagaccgaca atgctgttgg ttacctcgct ggtccatgat tgcaatctag     300
atatcgtgcg gggcttttgc aatcggtttt ccctacccac tttcttcttt tggacacttt     360
ctcttttgga aaatgccgaa atgatgcggc tcgctcacgc cccgaagtcc cgagctgggg     420
ctagatccgt gattgcaacg cggtgcgaac gcgactgggg cagacctcgc tcagccttgg     480
tcgtgccgga atggcgggta cctttaccag gtcgggatca attacatagg atgccatgtg     540
cgtggatttg attgcatcgc tgtccctttt gtatgtgtcc gagagcgaga catcaacgcg     600
aaaaccggaa tgctcccaac gtcgctctct gttcataggg tcttttttt tcttctgctc     660
catatcatct gtcttgaact aagtgatcat ctgctgtcac gtcccgccca atgattgtaa     720
agaatgataa gtgatgctcg ccggggccag gctctgtgaa agttccctct ttggttgacg     780
atcaggtagc gccaacgttg attgggccgc ccgtaaaatc cgaccctgtc tcctttcgtt     840
gcaagtctcc gcgagaccgt gccaagcatg ttctccggat ccctcaatta cataaggttt     900
ggctccaggg taggtctgga agctacccac ctcggccaag caaccaatca caaccagacc     960
tcgcggcgtt tcgaccttcc tggtttgtct cagggctggc caacgtcctc ccgtggcggg    1020
tgcctggtga tcgcaggtcg caggcgagtg ccgggcacgc ggagccccg tcaaagcttg    1080
acccttttcag agctaggttt cattaggcct tcgaaaacaa cccaaggccc cgtcgcaacc    1140
atcacaaccg gccgataacc agatctcggt aggtccgata aggatccaaa atggtgtcgg    1200
ctgacgttgc atgtgcccag gcaggaggat gatccccagg gttgttgccg gcagctcccg    1260
cacgtcgggg aggggagggg ggagggggaaa gccctaacta acgttcgttc tatcacgggc    1320
cgaccgggcc atgctttcgg cttgtgagcg gtggggtcaa gggcaacaag aaatgctaag    1380
tgcgggacga agacacgcgg gcatgaggtc tcagggtgac ctgcgcaaaa ccaagtccca    1440
ctcgccatgc ctccagcagc aacgttgccg tagaagggtc aggggggttttg ttgtagaccc    1500
acgaccatgc tgccggcgag cggagggttg gcttgctaca ggcgctgaag ggtcaactcg    1560
gtgcccaaag tggctaccaa gcgtgccatc aagggaaatg agatgatggt ggctcgtggg    1620
caaagaaaag acaagggagg tgactctaga gagatgctct cgagttcacg ggtataagag    1680
cactgtgatc gttcacaaag ccggcgtact cctctagagc atctatcatc aacatcacca    1740
gaaaggtcaa gaccaggtgg ttgccatatc cagtcgcaaa agagccaaag agcgaaggag    1800
cacgaaagca cagcccaatc attccctgct ttgctacttc ttctccacca tgtacgccaa    1860
gttcgccacc ctcgccgccc tcgtcgccgg cgccgccgcc cagaacgccg cccagaacaa    1920
ccagacctac gccaactaca gcagccagag ccagcccgac ctctaccccc agaccctcgc    1980
```

```
ccacctcaac ttcagcttcc ccgactgcat caacggcccc ctcaaggaca acatcgtctg    2040
cgacaccagc gccaactacg tcgaccgcgc cgagggcctg atcgccctct tcaccctcga    2100
ggagctgatc aacaacaccc agaacaccgc ccccggcgtc cccgcctcg gcctcccgcc     2160 ctaccaggtc tggtcggagg ccctccacgg cctcgaccgc gccaacttcg ccacgagcgg    2220
cgacgagtgg acctgggcca ccagcttccc catgcccatc ctcagcatgg ccgccctcaa    2280
ccgcacccts atcaaccaga tcgccggcat catcggcacc caggcccgcg ccttcaacaa    2340
cgccggccgc tacggcctcg acgcctacgc ccccaacatc aacggctacc gcaaccccct    2400
ctggggccgc ggccaggaga ccccggcga ggacgccaac ttcctcagca gcagctacgc     2460
ctacgagtac atcaccggcc tccagggcgg cgtcgacccc gaccacctca aggtcgtcgc    2520
caccgccaag cacttcgccg gctacgacct cgagaactgg ggcggcaaca gccgcctcgg    2580
cttcgacgcc agcatcaccc agcaggacct cgccgagtac tacaccccc agttcctcgc     2640 cgccagccgc tacgccaagg cccgcagctt catgtgcagc tacaacagcg tcaacggcgt    2700
ccccagctgc agcagcagct tcctgctcca gaccctcctc cgcgacaact gggacttccc    2760
cgagtacggc tacgtcagca gcgactgcga cgccgtctac aacgtcttca cccccacgg    2820 ctacgccagc aaccagagcg ccgccgccgc cgacagcctc cgcgccggca ccgacatcga    2880
ctgcggccag acctacccct ggaacctcaa ccagagcttc atcgagggca gcgtcacccg    2940
cggcgagatc gagcgcagca tcgtccgcct ctacagcaac ctcgtcaagc tcggctactt    3000
cgacggcgac aagagcgagt accgccagct cggctggaac gacgtcgtca ccaccgacgc    3060
ctggaacatc agctacgagg ccgccgtcga gggcatcgtc ctgctcaaga acgacggcat    3120
cctcccgctc agcaagcacg tcaagtcgat cgccctcatc ggcccctggg ccaacgccac    3180
cgagcagctc cagggcaact actacggcac cgcccccta ctcatcaccc cgctccaggg    3240
cgccagcgac gccggctaca aggtcaacta cgccctcggc accaacatcc tcggcaacac    3300
caccgagggc ttcgccgacg ccctctcggc cgcccagaag tcggacgtca tcgtctacct    3360
cggcggcatc gacaacacca tcgaggccga gggcaccgac cgcatgaacg tcacctggcc    3420
cggcaaccag ctcgacctca tccagcagct cagccagacc ggcaagcccc tcgtcgtcct    3480
ccagatgggc ggcggccagg tcgacagcag cagcatcaag ccaacagca aggtcaacgc     3540 cctcgtctgg ggcggctacc ccggccgag cggcggcacc gccatcttcg acatcctcag    3600
cggcaagcgc gtccccgccg ccgcctcgt caccacccag taccccgccg agtacgccac    3660
ccagttcccg gccaccgaca tgaacctccg ccccgacggc gccagcaacc cgggccagac    3720
gtatatgtgg tacaccggca ccccgtcta cgacttcggc tacggcctct tctacaccac    3780
cttcaaggag accgcccaga agctgggcag cagctcgttc gacatcagcg agatcgtcgc    3840
cgccccccgc agccccagct acgagtacag cgagctggtc cccttcgtca acatcaccgc    3900
caccatcaag aacaccggca agaccgccag ccccctacacc gccatgctgt cgccaacac    3960 caccaacgcc ggccccgccc cgtacccaa caagtggctc gtcggctacg accgcctcgc    4020
cagcatcgag cccggcaaga gcgccgacct cgtcatcccc gtcccatcg gcgccatcgc    4080 ccgcgtcgac gagaacggca accgcatcgt ctacccgggc gactaccagc tcgccctcaa    4140
cgtcgagcgc tcggtcgtct gggacatcaa gctcaccggc gacgccgtca ccatcgagaa    4200
ctggcccctc gacgagcagg agatccagcc cgacagcaac taatgaattc ggatcctaag    4260
taagtaaacg aacctctctg aaggaggttc tgagacacgc gcgattcttc tgtatatagt    4320
```

-continued

```
tttattttc   actctggagt gcttcgctcc accagtacat aaacctttt  tttcacgtaa   4380
caaaatggct  tctttcaga  ccatgtgaac catcttgatg ccttgacctc ttcagttctc   4440
actttaacgt  anttcgcgtt agtctgtatg tcccagttgc atgtagttga gataaatacc   4500
cctggaagtg  ggtctgggcc tttgtgggac ggagccctct ttctgtggtc tggagagccc   4560
gctctctacc  gcctaccttc ttaccacagt acactactca cacattgctg aactgaccca   4620
tcataccgta  ctttatcctg ttaattcgtg gtgctgtcga ctattctatt tgctcaaatg   4680
gagagcacat  tcatcggcgc agggatacac ggtttatgga ccccaagagt gtaaggacta   4740
ttattagtaa  tattatatgc ctctaggcgc cttaacttca acaggcgagc actactaatc   4800
aactttggt   agacccaatt acaaacgacc atacgtgccg gaaattttgg gattccgtcc   4860
gctctcccca  accaagctag aagaggcaac gaacagccaa tcccggtgct aattaaatta   4920
tatggttcat  tttttttaaa aaatttttt  cttcccattt tcctctcgct tttcttttc   4980
gcatcgtagt  tgatcaaagt ccaagtcaag cgagctattt gtgctatagc tcggtggcta   5040
taatcagtac  agcttagaga ggctgtaaag gtatgatacc acagcagtat tcgcgctata   5100
agcggcactc  ctagactaat tgttacggtc tacagaagta ggtaataaaa gcgttaattg   5160
ttctaaatac  tagaggcact tagagaagct atctaaatat atattgaccc tagcttatta   5220
tccctattag  taagttagtt agctctaacc tatagataga tgcatgc                5267
```

<210> SEQ ID NO 7
<211> LENGTH: 7794
<212> TYPE: DNA
<213> ORGANISM: Artificial sequence
<220> FEATURE:
<223> OTHER INFORMATION: pyr5 selection marker
<400> SEQUENCE: 7

```
gatctggcca  agggccacct tgaagtggtc ggcatctgac agtaaccgtc agcatagccc     60
cattgccgca  tcatgtagcc tccaaatccg tttccttcag gcgtggaggg gcgtaccata    120
taggatgttc  atcaaatcgc ggtggaaggg gtgctgatcc gtcaacacgg ggaagctcga    180
gatgatggcg  ccaaatttct cgctgcatgt ctcctgtgta atctgagcca ccggggttag    240
tgccgagtcc  gaaatcgaat catcaccagc ttcgtcgcaa acggtgtggt ggaatctggg    300
gagatttgaa  tcgatgagcc gggatcaccg acttgacttt gcgggtgtaa aacgccctaa    360
ttctgctaac  tgttcattga gcgtcagaaa atgtctgcga cctcgagcag taattcggga    420
ggcacatact  cttgaatccg ggacggactg taatggtgtt ctaggtcagc cagcatccca    480
ccactccgtc  aaaacatcca acatactctg agtcggcagt cgcctctgtg tccgcctgcg    540
gaacgtcagc  ctttctcgtc ttgcaacctt ataacctag  ccttcaaact tacgaaagga    600
tgatgtcgat  aaactcctgt gccctgtacg aaaatgatca gcttagttca ggaaaggaac    660
agcatatata  cgaattgaac ccttacgtag gcacaggcgc gatatccttc caggccatgg    720
caggcaacgc  gcagggtgct gtccgaattt ggcgatgggg gtgttttggga gttgtcagat    780
agggagcacc  tggcggggcg gtgtcgattt gccgtcccca agtcgcccga ataattttt    840
tgcggagagc  acaaaatgat aagataaggc aggcggtgtg cgttatcaaa atatcccaag    900
cccagctcga  gaagcattgc aagtgggta  cgacgtacgg agtactgtgt aactccgtag    960
acatacaaaa  aagtttaacg acccttgggc ccaccatga  atccaacccc accaagaaat   1020
tcgcgatgga  ggggctctct tcagctctgc gataggggga cgtttgacaa aactccctca   1080
tttctttttt  tcgaatcttc accaggagtt ccctccggta acaaataaac ttccagccca   1140
```

```
agaacccgta agacacgtac gaaccgacag acatggcccc actcgcttct tacaaagccg    1200
acttcctccg ggcggccatc gccggcaaca tcctcaagtt tggcagcttc gagctcaagt    1260
cgaagcgcat ctcgccctac ttcttcaacg cgggagactt ctaccgggcc gatctgctcg    1320
aggcgctcgc gacggcgtac gcgcacgcca tcatcgaggc gcaccggagc ggcgcgatcc    1380
agttcgacat cgtcttcggc ccggcctaca aggggatccc gttggcgacg gcggccacca    1440
ttcggctggg ccagctggat ccggccacgt acggccatac cacgtgctac tcgttcgacc    1500
gcaaggaggc aaaggaccac ggtgagggcg gcaacattgt gggggcgccg ctcaagggca    1560
agagggtgct tatcgtggat gatgtgatca cggctggcac ggcgaagcgt gaggcgatcg    1620
ccaagattga aaggagggc ggtatcgtag ccggcatcgt ggtcgcgctg accgcatgg     1680 agaagctgcc ttcgccggat ggcgacgata gcaagccgat gccgagcgcg atcggtgagc    1740
tccggaagga gtatggtctg cccatctttg cgattctcac cttggacgac atcatcgagg    1800
gtatcaaggg gctcgcatcc gaggaggaca tcaggaggac ggaggagtac cgggccaagt    1860
acaaggcgac cgactaggcg ggaggaacaa atctagattg tgcaaaccgc tctgtgaata    1920
caaaaaaaaa aaaaaaaaag ggcgtcgggg tagtgacccc acgcctgatt cgggggtaaa    1980
gcgctgtgta gcctagcgct actttggtaa gtgcatcttc tgattggaaa ggctcgaccc    2040
ccaatgtaaa gcacaagag gcaagtccag agtagaaagc gcccattatt acgtggcgcc     2100
accacccaga gacggcggcc cccaagggct acgaaatcaa ttcggcggta gcgcatagcc    2160
gtcgagattc ccagtcacgg ccggttggcc gaggtgaaat caacttctca tctgctcatg    2220
tacgtccgat ccagaattcg gttgaccagg gccgatgtcc ccagaacccc gccttgtttg    2280
tttcggggct tctttgcttc cgtgctctcg ttctaggaaa gtggcgtctt ggtttggcgt    2340
ggcaaatcgt agacctggag atggtgagat agtctgtaac agcatgcacg ggtagtcccg    2400
gccctacacc cgaggcgtag gtcaagagct cttaccatgt catgccaccc gccccctcca    2460
aactgcgcct tgctcggccc gaggtgcgtg aaccccagcc gctcatagta agacacgagg    2520
tgctacagac atggctcgtc agccagcaga tccccctaa ccaatcctta ggggcagaga     2580
gggtagtagt cactcacatc ctgacaaatc agtgccaccc ggtccaccag gccgcaattc    2640
ttcatctggt ccaaaaaggc tttgataatc atttgcccga ttccacatcg ctgtaggcgc    2700
gggagcacag cgagagagtg caacccgacg gtacgcccgg cctcctgatg gccgacgctc    2760
ttgtcaacgg tgcgtgcggc ggggttgcgc cactccttcg ggtacgccat gtcggcgtcg    2820
gtgacgacgt ccccgcggca tcgtgtcgag atgacgtggg cgagcaggac gctcacggcg    2880
ccgtcggcgc ggcccgtctc gaccggcttg gaggtaggca gcgtctcgag gccgaggttt    2940
gcggcacggt ctgggacgac ggtgaggaaa acgccgagac tgagctcggg gcagacggtg    3000
aggcggtaag cgatctgtcg gggttgcggt tagatggttg tcagcgtgtc tgttgtgtgc    3060
tccttgactg gattgggctg aggattgctt gccttttcgg gcgacgcccg atgttcgggc    3120
ttagggaacg aagcattttc cagctcgata caggatggga ggtcgttgat ggttagcggc    3180
ctgatattgg gtgaaaaggt tgagatgaac gggagtgcct tctggaggcg agattccggg    3240
ctgtccttgg ctgccctcct cttctggcac agcatctctt gaagcgaagc aaagtctccg    3300
tcgacgtctg aggactcgtc aacggcctgg tcagcctctt ggataggaca aggactctgt    3360
tcctccgaca ggccttctc ggcgcctgcc ataactgcgc cgagtcgggt gtgttctttc      3420
gcgactgcag ctagctaaga gatcgggccg tcgagccaaa ggagcttagg ttgaccggat    3480
```

```
caatgatcgc gctaggtgtg ccaaaaaccg ttaccgtctc ttgaataatt taatatgcag    3540
ctcggggctg aaacccttgc tgcaaacccg gaagtattgt ttcctggggc tagccgggtt    3600
ctcaacggct tcgttgccac acagctcgct gtccgtaatc ggcgtggagc ttttaggcgt    3660
ctaaaggttg gacgtccagg ctatgcactc agagaaacga gatgtgcgcg tagagatcca    3720
gtggcgaggt tgcgccgcga gatgctggcg agctggaacg agaagctgtg ttaccgtagt    3780
gctggaacgg tagtgtagaa tcgaatgggg ctaggagtag gagccaaggt gcaattcccc    3840
gccgcgctgc acgtctcgcc gtgttaggaa atgctacctg caggtcacaa ggctgccggg    3900
tagcatgccg tgggtgccca agcaacctat cggtatatgg agccgggcag ccggccagtc    3960
gggcagccgg gcacgccggg gtattttgaa agcctacctc aacctcaatt acttgattag    4020
aaccgaagtt caggttaagg gtgttaggtg tggctatggg attatggcgt gagaaatcag    4080
aatttaactc ttctttctac ccttgcatct ccccggtact ggtctcgacc attcctgatg    4140
acgtgcgctg gaaatactaa atggcatagt acctttcgac ctctgccagc ctccaaggaa    4200
agccccaaaa gcgttctagc agtaggccca tggcgggccg tcgcttcgca actcgcggcc    4260
cccgttgaag ctctgtggcg gggcaaagtt gcccagcccc tcctgacgtc accggcaagt    4320
gggtactgaa tttcgtttga acctcatctt cagaagacga aatacttcgt tcagattgca    4380
catacacggt agctgtacct tcttccccgg cagctccccg atcgctaggg cgttgagctt    4440
ggaatatgat caaagtcgta tgtatgtaca tacattgtag gactctcact gtccgcgaac    4500
agttacagtg aaacaagaat ggccgcgtca agtcgtaggc acaagaagcg acggcaagaa    4560
acaacctcga gcaggggtat gattttctcc gtactgctgt cagacatttg ctgcaccatt    4620
tgagatgatt ctaccgcgtg ataggagcct agtgttttgg ccgagtcgga tagaagtaac    4680
aaatttcgat tgctgcagca tggaatcgct gagggtcaac tgaatatccg cccgaactag    4740
agttccccgt tgtggtttca ccggtcaacg ccccctggcg gatctctatt ggattgcact    4800
gcaaaaatct gcacacgtag actgctgctg caccaaccgg tggtcgagcg ggttgaaaag    4860
gaacttctga cgccaaccgc aaatagaaca gtcacccaac acgaagctgt tcagaatggg    4920
cgcatgcagg gtgaagatgg aagccagatc agatggatcc tcagagtcct tcacatgtgc    4980
ggggcagagc ctccgcgatg gcttctctcg cctactcaac cttacctact acccacctag    5040
ggaagttatc agatgtaata ccttaaggta ccttctctgt agggtaaacg cttccgatg     5100 gagggttact tggagtcgtt tgagatcaca catcccgcag ccaattggtc agcaaaactc    5160
tccccgtctc tatgcagatg ggagcagttg aagtcttgcc gcagtcgggg caaaaggata    5220
ctccaagctg cgtaaatact tgacaagaca gcaagacagt cagtgcttca ttcgcgtgat    5280
gtgtcgatga agcgtacctg aggttgtctc gccgccaaag ggtccagta cttctgactg     5340 cctcgtgctg aaggtgcgtt aaaaaaaaag gtggctaccg tatccggcca ttgtccgttg    5400
cccagacttc tagggcccct ccgctcgtcg ctccgcttct tcatcccgaa cttgccgcat    5460
gcgtgtggct actcaaacag tgcatcttac ctaggtagaa attttgctga caccggttgc    5520
tcggcaagtc ttccagagtg ttccattgaa aagtggccga ggagatagaa tgcccgcatc    5580
tcgccattgg catgcaggca cactgtttgg gctctgtcgt cgttaccctg ttgttctaca    5640
ctaattgtag gccgatctac cccacgtcag cccccctgcct agattacagg tagtggggtg    5700
gcaatagccg acagcgattc ctcgcggtgg cctagaccca attacgtgca ggagggtagt    5760
gatccttgca gcctcagaat gctgggtagc agcatacttc agccttcttg aaagccaccc    5820
gtggtccctg gatctatttg caccttatta tataacctct ggagccctca tcactcggac    5880
```

```
ctcgatacag agggacgcat tcgtgcttgc ataaccgcac aatccaggcg cggatgagac      5940
tcgggccttc ttggttctct tctacaatac cgcaacaccc cctcccccac cccgaaactt      6000
ccaacagata ctgggcatat tccggccatc cttcccttcc ctccctcctg caaaccaacg      6060
agaccgcccc gagaagcaca ccaaaatgta cgcgaaaatc cgacgccctg atgtttcaga      6120
tcgaagcctg agtactgact ctccgagctc aggcgcatca cgctcagtat taccaattcg      6180
gagccccaga gcgacgacca ggacctgctg tccctggaag tgtaccccga tgacgatc       6240 gagaccttgc gcagttccat acaagccgaa accacccacc accccagcgc ccaacacctc     6300
taccacaatg gccagctggt cagcgacaac tccaagaccc tggccgagct cggcgtgact     6360
gacggcgaca tgctcgccct ccacgtccgc gacatgaggg gcagcacgac ggttccggca    6420
ggggggggca ggtcaggacg tcccgcggcg cgccagcacc agccggtgca ggatcccgaa    6480
gtgatccgtt tgcagattct gggcgacccc aacctgaggg gcgagttggc caggtcgcgg    6540
cccgacttgg tggcggcact ggaggacccc cagaggttcg cacgcctgtt cgccgacagc    6600
ctggaccggg agcggaggga gcgcgaggag cgccagcgac agattcagct gctgaattcg    6660
gacccgttcg atgtcgaggc tcaggcgaaa atcgaggaga tcatccgcca ggagcgggtc    6720
atggagaact tgcagaatgc catggagcac aaccccgaag gtaacacagg gaaacatagc    6780
ctcgcaccgc acgacgtggt cccttccaaa cccgcgctaa tccgcccgct tcccagtttt    6840
tggtaccgtg cacatgctgt atatcgaggt cgaagtcaac ggatacaagg tcaaggcgtt    6900
ggtcgactcg ggcgcgcaag ccaccatcat gagcccccag tgcgccgagg cctgcggcat    6960
catgcggctc gtcgacaagc gctttgccgg catcgcacgg ggcgtgggaa cggccaacat    7020
catcggccgc gtgcactcgg ccccgatcaa gatcggaccc ctcttccttc cttgcagctt    7080
caccgtcatg gagggcaagc aggtggaact gctgctcggc ctcgacatgc tgaagcgtca    7140
ccaggcgtgc atcgatcttg ccaaggacaa gctgattatc cagggagccg aggtgccgtt    7200
cctgggcccg gccgacattc cgaccgagac cgaggaggcc tatcagcagg agccgaccgt    7260
ccctgggccg gcgggcacga cgatcggcca gcgctccggt gccgtgcatg cgccgagcgc    7320
ggcagctcat gcggcccagt cgagcggtgg tggtccctca ggtccgcaaa gtgcagcgag    7380
accgtcgttc cccagagaac acatcgacca attgatggcg ctaggggcct ccgagcagag    7440
agccattcag gcgctggagg caaccggcgg gaacgtcgag tatgcggcca gtctgatttt    7500
ccaggactga tgctattcaa catcctctgg cccatggctt gagacgacgt taacgggtta    7560
cgaacttctc tctgaatgcg gaacgggtta taaagaaaag atttctaggc acgacctcga    7620
aagcagctcc gcatggcatt tctggaccat agctaagagt cggctctgag actacgccga    7680
gagttcgtct ggtaacagat tggtggacgg ataccaaaaa aactactgct aaggtgtgtg    7740
aagggtagtt tagagggcac ccgggaccgg ccagcgcata gcctagaatt gaca          7794
```

<210> SEQ ID NO 8
<211> LENGTH: 691
<212> TYPE: DNA
<213> ORGANISM: Neurospora crassa

<400> SEQUENCE: 8

```
atggcgctgt gccagaaccg cttgcaagag gaacggtacg ccgcaaagca ttgcgcaaca       60
gtgtacctac gtccagcaga ctgacaatct tattctctcc ctctaggaag cagtggcgaa      120
aggaccatcc ctttggcttc tatgcccgtc cccagaagaa ccagcagggt gtgctcgact      180
```

| | |
|---|---|
| tgaagatttg ggaatgtggt attccgggca agaaaagac aatctgggag ggtggtctgt | 240 |
| tcaagttgac cgtcacgttc cctgatggta tgcgccctgc accggtcggt gtctttagtc | 300 |
| agaagaatac acgtgctgac ttgacgtttc ctgcatgcag aatatcccac gaaacccccc | 360 |
| aagtgtacgc cgaaagctag ccctcgtcca tcccccttg ctacgatcac atggctaaca | 420 |
| tgttggcgtc tgagcaggca aattcgtccc ccctcttttc caccccaatg tctacccatc | 480 |
| aggcacggtc tgtctctcga tcctcaacga agaagaggca tggaagccgg ccatcacgat | 540 |
| gaagcagatc ctgctcggca tccaggactt gctcaatgac cccaatcccg agtccccagc | 600 |
| ccaggctgag gcgtacaatc tcttcaagaa agatcgtcag gaatatgaac gtcggatcaa | 660 |
| gcgcgtcgtg cgggagaatg ccgccccata g | 691 |

<210> SEQ ID NO 9
<211> LENGTH: 157
<212> TYPE: PRT
<213> ORGANISM: Neurospora crassa

<400> SEQUENCE: 9

Met Ala Leu Cys Gln Asn Arg Leu Gln Glu Glu Arg Lys Gln Trp Arg
1               5                   10                  15

Lys Asp His Pro Phe Gly Phe Tyr Ala Arg Pro Gln Lys Asn Gln Gln
            20                  25                  30

Gly Val Leu Asp Leu Lys Ile Trp Glu Cys Gly Ile Pro Gly Lys Glu
        35                  40                  45

Lys Thr Ile Trp Glu Gly Gly Leu Phe Lys Leu Thr Val Thr Phe Pro
    50                  55                  60

Asp Glu Tyr Pro Thr Lys Pro Pro Lys Cys Lys Phe Val Pro Pro Leu
65                  70                  75                  80

Phe His Pro Asn Val Tyr Pro Ser Gly Thr Val Cys Leu Ser Ile Leu
                85                  90                  95

Asn Glu Glu Glu Ala Trp Lys Pro Ala Ile Thr Met Lys Gln Ile Leu
            100                 105                 110

Leu Gly Ile Gln Asp Leu Leu Asn Asp Pro Asn Pro Glu Ser Pro Ala
        115                 120                 125

Gln Ala Glu Ala Tyr Asn Leu Phe Lys Lys Asp Arg Gln Glu Tyr Glu
    130                 135                 140

Arg Arg Ile Lys Arg Val Val Arg Glu Asn Ala Ala Pro
145                 150                 155

<210> SEQ ID NO 10
<211> LENGTH: 761
<212> TYPE: DNA
<213> ORGANISM: Aspergillus nidulans

<400> SEQUENCE: 10

| | |
|---|---|
| atgtcgctct gtttgaatcg tctgactgag gaaaggtagg ctgattgact ccttttacca | 60 |
| gcaactatat actctgttca gttctcgcag taagtcgagt tgagctgaca ggcacactcg | 120 |
| cgcacaggaa gcaatggcga aaagatcatc cttcgcctt ttatgccaag cctcatcgta | 180 |
| cggcccaggt tgtttggat atgaaacgat gggaatgtgg cattcccggg aaaaaaggga | 240 |
| caatctggga aggtggactt tcaaattgg acgtcacttt tcctgatggt gcgtggcaac | 300 |
| tctataaaag ctcaaagcga agttgttgac tgactgttct ctttcagagt accctaccaa | 360 |
| gccacccaaa tgtatgttcc tttcgtcccg ctcatactca caaatatctt tcacgagaat | 420 |
| gtcgcaagac tcttaaattg aataccgctt gcttagaagc taatgctgct gtgctgttct | 480 |

```
gggctaactt tatgtcatta tgaacaggca agttcgtgcc agctctgttt catcctaacg     540
tctacccgtc tgggactgtt tgtctgtcaa tcttgaatga agacgaagcg tggaagccgg     600
caatcacgat taaacaaatc cttcttggta tccaagactt gctcgacgac ccaaatcccg     660
agtctccagc gcaggcggaa gcatataata tgtacaagaa agacagagct gcttatgaga     720
agcgagtgaa gcaggttgtc aaggaaaacc ccgctttata a                         761
```

```
<210> SEQ ID NO 11
<211> LENGTH: 157
<212> TYPE: PRT
<213> ORGANISM: Aspergillus nidulans

<400> SEQUENCE: 11
```

Met Ser Leu Cys Leu Asn Arg Leu Thr Glu Glu Arg Lys Gln Trp Arg
1               5                   10                  15

Lys Asp His Pro Phe Ala Phe Tyr Ala Lys Pro His Arg Thr Ala Gln
            20                  25                  30

Gly Val Leu Asp Met Lys Arg Trp Glu Cys Gly Ile Pro Gly Lys Lys
        35                  40                  45

Gly Thr Ile Trp Glu Gly Gly Leu Phe Lys Leu Asp Val Thr Phe Pro
    50                  55                  60

Asp Glu Tyr Pro Thr Lys Pro Pro Lys Cys Lys Phe Val Pro Ala Leu
65                  70                  75                  80

Phe His Pro Asn Val Tyr Pro Ser Gly Thr Val Cys Leu Ser Ile Leu
                85                  90                  95

Asn Glu Asp Glu Ala Trp Lys Pro Ala Ile Thr Ile Lys Gln Ile Leu
            100                 105                 110

Leu Gly Ile Gln Asp Leu Leu Asp Asp Pro Asn Pro Glu Ser Pro Ala
        115                 120                 125

Gln Ala Glu Ala Tyr Asn Met Tyr Lys Lys Asp Arg Ala Ala Tyr Glu
    130                 135                 140

Lys Arg Val Lys Gln Val Val Lys Glu Asn Pro Ala Leu
145                 150                 155

```
<210> SEQ ID NO 12
<211> LENGTH: 477
<212> TYPE: DNA
<213> ORGANISM: Cryptococcus neoformans

<400> SEQUENCE: 12
```

```
atgagcaatt tggcccaagc gcgacttcac gaggagagga agcaatggag aaaagaccat      60
ccatttggct tctatgccag accaacaaag gcggctgatg gaaccttgaa cattatgagt     120
tgggaagttg gaataccagg gaaggctggt actgactggg aagaggtat ctacgttgtc      180 aagatgaact ttccggacga attccctaca aagcctccaa agtgcaagtt tgatcctccc     240
ctctttcatc ccaacgtcta tccctctgga acaatttgtc tctccatttt ggacgaagaa     300
aagtcttgga aaccctcgat caccgtcaag caaatctgtc ttggtatcca agatttgctt     360
gaacatgcta atgtaaatga tcctgctcag gtggaggcgt atcacatgtt caagaacgat     420
cgcacatcct atgacaagcg tatcaggcag caggctgttg aacgccgacc caagtag        477
```

```
<210> SEQ ID NO 13
<211> LENGTH: 158
<212> TYPE: PRT
<213> ORGANISM: Cryptococcus neoformans
```

<400> SEQUENCE: 13

Met Ser Asn Leu Ala Gln Ala Arg Leu His Glu Glu Arg Lys Gln Trp
1               5                   10                  15

Arg Lys Asp His Pro Phe Gly Phe Tyr Ala Arg Pro Thr Lys Ala Ala
            20                  25                  30

Asp Gly Thr Leu Asn Ile Met Ser Trp Glu Val Gly Ile Pro Gly Lys
        35                  40                  45

Ala Gly Thr Asp Trp Glu Gly Gly Ile Tyr Val Val Lys Met Asn Phe
    50                  55                  60

Pro Asp Glu Phe Pro Thr Lys Pro Pro Lys Cys Lys Phe Asp Pro Pro
65                  70                  75                  80

Leu Phe His Pro Asn Val Tyr Pro Ser Gly Thr Ile Cys Leu Ser Ile
                85                  90                  95

Leu Asp Glu Glu Lys Ser Trp Lys Pro Ser Ile Thr Val Lys Gln Ile
            100                 105                 110

Cys Leu Gly Ile Gln Asp Leu Leu Glu His Ala Asn Val Asn Asp Pro
        115                 120                 125

Ala Gln Val Glu Ala Tyr His Met Phe Lys Asn Asp Arg Thr Ser Tyr
    130                 135                 140

Asp Lys Arg Ile Arg Gln Gln Ala Val Glu Arg Pro Lys
145                 150                 155

<210> SEQ ID NO 14
<211> LENGTH: 584
<212> TYPE: DNA
<213> ORGANISM: Saccharomyces cerevisiae

<400> SEQUENCE: 14
atgagtagtt tgtgtctaca gcgtcttcag gaagaaaggt aagtagtagt tttcctcctt    60
ttatgcttac attctgtagg catacacaat ttcatccagc ggtatactaa caaatcgatg   120
aacttaactt gttttacttg aataacagaa aaaatggag aaaggatcat ccatttggat    180
tttatgccaa accagttaag aaagctgatg gtccatgga tttacagaaa tgggaagctg    240
gtatcccagg caaagaaggt acaaactggg cgggtggtgt gtacccaatt acagtcgaat   300
atccaaatga atatccttca aaacctccaa aggttaaatt tccagccgga ttttatcatc   360
caaacgtgta tccaagtggc acaatatgtt taagtatttt aaatgaagat caagattgga   420
gacccgccat cacgttaaaa caaattgttc ttggggttca ggatctttta gactctccaa   480
atccaaattc ccctgctcaa gagcctgcat ggagatcatt ttcaagaaat aaggcggaat   540
atgacaagaa agttttgctt caagctaaac agtactctaa atag                   584

<210> SEQ ID NO 15
<211> LENGTH: 157
<212> TYPE: PRT
<213> ORGANISM: Saccharomyces cerevisiae

<400> SEQUENCE: 15

Met Ser Ser Leu Cys Leu Gln Arg Leu Gln Glu Glu Arg Lys Lys Trp
1               5                   10                  15

Arg Lys Asp His Pro Phe Gly Phe Tyr Ala Lys Pro Lys Lys Ala
            20                  25                  30

Asp Gly Ser Met Asp Leu Gln Lys Trp Glu Ala Gly Ile Pro Gly Lys
        35                  40                  45

Glu Gly Thr Asn Trp Ala Gly Gly Val Tyr Pro Ile Thr Val Glu Tyr
    50                  55                  60

Pro Asn Glu Tyr Pro Ser Lys Pro Lys Val Lys Phe Pro Ala Gly
65                  70                  75                  80

Phe Tyr His Pro Asn Val Tyr Pro Ser Gly Thr Ile Cys Leu Ser Ile
            85                  90                  95

Leu Asn Glu Asp Gln Asp Trp Arg Pro Ala Ile Thr Leu Lys Gln Ile
            100                 105                 110

Val Leu Gly Val Gln Asp Leu Leu Asp Ser Pro Asn Pro Asn Ser Pro
            115                 120                 125

Ala Gln Glu Pro Ala Trp Arg Ser Phe Ser Arg Asn Lys Ala Glu Tyr
            130                 135                 140

Asp Lys Lys Val Leu Leu Gln Ala Lys Gln Tyr Ser Lys
145                 150                 155

<210> SEQ ID NO 16
<211> LENGTH: 870
<212> TYPE: PRT
<213> ORGANISM: Myceliophthora thermophila

<400> SEQUENCE: 16

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
            35                  40                  45

Trp Ala Glu Ala Tyr Ala Gln Ala Lys Ser Phe Val Ser Gln Met Thr
50                  55                  60

Leu Leu Glu Lys Val Asn Leu Thr Thr Gly Val Gly Trp Gly Ala Glu
65                  70                  75                  80

Gln Cys Val Gly Gln Val Gly Ala Ile Pro Arg Leu Gly Leu Arg Ser
            85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
            115                 120                 125

Leu Met Tyr Arg Arg Gly Tyr Ala Met Gly Gln Glu Ala Lys Gly Lys
            130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
            165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
            195                 200                 205

Arg Gln Val Pro Glu Ala Gln Gly Tyr Gly Tyr Asn Ile Ser Glu Thr
            210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
            245                 250                 255

Tyr Gln Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser

```
                275                 280                 285
Asp Trp Gln Ala Gln His Thr Gly Ala Ala Ser Ala Val Ala Gly Leu
290                 295                 300
Asp Met Ser Met Pro Gly Asp Thr Gln Phe Asn Thr Gly Val Ser Phe
305                 310                 315                 320
Trp Gly Ala Asn Leu Thr Leu Ala Val Leu Asn Gly Thr Val Pro Ala
            325                 330                 335
Tyr Arg Leu Asp Asp Met Ala Met Arg Ile Met Ala Ala Leu Phe Lys
            340                 345                 350
Val Thr Lys Thr Thr Asp Leu Glu Pro Ile Asn Phe Ser Phe Trp Thr
            355                 360                 365
Asp Asp Thr Tyr Gly Pro Ile His Trp Ala Ala Lys Gln Gly Tyr Gln
370                 375                 380
Glu Ile Asn Ser His Val Asp Val Arg Ala Asp His Gly Asn Leu Ile
385                 390                 395                 400
Arg Glu Ile Ala Ala Lys Gly Thr Val Leu Leu Lys Asn Thr Gly Ser
                405                 410                 415
Leu Pro Leu Asn Lys Pro Lys Phe Val Ala Val Ile Gly Glu Asp Ala
            420                 425                 430
Gly Ser Ser Pro Asn Gly Pro Asn Gly Cys Ser Asp Arg Gly Cys Asn
            435                 440                 445
Glu Gly Thr Leu Ala Met Gly Trp Gly Ser Gly Thr Ala Asn Tyr Pro
450                 455                 460
Tyr Leu Val Ser Pro Asp Ala Ala Leu Gln Ala Arg Ala Ile Gln Asp
465                 470                 475                 480
Gly Thr Arg Tyr Glu Ser Val Leu Ser Asn Tyr Ala Glu Glu Lys Thr
                485                 490                 495
Lys Ala Leu Val Ser Gln Ala Asn Ala Thr Ala Ile Val Phe Val Asn
            500                 505                 510
Ala Asp Ser Gly Glu Gly Tyr Ile Asn Val Asp Gly Asn Glu Gly Asp
            515                 520                 525
Arg Lys Asn Leu Thr Leu Trp Asn Asn Gly Asp Thr Leu Val Lys Asn
530                 535                 540
Val Ser Ser Trp Cys Ser Asn Thr Ile Val Val Ile His Ser Val Gly
545                 550                 555                 560
Pro Val Leu Leu Thr Asp Trp Tyr Asp Asn Pro Asn Ile Thr Ala Ile
                565                 570                 575
Leu Trp Ala Gly Leu Pro Gly Gln Glu Ser Gly Asn Ser Ile Thr Asp
            580                 585                 590
Val Leu Tyr Gly Lys Val Asn Pro Ala Ala Arg Ser Pro Phe Thr Trp
            595                 600                 605
Gly Lys Thr Arg Glu Ser Tyr Gly Ala Asp Val Leu Tyr Lys Pro Asn
610                 615                 620
Asn Gly Asn Gly Ala Pro Gln Gln Asp Phe Thr Glu Gly Val Phe Ile
625                 630                 635                 640
Asp Tyr Arg Tyr Phe Asp Lys Val Asp Asp Ser Val Ile Tyr Glu
                645                 650                 655
Phe Gly His Gly Leu Ser Tyr Thr Thr Phe Glu Tyr Ser Asn Ile Arg
            660                 665                 670
Val Val Lys Ser Asn Val Ser Glu Tyr Arg Pro Thr Thr Gly Thr Thr
            675                 680                 685
Ala Gln Ala Pro Thr Phe Gly Asn Phe Ser Thr Asp Leu Glu Asp Tyr
690                 695                 700
```

| | | | | | | | | | | | | |
|---|---|---|---|---|---|---|---|---|---|---|---|---|
|Leu|Phe|Pro|Lys|Asp|Glu|Phe|Pro|Tyr|Ile|Tyr|Gln|Tyr|Ile|Tyr|Pro|
|705| | | |710| | | |715| | | |720|

Tyr Leu Asn Thr Thr Asp Pro Arg Arg Ala Ser Ala Asp Pro His Tyr
            725                 730                 735

Gly Gln Thr Ala Glu Glu Phe Leu Pro Pro His Ala Thr Asp Asp Asp
        740                 745                 750

Pro Gln Pro Leu Leu Arg Ser Ser Gly Gly Asn Ser Pro Gly Gly Asn
        755                 760                 765

Arg Gln Leu Tyr Asp Ile Val Tyr Thr Ile Thr Ala Asp Ile Thr Asn
        770                 775                 780

Thr Gly Ser Val Val Gly Glu Glu Val Pro Gln Leu Tyr Val Ser Leu
785                 790                 795                 800

Gly Gly Pro Glu Asp Pro Lys Val Gln Leu Arg Asp Phe Asp Arg Met
            805                 810                 815

Arg Ile Glu Pro Gly Glu Thr Arg Gln Phe Thr Gly Arg Leu Thr Arg
            820                 825                 830

Arg Asp Leu Ser Asn Trp Asp Val Thr Val Gln Asp Trp Val Ile Ser
            835                 840                 845

Arg Tyr Pro Lys Thr Ala Tyr Val Gly Arg Ser Ser Arg Lys Leu Asp
850                 855                 860

Leu Lys Ile Glu Leu Pro
865                 870

<210> SEQ ID NO 17
<211> LENGTH: 4699
<212> TYPE: DNA
<213> ORGANISM: artificial sequence
<220> FEATURE:
<223> OTHER INFORMATION: expression cassette pCBH-DP1-tCBH
<220> FEATURE:
<221> NAME/KEY: misc_feature
<222> LOCATION: (3884)..(3884)
<223> OTHER INFORMATION: n is a, c, g, or t

<400> SEQUENCE: 17

```
ggtatccgat tgggaacg tcgatgaaag tattgcaaaa gtgacgagag ttgcgcaact      60
aactcgctgc cgaagaagct gcggaagaaa gagaacaccg aaagtggaat aacgttacgg     120
atgtcctgac ctcaaagttg aaaccagccc ttcctgctct atttgggaaa gcggcttgcc     180
cttgaatgcg ctgcactgtg gcacgactac cagtgatcgg gaggagcaaa ctaccctggt     240
ccgttccttg gtggggcggc actaggccca acttagggtg atcggaggtc gatgccgcgg     300
tcctcgttgg tctgggctct tctcatttcc cggtttgcac ccccgttgc acctgctgat     360 cgcccgccaa cgccgatgag gttgcgccca gaccgacaat caccgcggct gcattcccaa     420
gtatattgaa gatggcacca ggtacccggt tttgcgtccc agtcgtttgg tgccaaattt     480
gggagttttt gagcctcaag atctggggaa atcgacctca acttccatac aagttaaagt     540
cgcacacacg gcgagttcca cgaagagaca cattttttc tgaaggcctc tctcccgca     600 catcagaaac caccaaatac caagactgca gaagccgggg taagtgggcc accgggacta     660
cactaaaatg cggggagaag cgagatccgt tgcgaaggga agggatgggg tgtgctgcgg     720 cttttctccgc tctcgtgcgc cttttgcttg aatctagtgt acaccagggt aggctccgaa     780
ggagtatcta cggcagcgct gttcgtgctg cgttgagagt cagggcggag acgagcaggc     840
gacaggagcc tcgcaccggc acttcggatc gcatttgcgc ggagcgtcaa atacgctctt     900
ctgcggtcat cagagagcat cgtgaaccaa ggttcttccg cagggcggcc tgggcttcgc     960
```

```
agagtcgcac tcggcggacg ccttccgtgt caccccctgat aacctggctg ccgcgcccag    1020
actcctccaa tgaggtgtgt ggttgccctc gccgacccctt cagcaacctt aatcgcttcc    1080
atcgcacggc tccacgtcct cgaacgatgc cctcagtccg tgcccggccg tggcaaccat    1140
aacgtgacat cgccgcccag cctactagcc gctatcgacc ggttaggctt gtcaccgcag    1200
cgcccattct ccatcgggcc tctactctga tccacctcac ccaccgcaag cactagcgag    1260
cctcaccaga gtgcaagcga cacgacccgc ttggcccttc gtccttgact atctcccaga    1320
cctcttgcca tcttgccgac gccgcccccct ttttttctc ctcccctgc cggcaggtcg    1380 gtggccccag tcccgagatg gcattgctcc gttgtccatg acgacccatc attcgatggc    1440
tgactggcac actcgtcttg tttgagcatc gacgcccgc ggcccgtctc ccacggtacg    1500
gaacctcgtt gtacagtacc tctcgtaatg atacccaaca ccggggccga cgctgggag    1560 ggcggcgttc ccgagaagcc gggaaggcgg ctggccggct gacctttgtg acttggcgat    1620
ggatgcggcc atggagaatg tccgtccgaa gcgacgcgac aattagcctg gctaccatcg    1680
atataaattg ggtgattccc agctcttgat gggcgtgtct tctgcctggc agccctcgtc    1740
ttcagatcaa gcaactgtgt gctgatcctc ttccgtcatg cacgtcctct cgaccgccgt    1800
cctcctcggc agcgtcgccg tccagaaggt cctcggcagg cccggcagca gcggcctcag    1860
cgacgtcacc aagcgcagcg tcgacgactt catcagcacc gagacgccga tcgccctcaa    1920
caacctcctc tgcaacgtcg gccccgacgg ctgcagggcc ttcggcacca gcgccggcgc    1980
cgtgatcgcc agccccagca ccatcgaccc cgactactac tacatgtgga cccgcgacag    2040
cgccctcgtg ttcaagaacc tcatcgaccg cttcaccgag acgtacgacg ccggcctcca    2100
gcgccgcatc gagcagtaca tcaccgccca ggtcaccctc cagggcctca gcaaccccag    2160
cggcagcctc gccgacggca gcggcctggg cgagcccaag ttcgagctga ccctcaagcc    2220
cttcaccggc aactggggca ggccccgag ggacggcccc gccctccgcg cgatcgccct    2280
gatcggctac agcaagtggc tcatcaacaa caactaccag agcaccgtca gcaacgtcat    2340
ctggcccatc gtccgcaacg acctcaacta cgtcgcccag tattggaacc agaccggctt    2400
cgacctctgg gaggaggtca acggcagcag cttcttcacc gtcgccaacc agcaccgcgc    2460
cctggtcgag ggcgccaccc tcgccgccac cctcggccag agcggcagcg cctacagcag    2520 cgtcgcccccc caggtcctct gcttcctcca gcgcttctgg gtcagcagcg gcggctacgt    2580
cgacagcaac atcaacacca acgagggccg caccggcaag gacgtcaaca gcgtcctcac    2640
cagcatccac accttcgacc ccaacctcgg ctgcgacgcc ggcaccttcc agccctgcag    2700
cgacaaggcc ctcagcaacc tcaaggtcgt cgtcgacagc ttccgcagca tctacggcgt    2760
caacaagggc atccccgccg gcgccgccgt gccatcggc cgctacgccg aggacgtcta    2820
ctacaacggc aaccctggt acctcgccac gttcgccgcc gccgagcagc tctacgacgc    2880
catctacgtc tggaagaaga ccggcagcat caccgtcacc gccaccagcc tcgcgttctt    2940
ccaggagctg gtccccggcg tcaccgccgg cacctacagc agcagcagct cgaccttcac    3000
caacatcatc aacgccgtgt cgacctacgc cgacggcttc ctcagcgagg ccgccaagta    3060
cgtccccgcc gacggctcgc tcgccgagca gttcgaccgc aacagcggca ccccccctcag    3120 cgccctccac ctcacctggt cgtacgccag cttcctcacc gccaccgccc gcagggccgg    3180
catcgtcccc cccagctggg ccaacagcag cgcctcgacc atcccctcga cctgcagcgg    3240
cgccagcgtc gtcggcagct acagccgccc caccgccacc tcgttccccc cgagccagac    3300
```

```
ccccaagccc ggcgtccct  cgggcacccc  ctacaccccc  ctcccgtgcg  ccaccccac   3360
ctcggtcgcc gtcaccttcc acgagctggt  gagcacccag  ttcggccaga  ccgtcaaggt  3420
cgccggcaac gccgccgccc tgggcaactg  gtccaccagc  gccgccgtgg  ccctcgacgc  3480
cgtcaactac gccgacaacc accccctctg  gatcggcacc  gtcaacctcg  aggccggcga  3540
cgtcgtcgag tacaagtaca tcaacgtcgg  ccaggacggc  agcgtcacct  gggagagcga  3600
ccccaaccac acctacaccg tccccgccgt  cgcctgcgtc  acccaggtcg  tcaaggagga  3660
cacctggcag agctaagaat cggatcccta  agtaagtaaa  cgaacctctc  tgaaggaggt  3720
tctgagacac gcgcgattct tctgtatata  gttttatttt  tcactctgga  gtgcttcgct  3780
ccaccagtac ataaaccttt ttttcacgt   aacaaaatgg  cttcttttca  gaccatgtga  3840
accatcttga tgccttgacc tcttcagttc  tcactttaac  gtanttcgcg  ttagtctgta  3900
tgtcccagtt gcatgtagtt gagataaata  ccctggaag   tgggtctggg  cctttgtggg  3960
acggagccct ctttctgtgg tctggagagc  ccgctctcta  ccgcctacct  tcttaccaca  4020
gtacactact cacacattgc tgaactgacc  catcataccg  tactttatcc  tgttaattcg  4080
tggtgctgtc gactattcta tttgctcaaa  tggagagcac  attcatcggc  gcagggatac  4140
acggtttatg gaccccaaga gtgtaaggac  tattattagt  aatattatat  gcctctaggc  4200
gccttaactt caacaggcga gcactactaa  tcaacttttg  gtagacccaa  ttacaaacga  4260
ccatcgtgc  cggaaatttt gggattccgt  ccgctctccc  caaccaagct  agaagaggca  4320
acgaacagcc aatcccggtg ctaattaaat  tatatggttc  attttttta   aaaaaatttt  4380
ttcttcccat tttcctctcg cttttctttt  tcgcatcgta  gttgatcaaa  gtccaagtca  4440
agcgagctat ttgtgctata gctcggtggc  tataatcagt  acagcttaga  gaggctgtaa  4500
aggtatgata ccacagcagt attcgcgcta  taagcggcac  tcctagacta  attgttacgg  4560
tctacagaag taggtaataa aagcgttaat  tgttctaaat  actagaggca  cttagagaag  4620
ctatctaaat atatattgac cctagcttat  tatccctatt  agtaagttag  ttagctctaa  4680
cctatagata gatgcatgc                                                  4699
```

<210> SEQ ID NO 18  
<211> LENGTH: 4741  
<212> TYPE: DNA  
<213> ORGANISM: artificial sequence  
<220> FEATURE:  
<223> OTHER INFORMATION: expression cassette pCHI1-DP1-tCBH

<400> SEQUENCE: 18

```
ctgcagtccc ttacctatgg gctcctagtc tcgttcctct ttttgataga  tttgtatttt   60
gcaacgttgc aaaatgagac atttcaatca tatgtagccg ccagctactg  ttagcgtact  120
cagcgttgcc caaacggcgg ttttctgggg tagcactgtg ccgcgtgccc  ctgagccgtg  180
cgtcgcggaa acccccttaa gtagcaagta tgttaccgcc gagaccgaca  atgctgttgg  240
ttacctcgct ggtccatgat tgcaatctag atatcgtgcg gggcttttgc  aatcggtttt  300
ccctacccac tttcttcttt tggacacttt ctcttttgga aaatgccgaa  atgatgcggc  360
tcgctcacgc cccgaagtcc cgagctgggg ctagatccgt gattgcaacg  cggtgcgaac  420
gcgactgggg cagacctcgc tcagccttgg tcgtgccgga atggcgggta  cctttaccag  480
gtcgggatca attacatagg atgccatgtg cgtggatttg attgcatcgc  tgtcccttt   540
gtatgtgtcc gagagcgaga tatcaacgcg aaaaccggaa tgctcccaac  gtcgctctct  600
gttcataggg tctttttttt tcttctgctc catatcatct gtcttgaact  aagtgatcat  660
```

```
ctgctgtcac gtcccgccca atgattgtaa agaatgataa gtgatgctcg ccggggccag    720
gctctgtgaa agttccctct ttggttgacg atcaggtagc gccaacgttg attgggccgc    780
ccgtaaaatc cgaccctgtc tcctttcgtt gcaagtctcc gcgagaccgt gccaagcatg    840
ttctccggat ccctcaatta cataaggttt ggctccaggg taggtctgga agctacccac    900
ctcggccaag caaccaatca caaccagacc tcgcggcgtt tcgaccttcc tggtttgtct    960
cagggctggc caacgtcctc ccgtggcggg tgcctggtga tcgcaggtcg caggcgagtg   1020
ccgggcacgc ggagcccccg tcaaagcttg acccttcag agctaggttt cattaggcct   1080
tcgaaaacaa cccaaggccc cgtcgcaacc atcacaaccg gccgataacc agatctcggt   1140
aggtccgata aggatccaaa atggtgtcgg ctgacgttgc atgtgcccag gcaggaggat   1200
gatccccagg gttgttgccg gcagctcccg cacgtcgggg aggggagggg ggagggaaa   1260 gccctaacta acgttcgttc tatcacgggc cgaccgggcc atgctttcgg cttgtgagcg   1320
gtggggtcaa gggcaacaag aaatgctaag tgcgggacga agacacgcgg gcatgaggtc   1380
tcagggtgac ctgcgcaaaa ccaagtccca ctcgccatgc ctccagcagc aacgttgccg   1440
tagaagggtc agggggtttg ttgtagaccc acgaccatgc tgccggcgag cggagggttg   1500
gcttgctaca ggcgctgaag ggtcaactcg gtgcccaaag tggctaccaa gcgtgccatc   1560
aagggaaatg agatgatggt ggctcgtggg caaagaaaag acaagggagg tgactctaga   1620
gagatgctct cgagttcacg ggtataagag cactgtgatc gttcacaaag ccggcgtact   1680
cctctagagc atctatcatc aacatcacca gaaaggtcaa gaccaggtgg ttgccatatc   1740
cagtcgcaaa agagccaaag agcgaaggag cacgaaagca cagcccaatc attccctgct   1800
ttgctacttc ttctccacca tgcacgtcct ctcgaccgcc gtcctcctcg gcagcgtcgc   1860
cgtccagaag gtcctcggca ggcccggcag cagcggcctc agcgacgtca ccaagcgcag   1920
cgtcgacgac ttcatcagca ccgagacgcc gatcgccctc aacaacctcc tctgcaacgt   1980
cggccccgac ggctgcaggg ccttcggcac cagcgccggc gccgtgatcg ccagcccag   2040 caccatcgac cccgactact actacatgtg gacccgcgac agcgccctcg tgttcaagaa   2100
cctcatcgac cgcttcaccg agacgtacga cgccggcctc cagcgccgca tcgagcagta   2160
catcaccgcc caggtcaccc tccagggcct cagcaacccc agcggcagcc tcgccgacgg   2220
cagcggcctg ggcgagccca gttcgagct gaccctcaag cccttcaccg gcaactgggg   2280
caggccccag agggacggcc ccgccctccg cgcgatcgcc ctgatcggct acagcaagtg   2340
gctcatcaac aacaactacc agagcaccgt cagcaacgtc atctggccca tcgtccgcaa   2400
cgacctcaac tacgtcgccc agtattggaa ccagaccggc ttcgacctct gggaggaggt   2460
caacggcagc agcttcttca ccgtcgccaa ccagcaccgc gccctggtcg agggcgccac   2520
cctcgccgcc accctcggcc agagcggcag cgcctacagc agcgtcgccc ccaggtcct   2580 ctgcttcctc cagcgcttct gggtcagcag cggcggctac gtcgacagca acatcaacac   2640
caacgagggc cgcaccggca aggacgtcaa cagcgtcctc accagcatcc acaccttcga   2700
ccccaacctc ggctgcgacg ccggcaccct ccagccctgc agcgacaagg ccctcagcaa   2760
cctcaaggtc gtcgtcgaca gcttccgcag catctacggc gtcaacaagg gcatccccgc   2820
cggcgccgcc gtcgccatcg gccgctacgc cgaggacgtc tactacaacg gcaaccctg   2880 gtacctcgcc acgttcgccg ccgccagca gctctacgac gccatctacg tctgaagaa   2940 gaccggcagc atcaccgtca ccgccaccag cctcgcgttc ttccaggagc tggtccccgg   3000
```

-continued

```
cgtcaccgcc ggcacctaca gcagcagcag ctcgaccttc accaacatca tcaacgccgt   3060
gtcgacctac gccgacggct tcctcagcga ggccgccaag tacgtccccg ccgacggctc   3120
gctcgccgag cagttcgacc gcaacagcgg caccccctc agcgccctcc acctcacctg    3180
gtcgtacgcc agcttcctca ccgccaccgc ccgcagggcc ggcatcgtcc cccccagctg   3240
ggccaacagc agcgcctcga ccatcccctc gacctgcagc ggcgccagcg tcgtcggcag   3300
ctacagccgc cccaccgcca cctcgttccc ccgagccag accccaagc ccggcgtccc     3360
ctcgggcacc ccctacaccc ccctcccgtg cgccacccc acctcggtcg ccgtcacctt    3420
ccacgagctg gtgagcaccc agttcggcca gaccgtcaag gtcgccggca cgccgccgc    3480
cctgggcaac tggtccacca gcgccgccgt ggccctcgac gccgtcaact acgccgacaa   3540
ccacccctc tggatcggca ccgtcaacct cgaggccggc gacgtcgtcg agtacaagta    3600
catcaacgtc ggccaggacg gcagcgtcac ctgggagagc gaccccaacc acacctacac   3660
cgtccccgcc gtcgcctgcg tcacccaggt cgtcaaggag gacacctggc agagctaaga   3720
attcggatcc taagtaagta aacgaacctc tctgaaggag gttctgagac acgcgcgatt   3780
cttctgtata tagttttatt tttcactctg gagtgcttcg ctccaccagt acataaacct   3840
tttttttcac gtaacaaaat ggcttcttt cagaccatgt gaaccatctt gatgccttga    3900
cctcttcagt tctcacttta acgtagttcg cgtttgtctg tatgtcccag ttgcatgtag   3960
ttgagataaa taccctgga agtgggtctg ggcctttgtg ggacggagcc ctctttctgt    4020
ggtctggaga gcccgctctc taccgcctac cttcttacca cagtacacta ctcacacatt   4080
gctgaactga cccatcatac cgtactttat cctgttaatt cgtggtgctg tcgactattc   4140
tatttgctca aatggagagc acattcatcg gcgcagggat acacggttta tggaccccaa   4200
gagtgtaagg actattatta gtaatattat atgcctctag cgccttaac ttcaacaggc    4260
gagcactact aatcaacttt tggtagaccc aattacaaac gaccatacgt gccggaaatt   4320
tgggattcc gtccgctctc cccaaccaag ctagaagagg caacgaacag ccaatcccgg    4380
tgctaattaa attatatggt tcatttttt taaaaaaatt ttttcttccc attttcctct    4440
cgcttttctt tttcgcatcg tagttgatca aagtccaagt caagcgagct atttgtgcta   4500
tagctcggtg gctataatca gtacagctta gagaggctgt aaaggtatga taccacagca   4560
gtattcgcgc tataagcggc actcctagac taattgttac ggtctacaga agtaggtaat   4620
aaaagcgtta attgttctaa atactagagg cacttagaga agctatctaa atatatattg   4680
accctagctt attatcccta ttagtaagtt agttagctct aacctataga tagatgcatg   4740
c                                                                   4741
```

<210> SEQ ID NO 19
<211> LENGTH: 1899
<212> TYPE: DNA
<213> ORGANISM: artificial sequence
<220> FEATURE:
<223> OTHER INFORMATION: sequence coding for Trichoderma reesei
      glucoamylase, codon-optimized for expression in M. thermophila

<400> SEQUENCE: 19

```
atgcacgtcc tctcgaccgc cgtcctcctc ggcagcgtcg ccgtccagaa ggtcctcggc    60
aggcccggca gcagcggcct cagcgacgtc accaagcgca gcgtcgacga cttcatcagc    120
accgagacgc cgatcgccct caacaacctc ctctgcaacg tcggccccga cggctgcagg    180
gccttcggca ccagcgccgg cgccgtgatc gccagcccca gcaccatcga ccccgactac    240
```

```
tactacatgt ggacccgcga cagcgccctc gtgttcaaga acctcatcga ccgcttcacc    300
gagacgtacg acgccggcct ccagcgccgc atcgagcagt acatcaccgc ccaggtcacc    360
ctccagggcc tcagcaaccc cagcggcagc ctcgccgacg cagcggcct gggcgagccc    420 aagttcgagc tgaccctcaa gcccttcacc ggcaactggg gcaggcccca gagggacggc    480
cccgccctcc gcgcgatcgc cctgatcggc tacagcaagt ggctcatcaa caacaactac    540
cagagcaccg tcagcaacgt catctggccc atcgtccgca acgacctcaa ctacgtcgcc    600
cagtattgga accagaccgg cttcgacctc tgggaggagg tcaacggcag cagcttcttc    660
accgtcgcca accagcaccg cgccctggtc gagggcgcca ccctcgccgc caccctcggc    720
cagagcggca gcgcctacag cagcgtcgcc ccccaggtcc tctgcttcct ccagcgcttc    780
tgggtcagca gcggcggcta cgtcgacagc aacatcaaca ccaacgaggg ccgcaccggc    840
aaggacgtca acagcgtcct caccagcatc cacaccttcg accccaacct cggctgcgac    900
gccggcacct tccagccctg cagcgacaag gccctcagca acctcaaggt cgtcgtcgac    960
agcttccgca gcatctacgg cgtcaacaag ggcatccccg ccggcgccgc cgtcgccatc   1020
ggccgctacg ccgaggacgt ctactacaac ggcaacccct ggtacctcgc cacgttcgcc   1080
gccgccgagc agctctacga cgccatctac gtctggaaga agaccggcag catcaccgtc   1140
accgccacca gcctcgcgtt cttccaggag ctggtccccg gcgtcaccgc cggcacctac   1200
agcagcagca gctcgacctt caccaacatc atcaacgccc tgtcgaccta cgccgacggc   1260
ttcctcagcg aggccgccaa gtacgtcccc gccgacggct cgctcgccga gcagttcgac   1320
cgcaacagcg gcacccccct cagcgccctc cacctcacct ggtcgtacgc cagcttcctc   1380
accgccaccg cccgcagggc cggcatcgtc cccccagct gggccaacag cagcgcctcg   1440
accatcccct cgacctgcag cggcgccagc gtcgtcggca gctacagccg ccccaccgcc   1500
acctcgttcc ccccgagcca gacccccaag cccggcgtcc cctcgggcac ccctacacc   1560 cccctcccgt gcgccacccc cacctcggtc gccgtcacct ccacgagct ggtgagcacc   1620 cagttcggcc agaccgtcaa ggtcgccggc aacgccgccg ccctgggcaa ctggtccacc   1680
agcgccgccg tggccctcga cgccgtcaac tacgccgaca accacccct ctggatcggc   1740 accgtcaacc tcgaggccgg cgacgtcgtc gagtacaagt acatcaacgt cggccaggac   1800
ggcagcgtca cctgggagag cgaccccaac cacacctaca ccgtcccgc cgtcgcctgc   1860 gtcacccagg tcgtcaagga ggacacctgg cagagctaa                         1899
```

<210> SEQ ID NO 20
<211> LENGTH: 870
<212> TYPE: PRT
<213> ORGANISM: Trichoderma reesei

<400> SEQUENCE: 20

Met Lys Ala Ala Ala Leu Ser Cys Leu Phe Gly Ser Thr Leu Ala Val
1               5                   10                  15

Ala Gly Ala Ile Glu Ser Arg Lys Val His Gln Lys Pro Leu Ala Arg
            20                  25                  30

Ser Glu Pro Phe Tyr Pro Ser Pro Trp Met Asn Pro Asn Ala Asp Gly
        35                  40                  45

Trp Ala Glu Ala Tyr Ala Gln Ala Lys Ser Phe Val Ser Gln Met Thr
    50                  55                  60

Leu Leu Glu Lys Val Asn Leu Thr Thr Gly Val Gly Trp Gly Ala Glu
65                  70                  75                  80

```
Gln Cys Val Gly Gln Val Gly Ala Ile Pro Arg Leu Gly Leu Arg Ser
                85                  90                  95

Leu Cys Met His Asp Ser Pro Leu Gly Ile Arg Gly Ala Asp Tyr Asn
            100                 105                 110

Ser Ala Phe Pro Ser Gly Gln Thr Val Ala Ala Thr Trp Asp Arg Gly
        115                 120                 125

Leu Met Tyr Arg Arg Gly Tyr Ala Met Gly Gln Glu Ala Lys Gly Lys
    130                 135                 140

Gly Ile Asn Val Leu Leu Gly Pro Val Ala Gly Pro Leu Gly Arg Met
145                 150                 155                 160

Pro Glu Gly Gly Arg Asn Trp Glu Gly Phe Ala Pro Asp Pro Val Leu
                165                 170                 175

Thr Gly Ile Gly Met Ser Glu Thr Ile Lys Gly Ile Gln Asp Ala Gly
            180                 185                 190

Val Ile Ala Cys Ala Lys His Phe Ile Gly Asn Glu Gln Glu His Phe
        195                 200                 205

Arg Gln Val Pro Glu Ala Gln Gly Tyr Gly Tyr Asn Ile Ser Glu Thr
    210                 215                 220

Leu Ser Ser Asn Ile Asp Asp Lys Thr Met His Glu Leu Tyr Leu Trp
225                 230                 235                 240

Pro Phe Ala Asp Ala Val Arg Ala Gly Val Gly Ser Val Met Cys Ser
                245                 250                 255

Tyr Gln Gln Val Asn Asn Ser Tyr Ala Cys Gln Asn Ser Lys Leu Leu
            260                 265                 270

Asn Asp Leu Leu Lys Asn Glu Leu Gly Phe Gln Gly Phe Val Met Ser
        275                 280                 285

Asp Trp Gln Ala Gln His Thr Gly Ala Ala Ser Ala Val Ala Gly Leu
    290                 295                 300

Asp Met Ser Met Pro Gly Asp Thr Gln Phe Asn Thr Gly Val Ser Phe
305                 310                 315                 320

Trp Gly Ala Asn Leu Thr Leu Ala Val Leu Asn Gly Thr Val Pro Ala
                325                 330                 335

Tyr Arg Leu Asp Asp Met Ala Met Arg Ile Met Ala Ala Leu Phe Lys
            340                 345                 350

Val Thr Lys Thr Thr Asp Leu Glu Pro Ile Asn Phe Ser Phe Trp Thr
        355                 360                 365

Asp Asp Thr Tyr Gly Pro Ile His Trp Ala Ala Lys Gln Gly Tyr Gln
    370                 375                 380

Glu Ile Asn Ser His Val Asp Val Arg Ala Asp His Gly Asn Leu Ile
385                 390                 395                 400

Arg Glu Ile Ala Ala Lys Gly Thr Val Leu Leu Lys Asn Thr Gly Ser
                405                 410                 415

Leu Pro Leu Asn Lys Pro Lys Phe Val Ala Val Ile Gly Glu Asp Ala
            420                 425                 430

Gly Ser Ser Pro Asn Gly Pro Asn Gly Cys Ser Asp Arg Gly Cys Asn
        435                 440                 445

Glu Gly Thr Leu Ala Met Gly Trp Gly Ser Gly Thr Ala Asn Tyr Pro
    450                 455                 460

Tyr Leu Val Ser Pro Asp Ala Ala Leu Gln Ala Arg Ala Ile Gln Asp
465                 470                 475                 480

Gly Thr Arg Tyr Glu Ser Val Leu Ser Asn Tyr Ala Glu Glu Lys Thr
                485                 490                 495

Lys Ala Leu Val Ser Gln Ala Asn Ala Thr Ala Ile Val Phe Val Asn
```

```
                500               505               510
Ala Asp Ser Gly Glu Gly Tyr Ile Asn Val Asp Gly Asn Glu Gly Asp
            515                   520                   525

Arg Lys Asn Leu Thr Leu Trp Asn Asn Gly Asp Thr Leu Val Lys Asn
        530                   535                   540

Val Ser Ser Trp Cys Ser Asn Thr Ile Val Ile His Ser Val Gly
545                   550                   555                   560

Pro Val Leu Leu Thr Asp Trp Tyr Asp Asn Pro Asn Ile Thr Ala Ile
                565                   570                   575

Leu Trp Ala Gly Leu Pro Gly Gln Glu Ser Gly Asn Ser Ile Thr Asp
            580                   585                   590

Val Leu Tyr Gly Lys Val Asn Pro Ala Ala Arg Ser Pro Phe Thr Trp
        595                   600                   605

Gly Lys Thr Arg Glu Ser Tyr Gly Ala Asp Val Leu Tyr Lys Pro Asn
    610                   615                   620

Asn Gly Asn Gly Ala Pro Gln Gln Asp Phe Thr Glu Gly Val Phe Ile
625                   630                   635                   640

Asp Tyr Arg Tyr Phe Asp Lys Val Asp Asp Ser Val Ile Tyr Glu
                645                   650                   655

Phe Gly His Gly Leu Ser Tyr Thr Thr Phe Glu Tyr Ser Asn Ile Arg
            660                   665                   670

Val Val Lys Ser Asn Val Ser Glu Tyr Arg Pro Thr Thr Gly Thr Thr
        675                   680                   685

Ala Gln Ala Pro Thr Phe Gly Asn Phe Ser Thr Asp Leu Glu Asp Tyr
    690                   695                   700

Leu Phe Pro Lys Asp Glu Phe Pro Tyr Ile Tyr Gln Tyr Ile Tyr Pro
705                   710                   715                   720

Tyr Leu Asn Thr Thr Asp Pro Arg Arg Ala Ser Ala Asp Pro His Tyr
                725                   730                   735

Gly Gln Thr Ala Glu Glu Phe Leu Pro Pro His Ala Thr Asp Asp Asp
            740                   745                   750

Pro Gln Pro Leu Leu Arg Ser Ser Gly Gly Asn Ser Pro Gly Gly Asn
        755                   760                   765

Arg Gln Leu Tyr Asp Ile Val Tyr Thr Ile Thr Ala Asp Ile Thr Asn
    770                   775                   780

Thr Gly Ser Val Val Gly Glu Glu Val Pro Gln Leu Tyr Val Ser Leu
785                   790                   795                   800

Gly Gly Pro Glu Asp Pro Lys Val Gln Leu Arg Asp Phe Asp Arg Met
                805                   810                   815

Arg Ile Glu Pro Gly Glu Thr Arg Gln Phe Thr Gly Arg Leu Thr Arg
            820                   825                   830

Arg Asp Leu Ser Asn Trp Asp Val Thr Val Gln Asp Trp Val Ile Ser
        835                   840                   845

Arg Tyr Pro Lys Thr Ala Tyr Val Gly Arg Ser Ser Arg Lys Leu Asp
    850                   855                   860

Leu Lys Ile Glu Leu Pro
865                   870

<210> SEQ ID NO 21
<211> LENGTH: 413
<212> TYPE: PRT
<213> ORGANISM: Artificial sequence
<220> FEATURE:
<223> OTHER INFORMATION: Buttiauxella sp. phytase variant
```

<400> SEQUENCE: 21

```
Asn Asp Thr Pro Ala Ser Gly Tyr Gln Val Glu Lys Val Val Ile Leu
1               5                   10                  15
Ser Arg His Gly Val Arg Ala Pro Thr Lys Met Thr Gln Thr Met Arg
            20                  25                  30
Asp Val Thr Pro Tyr Thr Trp Pro Glu Trp Pro Val Lys Leu Gly Tyr
        35                  40                  45
Ile Thr Pro Arg Gly Glu His Leu Ile Ser Leu Met Gly Gly Phe Tyr
    50                  55                  60
Arg Gln Lys Phe Gln Gln Gly Ile Leu Pro Arg Gly Ser Cys Pro
65                  70                  75                  80
Thr Pro Asn Ser Ile Tyr Val Trp Thr Asp Val Ala Gln Arg Thr Leu
                85                  90                  95
Lys Thr Gly Glu Ala Phe Leu Ala Gly Leu Ala Pro Gln Cys Gly Leu
            100                 105                 110
Thr Ile His His Gln Gln Asn Leu Glu Lys Ala Asp Pro Leu Phe His
        115                 120                 125
Pro Val Lys Ala Gly Ile Cys Ser Met Asp Lys Thr Gln Val Gln Gln
    130                 135                 140
Ala Val Glu Lys Glu Ala Gln Thr Pro Ile Asp Asn Leu Asn Gln Arg
145                 150                 155                 160
Tyr Ile Pro Glu Leu Ala Leu Met Asn Thr Ile Leu Asn Phe Ser Lys
                165                 170                 175
Ser Pro Trp Cys Gln Lys His Ser Ala Asp Lys Pro Cys Asp Leu Ala
            180                 185                 190
Leu Ser Met Pro Ser Lys Leu Ser Ile Lys Asp Asn Gly Asn Glu Val
        195                 200                 205
Ser Leu Asp Gly Ala Ile Gly Leu Ser Ser Thr Leu Ala Glu Ile Phe
    210                 215                 220
Leu Leu Glu Tyr Ala Gln Gly Met Pro Gln Val Ala Trp Gly Asn Ile
225                 230                 235                 240
His Ser Glu Gln Glu Trp Ala Leu Leu Leu Lys Leu His Asn Val Tyr
                245                 250                 255
Phe Asp Leu Met Glu Arg Thr Pro Tyr Ile Ala Arg His Lys Gly Thr
            260                 265                 270
Pro Leu Leu Gln Ala Ile Ser Asn Ala Leu Asn Pro Asn Ala Thr Glu
        275                 280                 285
Ser Lys Leu Pro Asp Ile Ser Pro Asp Asn Lys Ile Leu Phe Ile Ala
    290                 295                 300
Gly His Asp Thr Asn Ile Ala Asn Ile Ala Gly Met Leu Asn Met Arg
305                 310                 315                 320
Trp Thr Leu Pro Gly Gln Pro Asp Asn Thr Pro Pro Gly Gly Ala Leu
                325                 330                 335
Val Phe Glu Arg Leu Ala Asp Lys Ser Gly Lys Gln Tyr Val Ser Val
            340                 345                 350
Ser Met Val Tyr Gln Thr Leu Glu Gln Leu Arg Ser Gln Thr Pro Leu
        355                 360                 365
Ser Leu Asn Gln Pro Pro Gly Ser Val Gln Leu Lys Ile Pro Gly Cys
    370                 375                 380
Asn Asp Gln Thr Ala Glu Gly Tyr Cys Pro Leu Ser Thr Phe Thr Arg
385                 390                 395                 400
Val Val Ser Gln Ser Val Glu Pro Gly Cys Gln Leu Gln
                405                 410
```

<210> SEQ ID NO 22

<400> SEQUENCE: 22

000

<210> SEQ ID NO 23
<211> LENGTH: 4179
<212> TYPE: DNA
<213> ORGANISM: artificial sequence
<220> FEATURE:
<223> OTHER INFORMATION: pGpdA-pgaIIC1

<400> SEQUENCE: 23

```
gaattcttgt atctctacac acaggctcaa atcaataaga agaacggttc gtcttttcg      60 tttatatctt gcatcgtccc aaagctattg gcgggatatt ctgtttgcag ttggctgact    120
tgaagtaatc tctgcagatc tttcgacact gaaatacgtc gagcctgctc cgcttggaag    180
cggcgaggag cctcgtcctg tcacaactac caacatggag tacgataagg ccagttccg     240 ccagctcatt aagagccagt tcatgggcgt tggcatgatg ccgtcatgc atctgtactt     300 caagtacacc aaccctcttc tgatccagtc gatcatcccg ctgaagggcg ctttcgaatc    360
gaatctggtt aagatccacg tcttcgggaa gccagcgact ggtgacctcc agcgtccctt    420
taaggctgcc aacagctttc tcagccaggg ccagcccaag accgcaaagg cctccctcca    480
gaacgccgag aagaactgga ggggtggtgt caaggaggag taagctcctt attgaagtcg    540
gaggacggag cggtgtcaag aggatattct tcgctctgta ttatagataa gatgatgagg    600
aattggaggt agcatagctt catttggatt tgctttccag gctgagactc tagcttggag    660
catagagggt ccctttggct ttcaatattc tcaagtatct cgagtttgaa cttattcccg    720 tgaaccttt attcaccaat gagcattgga atgaacatga atctgaggac tgcaatcgcc    780
atgaggtttt cgaaatacat ccggatgtcg aaggcttggg gcacctgcgt tggttgaatt    840
tagaacgtgg cactattgat catccgatag ctctgcaaag ggcgttgcac aatgcaagtc    900
aaacgttgct agcagttcca ggtggaatgt tatgatgagc attgtattaa atcaggagat    960
atagcatgat ctctagttag ctcaccacaa aagtcagacg gcgtaaccaa aagtcacaca   1020
acacaagctg taaggatttc ggcacggcta cggaagacgg agaagcccac cttcagtgga   1080
ctcgagtacc atttaattct atttgtgttt gatcgagacc taatacagcc cctacaacga   1140
ccatcaaagt cgtatagcta ccagtgagga agtggactca atcgacttc agcaacatct    1200 cctggataaa ctttaagcct aaactataca gaataagatg gtggagagct tataccgagc    1260
tcccaaatct gtccagatca tggttgaccg gtgcctggat cttcctatag aatcatcctt    1320
attcgttgac ctagctgatt ctggagtgac ccagagggtc atgacttgag cctaaaatcc    1380
gccgcctcca ccatttgtag aaaaatgtga cgaactcgtg agctctgtac agtgaccggt    1440
gactctttct ggcatgcgga gagacggacg gacgcagaga gaagggctga gtaataagcg    1500
ccactgcgcc agacagctct ggcggctctg aggtgcagtg gatgattatt aatccgggac    1560
cggccgcccc tccgcccga agtggaaagg ctggtgtgcc cctcgttgac caagaatcta    1620
ttgcatcatc ggagaatatg gagcttcatc gaatcaccgg cagtaagcga aggagaatgt    1680
gaagccaggg gtgtatagcc gtcggcgaaa tagcatgcca ttaacctagg tacagaagtc    1740
caattgcttc cgatctggta aaagattcac gagatagtac cttctccgaa gtaggtagag    1800
cgagtacccg gcgcgtaagc tccctaattg gcccatccgg catctgtagg gcgtccaaat    1860
```

```
atcgtgcctc tcctgctttg cccggtgtat gaaaccggaa aggccgctca ggagctggcc    1920
agcggcgcag accgggaaca caagctggca gtcgacccat ccggtgctct gcactcgacc    1980
tgctgaggtc cctcagtccc tggtaggcag ctttgccccg tctgtccgcc cggtgtgtcg    2040
gcggggttga caaggtcgtt gcgtcagtcc aacatttgtt gccatatttt cctgctctcc    2100
ccaccagctg ctcttttctt ttctctttct tttcccatct tcagtatatt catcttccca    2160
tccaagaacc tttatttccc ctaagtaagt actttgctac atccatactc catccttccc    2220
atcccttatt cctttgaacc tttcagttcg agctttccca cttcatcgca gcttgactaa    2280
cagctacccc gcttgagcag acatcaccat gcattccttt gcttccctcc tcgcttacgg    2340
cctcgtggct ggtgctacgt tcgcttcggc ctcccccatc gaggcccgcg acagctgcac    2400
cttcactact gccgctgccg ccaaggccgg taaggctaag tgctccacca tcaccctcaa    2460
caacatcgag gtgcccgctg cacgaccct ggacctcacc ggtctgactt cgggcaccaa    2520
ggtcatcttc gagggcacga ccactttca gtacgaggag tgggctggcc cctcatctc    2580
gatgtcgggc gagcatatca ccgtcactgg tgcctcgggc cacctcatca actgcgacgg    2640
cgctcgctgg tgggatggta agggcacctc cggtaagaag aagccgaagt tcttctacgc    2700
ccacggcctg gactccagct cgatcaccgg cctcaacatc aagaacacgc ccctcatggc    2760
cttctccgtg caggccaacg acatcacctt caccgacgtc actatcaaca acgccgacgg    2820
cgacacccag ggcggtcaca acactgacgc cttcgacgtg gtaactcgg tcggcgtcaa    2880
catcatcaag ccgtgggtcc acaaccagga cgattgcctc gcggtcaaca gcggcgagaa    2940
catctggttc actggcggca cgtgcatcgg cggtcacggc ctgagcatcg gctccgtcgg    3000
tgaccgcagc aacaacgtcg tcaagaacgt cacgatcgag cactccaccg tgtccaacag    3060
cgagaacgcc gtccggatca agaccatctc cggcgccacg ggcagcgtca gcgagatcac    3120
ctacagcaac atcgtcatga gcggcatctc cgactacggc gtcgtcatcc agcaggacta    3180
cgaggacggc aagcccaccg gtaagcccac taacggtgtg actatccagg acgtcaagct    3240
ggagagcgtg acgggtagcg tcgacagcgg cgccaccgag atctacctcc tgtgcggttc    3300
gggcagctgc tccgactgga cctgggatga cgtcaaggtg accggcggca agaagagcac    3360
tgcctgcaag aacttcccgt ccgtcgctag ctgctaagga tccacttaac gttactgaaa    3420
tcatcaaaca gcttgacgaa tctggatata agatcgttgg tgtcgatgtc agctccggag    3480
ttgagacaaa tggtgttcag gatctcgata agatacgttc atttgtccaa gcagcaaaga    3540
gtgccttcta gtgatttaat agctccatgt caacaagaat aaaacgcgtt tcgggtttac    3600
ctcttccaga tacagctcat ctgcaatgca ttaatgcatt ggacctcgca accctagtac    3660
gcccttcagg ctccggcgaa gcagaagaat agcttagcag agtctatttt cattttcggg    3720
agacgagatc aagcagatca acggtcgtca agagacctac gagactgagg aatccgctct    3780
tggctccacg cgactatata tttgtctcta attgtacttt gacatgctcc tcttctttac    3840
tctgatagct tgactatgaa aattccgtca ccagcccctg ggttcgcaaa gataattgca    3900
ctgtttcttc cttgaactct caagcctaca ggacacacat tcatcgtagg tataaacctc    3960
gaaaatcatt cctactaaga tgggtataca atagtaacca tgcatggttg cctagtgaat    4020
gctccgtaac acccaatacg ccggccgaaa cttttttaca actctcctat gagtcgttta    4080
cccagaatgc acaggtacac ttgtttagag gtaatccttc tttctagaag tcctcgtgta    4140
ctgtgtaagc gcccactcca catctccact cgaattccc                          4179
```

<210> SEQ ID NO 24
<211> LENGTH: 1089
<212> TYPE: DNA
<213> ORGANISM: artificial sequence
<220> FEATURE:
<223> OTHER INFORMATION: coding sequence for polygalacturonase II from
      A. niger which was codon optimized for expression in M.
      thermophila C1

<400> SEQUENCE: 24

```
atgcattcct tgcttccct cctcgcttac ggcctcgtgg ctggtgctac gttcgcttcg      60
gcctccccca tcgaggcccg cgacagctgc accttcacta ctgccgctgc cgccaaggcc    120
ggtaaggcta agtgctccac catcacccct aacaacatcg aggtgcccgc tggcacgacc    180
ctggacctca ccggtctgac ttcgggcacc aaggtcatct tcgagggcac gaccactttt    240
cagtacgagg agtgggctgg cccctcatc tcgatgtcgg gcgagcatat caccgtcact    300
ggtgcctcgg gccacctcat caactgcgac ggcgctcgct ggtgggatgg taagggcacc    360
tccggtaaga agaagccgaa gttcttctac gcccacggcc tggactccag ctcgatcacc    420
ggcctcaaca tcaagaacac gcccctcatg gccttctccg tgcaggccaa cgacatcacc    480
ttcaccgacg tcactatcaa caacgccgac ggcgacaccc agggcggtca caacactgac    540
gccttcgacg tgggtaactc ggtcggcgtc aacatcatca gccgtgggt ccacaaccag    600
gacgattgcc tcgcggtcaa cagcggcgag aacatctggt tcactggcgg cacgtgcatc    660
ggcggtcacg gcctgagcat cggctccgtc ggtgaccgca gcaacaacgt cgtcaagaac    720
gtcacgatcg agcactccac cgtgtccaac agcgagaacg ccgtccggat caagaccatc    780
tccggcgcca cgggcagcgt cagcgagatc acctacagca acatcgtcat gagcggcatc    840
tccgactacg gcgtcgtcat ccagcaggac tacgaggacg caagcccac cggtaagccc    900
actaacggtg tgactatcca ggacgtcaag ctggagagcg tgacgggtag cgtcgacagc    960
ggcgccaccg agatctacct cctgtgcggt tcgggcagct gctccgactg gacctgggat   1020
gacgtcaagg tgaccggcgg caagaagagc actgcctgca agaacttccc gtccgtcgct   1080
agctgctaa                                                           1089
```

<210> SEQ ID NO 25
<211> LENGTH: 362
<212> TYPE: PRT
<213> ORGANISM: Aspergillus niger

<400> SEQUENCE: 25

```
Met His Ser Phe Ala Ser Leu Leu Ala Tyr Gly Leu Val Ala Gly Ala
1               5                   10                  15

Thr Phe Ala Ser Ala Ser Pro Ile Glu Ala Arg Asp Ser Cys Thr Phe
            20                  25                  30

Thr Thr Ala Ala Ala Ala Lys Ala Gly Lys Ala Lys Cys Ser Thr Ile
        35                  40                  45

Thr Leu Asn Asn Ile Glu Val Pro Ala Gly Thr Thr Leu Asp Leu Thr
    50                  55                  60

Gly Leu Thr Ser Gly Thr Lys Val Ile Phe Glu Gly Thr Thr Thr Phe
65                  70                  75                  80

Gln Tyr Glu Glu Trp Ala Gly Pro Leu Ile Ser Met Ser Gly Glu His
                85                  90                  95

Ile Thr Val Thr Gly Ala Ser Gly His Leu Ile Asn Cys Asp Gly Ala
            100                 105                 110
```

```
Arg Trp Trp Asp Gly Lys Gly Thr Gly Lys Lys Pro Lys Phe
    115                 120                 125
Phe Tyr Ala His Gly Leu Asp Ser Ser Ile Thr Gly Leu Asn Ile
130                 135                 140
Lys Asn Thr Pro Leu Met Ala Phe Ser Val Gln Ala Asn Asp Ile Thr
145                 150                 155                 160
Phe Thr Asp Val Thr Ile Asn Asn Ala Asp Gly Asp Thr Gln Gly Gly
                165                 170                 175
His Asn Thr Asp Ala Phe Asp Val Gly Asn Ser Val Gly Val Asn Ile
            180                 185                 190
Ile Lys Pro Trp Val His Asn Gln Asp Asp Cys Leu Ala Val Asn Ser
        195                 200                 205
Gly Glu Asn Ile Trp Phe Thr Gly Gly Thr Cys Ile Gly Gly His Gly
    210                 215                 220
Leu Ser Ile Gly Ser Val Gly Asp Arg Ser Asn Asn Val Val Lys Asn
225                 230                 235                 240
Val Thr Ile Glu His Ser Thr Val Ser Asn Ser Glu Asn Ala Val Arg
                245                 250                 255
Ile Lys Thr Ile Ser Gly Ala Thr Gly Ser Val Ser Glu Ile Thr Tyr
            260                 265                 270
Ser Asn Ile Val Met Ser Gly Ile Ser Asp Tyr Gly Val Val Ile Gln
        275                 280                 285
Gln Asp Tyr Glu Asp Gly Lys Pro Thr Gly Lys Pro Thr Asn Gly Val
    290                 295                 300
Thr Ile Gln Asp Val Lys Leu Glu Ser Val Thr Gly Ser Val Asp Ser
305                 310                 315                 320
Gly Ala Thr Glu Ile Tyr Leu Leu Cys Gly Ser Gly Ser Cys Ser Asp
                325                 330                 335
Trp Thr Trp Asp Asp Val Lys Val Thr Gly Gly Lys Lys Ser Thr Ala
            340                 345                 350
Cys Lys Asn Phe Pro Ser Val Ala Ser Cys
        355                 360
```

<210> SEQ ID NO 26
<211> LENGTH: 5855
<212> TYPE: DNA
<213> ORGANISM: artificial sequence
<220> FEATURE:
<223> OTHER INFORMATION: ubc9-amds

<400> SEQUENCE: 26

| | | | | | |
|---|---|---|---|---|---|
| cccgggtggg | tgtacttgcg | ctctccctct | tggaaggctt | cccgtccttc | taccccacgt | 60 |
| gggaacagct | ggtctaagac | tatcaagccg | ccatatccgc | cgtgaaattc | gcagacatgg | 120 |
| gatgagatcg | ggggccgaat | taaacacacg | acgagcggga | gagtagcttc | atggtaagat | 180 |
| aacaacttgt | catgccgtcg | ttgagcggta | ttaaagggcc | gggttctccc | tcacgacttg | 240 |
| tctaactcgc | ttctcatacg | ctggccgatc | cttcttgaac | aagttgtagg | cttcagcctg | 300 |
| agctggtgac | tcagggttgg | ggtcgtctag | caggtcctga | ataccaagaa | ggatctgctt | 360 |
| gatcgtgatt | gcgggcttcc | atgcctcctc | ctcgttcaag | atcgaaagac | acacagtgcc | 420 |
| ggatggatag | acgttggggt | ggaaaagcgg | aggcacgaat | ttgcctgttg | aatgtggatg | 480 |
| atctggttag | cttactgtgc | gagaagtgcc | acaggggga | aaaccaaata | gcgcagaagg | 540 |
| gtggcgttgg | gaatagtacg | gcagagaggg | gaacctacac | ttcggcggct | tagtggggta | 600 |
| ttctgcgata | gaacgcgggt | tagcaggttt | gtcgcataaa | gcacccgtcg | atagacttca | 660 |

```
ctcaccatcg gggaaagtaa cgtcaagctt gaaaagcccg ccttcccaga gggtttgcgc      720
ctttccgggg ataccacact cccatcgttt gaggtcaagt gttccttgag gagtccgatg      780
cggctttgca tagaagccaa aagggtggtc tcggcgccac tgctttctgt agatagtcgc      840
gtttggggtt agtttgagga atgacacgcc ataagaggca tatgcaacgt tgtcagccac      900
atacctctcc tccgtcagac gattctggca aagcgacatt ttgggatgcg gtttcggagt      960
acgtaggtgg gctggaaccg aagttcgaaa cgaccaagaa gatcacggtc gtcacccagt     1020
tcctcaagaa ctcggccggc gagctctccg agatcaagcg gttctacgtc cagaacggca     1080
aggtcatccc caactccgag tccaccatcc cgggcgtcga gggcaactcc atcacccagg     1140
actggtgcga ccgccagaag gccgccttcg gcgacgtgac cgacttccag gacaagggcg     1200
gcatggtcca gatgggcaag gccctcgcgg ggcccatggt cctcgtcatg tccatctggg     1260
acgaccacgc cgtcaacatg ctctggctcg actccacctg gcccatcgac ggcgccggca     1320
agccgggcgc cgagcgcggt gcctgcccca ccacctcggg cgtccccgct gaggtcgagg     1380
ccgaggcccc caactccaac gtcatcttct ccaacatccg cttcggcccc atcggctcca     1440
ccgtctccgg cctgcccgac ggcggcagcg gcaaccccaa cccgcccgtc agctcgtcca     1500
ccccggtccc ctcctcgtcc accacatcct ccggttcctc cggcccgact ggcggcacgg     1560
gtgtcgctaa gcactatcta gactggaaac gcaaccctga agggattctt cctttgagag     1620
atggaagcgt gtcatatctc ttcggttcta cggcaggttt ttttctgctc tttcgtagca     1680
tggcatggtc acttcagcgc ttatttacag ttgctggtat tgattccttg tgcaaattgc     1740
tatctgacac ttattagcta tggagtcacc acatttccca gcaacttccc cacttcctct     1800
gcaatcgcca acgtcctctc ttcactgagt ctccgtccga taacctgcac tgcaaccggt     1860
gccccatggt acgcctccgg atcatactct tcctgcacga gggcatcaag ctcactaacc     1920
gccttgaaac tctcattctt cttatcgatg ttcttatccg caaaggtaac cggaacaacc     1980
acgctcgtga aatccagcag gttgatcaca gaggcatacc catagtaccg gaactggtca     2040
tgccgtaccg cagcggtagg cgtaatcggc gcgatgatgg cgtccagttc cttcccggcc     2100
ttttcttcag cctcccgcca tttctcaagg tactccatct ggtaattcca cttctggaga     2160
tgcgtgtccc agagctcgtt catgttaaca gctttgatgt tcgggttcag taggtctttg     2220
atatttggaa tcgccggctc gccggatgca ctgatatcgc gcattacgtc ggcgctgccg     2280
tcagccgcgt agatatggga gatgagatcg tggccgaaat cgtgcttgta tggcgtccac     2340
ggggtcacgg tgtgaccggc tttggcgagt gcggcgacgg tggtttccac gccgcgcagg     2400
ataggagggt gtggaaggac attgccgtcg aagttgtagt agccgatatt gagcccgccg     2460
ttcttgatct tggaggcaat aatgtccgac tcggactggc gccagggcat ggggatgacc     2520
ttggagtcgt atttccatgg ctcctgaccg aggacggatt tggtgaagag gcggaggtct     2580
aacatacttc atcagtgact gccggtctcg tatatagtat aaaaagcaag aaaggaggac     2640
agtggaggcc tggtatagag caggaaaaga aggaagaggc gaaggactca ccctcaacag     2700
agtgcgtaat cggcccgaca acgctgtgca ccgtctcctg accctccatg ctgttcgcca     2760
tctttgcata cggcagccgc ccatgactcg gccttagacc gtacaggaag ttgaacgcgg     2820
ccggcactcg aatcgagcca ccgatatccg ttcctacacc gatgacgcca ccacgaatcc     2880
caacgatcgc accctcacca ccagaactgc cgccgcacga ccagttcttg ttgcgtgggt     2940
tgacggtgcg cccgatgatg ttgttgactg tctcgcagac catcagggtc tgcgggacag     3000
```

-continued

| | | | | | |
|---|---|---|---|---|---|
| aggtcttgac | gtagaagacg | gcaccggctt | tgcggagcat | ggttgtcaga | accgagtccc | 3060 |
| cttcgtcgta | cttgtttagc | catgagatgt | agcccattga | tgtttcgtag | ccctggtggc | 3120 |
| atatgttagc | tgacaaaaag | ggacatctaa | cgacttaggg | gcaacggtgt | accttgactc | 3180 |
| gaagctggtc | tttgagagag | atggggaggc | catggagtgg | accaacgggt | ctcttgtgct | 3240 |
| ttgcgtagta | ttcatcgagt | tcccttgcct | gcgcgagagc | ggcgtcaggg | aagaactcgt | 3300 |
| gggcgcagtt | tgtctgcaca | gaagccagcg | tcagcttgat | agtcccataa | ggtggcgttg | 3360 |
| ttacatctcc | ctgagaggta | gaggggaccc | tactaactgc | tgggcgattg | ctgcccgttt | 3420 |
| acagaatgct | agcgtaactt | ccaccgaggt | caactctccg | gccgccagct | tggacacaag | 3480 |
| atctgcagcg | gaggcctctg | tgatcttcag | ttcggcctct | gaaaggatcc | ccgatttctt | 3540 |
| tgggaaatca | ataacgctgt | cttccgcagg | cagcgtctgg | actttccatt | catcagggat | 3600 |
| ggttttttgcg | aggcgggcgc | gcttatcagc | ggccagttct | tcccaggatt | gaggcattct | 3660 |
| gtgttagctt | atagtcagga | tgttggctcg | acgagtgtaa | actgggagtt | ggcatgaggg | 3720 |
| ttatgtaggc | ttctttagcc | ccgcatcccc | ctcattctcc | tcattgatcc | cggggagcg | 3780 |
| gatggtgttg | ataagagact | aattataggg | tttagctggt | gcctagctgg | tgattggctg | 3840 |
| gcttcgccga | attttacggg | ccaaggaaag | ctgcagaacc | gcggcactgg | taaacggtaa | 3900 |
| ttaagctatc | agccccatgc | taacgagttt | aaattacgtg | tattgctgat | aaacaccaac | 3960 |
| agagctttac | tgaaagatgg | gagtcacggt | gtggcttccc | cactgcgatt | attgcacaag | 4020 |
| cagcgagggc | gaacttgact | gtcgtcgctg | agcagcctgc | agtcaaacat | acatatatat | 4080 |
| caaccgcgaa | gacgtctggc | cttgtagaac | acgacgctcc | ctagcaacac | ctgccgtgtc | 4140 |
| agcctctacg | gttgttactt | gcattcagga | tgctctccag | cgggcgagct | attcaaaata | 4200 |
| ttcaaagcag | gtatctcgta | ttgccaggat | tcagctgaag | caacaggtgc | caaggaaatc | 4260 |
| tgcgtcggtt | ctcatctggg | cttgctcggt | cctggcgtag | atctagaggt | accacgacca | 4320 |
| agaagatcac | ggtcgtcacc | cagttcctca | agaactcggc | cggcgagctc | tccgagatca | 4380 |
| agcggttcta | cgtccagaac | ggcaaggtca | tccccaactc | cgagtccacc | atcccgggcg | 4440 |
| tcgagggcaa | ctccatcacc | caggactggt | gcgaccgcca | gaaggccgcc | ttcggcgacg | 4500 |
| tgaccgactt | ccaggacaag | ggcggcatgg | tccagatggg | caaggccctc | gcggggccca | 4560 |
| tggtcctcgt | catgtccatc | tgggacgacc | acgccgtcaa | catgctctgg | ctcgactcca | 4620 |
| cctggcccat | cgacggcgcc | ggcaagccgg | gcgccgagcg | cggtgcctgc | ccaccacct | 4680 |
| cgggcgtccc | cgctgaggtc | gaggccgagg | ccccaactc | caacgtcatc | ttctccaaca | 4740 |
| tccgcttcgg | ccccatcggc | tccaccgtct | ccggcctgcc | cgacggcggc | agcggcaacc | 4800 |
| ccaaccgcc | cgtcagctcg | tccacccgg | tcccctcctc | gtccaccaca | tcctccggtt | 4860 |
| cctccggccc | gactggcggc | acgggtgtcg | ctaagcacta | ttcgaaaagg | ctgggttgac | 4920 |
| ggcgagaggg | ttgagaaggt | tgggaggag | aggggaagag | gagaaggtag | tgaggcgggg | 4980 |
| agaacaaggt | ctgaggtatt | taaaggatag | tgaggtaggc | aaattaaggt | cggccgtgaa | 5040 |
| tgcgcagacg | aagtaacact | gtcttgggcg | tgcagctgct | catcgctggg | tttgatgccc | 5100 |
| cacagccaat | cagtccccgg | cggcgctgca | ggttatcgct | gtcacatgac | ctcatagatc | 5160 |
| cgcatcgaac | tacgtacttg | ggtcgatatg | tccatcagcc | cgtcttcgat | ttactaaatt | 5220 |
| cctttgcctt | gggttacagg | accaatggaa | tcttccatgt | gtccttgcat | tgtacattgt | 5280 |
| agtttattgg | gtagacacag | cttacatgca | gtaaatagtt | cagaagatcg | ccgtgagcca | 5340 |
| gctcaaagca | catagtagaa | gataccaatg | ccccaacgag | ggaactttac | tggcactaag | 5400 |

```
tgacagctat tttagactct ccaaccacga cggcaacttc ctcacctttg ttgcgtagct    5460
gcgttatggt aacggcgaat attttttgtc aaggtgaata atcatctcg tacaacttgc    5520 gttgaggttg tgaatttaga ccacaatcac tgtgcaagga gccgtccgaa cccatttctg    5580
ggagccagtc taattcacgc ttgatgctac atgacttcaa agtagtatag atacccatag    5640
gataaaccat gctacctggt tcttaagcac taatggtaat acaaacagtg acctggttaa    5700
taagtgggag ttgttggaag gtatccattc tcatagtagt cttgttgtgg cactccagac    5760
gaacatgcta gatatggata gatgtgagac aaatgtctct cgcttgtatt cttcagttca    5820
aaacttgtga ggtatcatat acagagttcc ttccc                              5855

<210> SEQ ID NO 27
<211> LENGTH: 21
<212> TYPE: DNA
<213> ORGANISM: artificial sequence
<220> FEATURE:
<223> OTHER INFORMATION: ubc9P1f primer

<400> SEQUENCE: 27
gatagtgctt agcgacaccc g                                             21

<210> SEQ ID NO 28
<211> LENGTH: 20
<212> TYPE: DNA
<213> ORGANISM: artificial sequence
<220> FEATURE:
<223> OTHER INFORMATION: ubc9P1r primer

<400> SEQUENCE: 28
tcggccacaa atctcagtga                                               20

<210> SEQ ID NO 29
<211> LENGTH: 5268
<212> TYPE: DNA
<213> ORGANISM: artificial sequence
<220> FEATURE:
<223> OTHER INFORMATION: pLH937 plasmid

<400> SEQUENCE: 29
cgtattgggc gctcttccgc ttcctcgctc actgactcgc tgcgctcggt cgttcggctg    60
cggcgagcgg tatcagctca ctcaaaggcg gtaatacggt tatccacaga atcaggggat    120
aacgcaggaa agaacatgtg agcaaaaggc cagcaaaagg ccaggaaccg taaaaaggcc    180
gcgttgctgg cgtttttcca taggctccgc cccctgacg agcatcacaa aaatcgacgc    240
tcaagtcaga ggtggcgaaa cccgacagga ctataaagat accaggcgtt ccccctgga    300 agctccctcg tgcgctctcc tgttccgacc ctgccgctta ccggatacct gtccgccttt    360
ctcccttcgg gaagcgtggc gctttctcat agctcacgct gtaggtatct cagttcggtg    420
taggtcgttc gctccaagct gggctgtgtg cacgaacccc ccgttcagcc cgaccgctgc    480
gccttatccg gtaactatcg tcttgagtcc aacccggtaa gacacgactt atcgccactg    540
gcagcagcca ctggtaacag gattagcaga gcgaggtatg taggcggtgc tacagagttc    600
ttgaagtggt ggcctaacta cggctacact agaaggacag tatttggtat ctgcgctctg    660
ctgaagccag ttaccttcgg aaaaagagtt ggtagctctt gatccggcaa acaaaccacc    720
gctggtagcg gtggtttttt tgtttgcaag cagcagatta cgcgcagaaa aaaaggatct    780
caagaagatc ctttgatctt ttctacgggg tctgacgctc agtggaacga aaactcacgt    840
```

```
taagggattt tggtcatgag attatcaaaa aggatcttca cctagatcct tttaaattaa    900
aaatgaagtt ttaaatcaat ctaaagtata tatgagtaaa cttggtctga cagttaccaa    960
tgcttaatca gtgaggcacc tatctcagcg atctgtctat ttcgttcatc catagttgcc   1020
tgactcccg tcgtgtagat aactacgata cgggagggct taccatctgg ccccagtgct   1080
gcaatgatac cgcgagaccc acgctcaccg gctccagatt tatcagcaat aaaccagcca   1140
gccggaaggg ccgagcgcag aagtggtcct gcaactttat ccgcctccat ccagtctatt   1200
aattgttgcc gggaagctag agtaagtagt tcgccagtta atagtttgcg caacgttgtt   1260
gccattgcta caggcatcgt ggtgtcacgc tcgtcgtttg gtatggcttc attcagctcc   1320
ggttcccaac gatcaaggcg agttacatga tcccccatgt tgtgcaaaaa agcggttagc   1380
tccttcggtc ctccgatcgt tgtcagaagt aagttggccg cagtgttatc actcatggtt   1440
atggcagcac tgcataattc tcttactgtc atgccatccg taagatgctt ttctgtgact   1500
ggtgagtact caaccaagtc attctgagaa tagtgtatgc ggcgaccgag ttgctcttgc   1560
ccggcgtcaa tacgggataa taccgcgcca catagcagaa ctttaaaagt gctcatcatt   1620
ggaaaacgtt cttcggggcg aaaactctca aggatcttac cgctgttgag atccagttcg   1680
atgtaaccca ctcgtgcacc caactgatct tcagcatctt ttactttcac cagcgtttct   1740
gggtgagcaa aaacaggaag gcaaaatgcc gcaaaaaagg gaataagggc gacacggaaa   1800
tgttgaatac tcatactctt cctttttcaa tattattgaa gcatttatca gggttattgt   1860
ctcatgagcg gatacatatt tgaatgtatt tagaaaaata aacaaatagg ggttccgcgc   1920
acatttcccc gaaaagtgcc acctggatat cccagttgca ggtggtcgac ctgcagactg   1980
gctgtgtata agggagcctg acatttatat tccccagaac atcaggttaa tggcgttttt   2040
gatgtcattt tcgcggtggc tgagatcagc cacttcttcc ccgataacgg agaccggcac   2100
actggccata tcggtggtca tcatgcgcca gctttcatcc ccgatatgca ccaccgggta   2160
aagttcacgg gagactttat ctgacagcag acgtgcactg gccaggggga tcaccatccg   2220
tcgcccgggc gtgtcaataa tatcactctg tacatccaca aacagacgat aacggctctc   2280
tcttttatag gtgtaaacct aaactgcatt tcaccagcc cctgttctcg tcagcaaaag   2340
agccgttcat ttcaataaac cgggcgacct cagccatccc ttcctgattt ccgctttcc   2400
agcgttcggc acgcagacga cgggcttcat tctgcatggt tgtgcttacc agaccggaga   2460
tattgacatc atatatgcct tgagcaactg atagctgtcg ctgtcaactg tcactgtaat   2520
acgctgcttc atagcatacc tctttttgac atacttcggg tatacatatc agtatatatt   2580
cttataccgc aaaaatcagc ggatcctcta gctagaaaga aggattacct ctaaacaagt   2640
gtacctgtgc attctgggta acgactcat aggagagttg taaaaaagtt tcggccggcg   2700
tattgggtgt tacggagcat tcactaggca accatggtta ctattgtata cccatcttag   2760
taggaatgat tttcgaggtt tatacctacg atgaatgtgt gtcctgtagg cttgagagtt   2820
caaggaagaa acagtgcaat tatctttgcg aacccagggg ctggtgacgg aattttcata   2880
gtcaagctat cagagtaaag aagaggagca tgtcaaagta caattagaga caaatatata   2940
gtcgcgtgga gccaagagcg gattcctcag tctcgtaggt ctcttgacga ccgttgatct   3000
gcttgatctc gtctcccgaa aatgaaaata gactctgcta agctattctt ctgcttcgcc   3060
ggagcctgaa gggcgtacta gggttgcgag gtccaatgca ttaatgcatt gcagatgagc   3120
tgtatctgga agaggtaaac ccgaaacgcg ttttattctt gttgacatgg agctattaaa   3180
tcactagaag gcactctttg ctgcttggac aaatgaacgt atcttatcga gatcctgaac   3240
```

-continued

```
accatttgtc tcaactccgg agctgacatc gacaccaacg atcttatatc cagattcgtc    3300
aagctgtttg atgatttcag taacgttaag tggatcccgg tcggcatcta ctctattcct    3360
ttgccctcgg acgagtgctg gggcgtcggt ttccactatc ggcgagtact tctacacagc    3420
catcggtcca gacggccgcg cttctgcggg cgatttgtgt acgcccgaca gtcccggctc    3480
cggatcggac gattgcgtcg catcgaccct gcgcccaagc tgcatcatcg aaattgccgt    3540
caaccaagct ctgatagagt tggtcaagac caatgcggag catatacgcc cggaggcgcg    3600
gcgatcctgc aagctccgga tgcctccgct cgaagtagcg cgtctgctgc tccatacaag    3660
ccaaccacgg cctccagaag aagatgttgg cgacctcgta ttgggaatcc ccgaacatcg    3720
cctcgctcca gtcaatgacc gctgttatgc ggccattgtc cgtcaggaca ttgttggagc    3780
cgaaatccgc gtgcacgagg tgccggactt cggggcagtc ctcggcccaa gcatcagct    3840 catcgagagc ctgcgcgacg gacgcactga cggtgtcgtc catcacagtt tgccagtgat    3900
acacatgggg atcagcaatc gcgcatatga aatcacgcca tgtagtgtat tgaccgattc    3960
cttgcggtcc gaatgggccg aacccgctcg tctggctaag atcggccgca gcgatcgcat    4020
ccatggcctc cgccgaccgg ctgcagaacag cgggcagttc ggtttcaggc aggtcttgca    4080
acgtgacacc ctgtgcacgg cgggagatgc aataggtcag gctctcgctg aattccccaa    4140
tgtcaagcac ttccggaatc gggagcgcgg ccgatgcaaa gtgccgataa acataacgat    4200
ctttgtagaa accatcggcg cagctattta cccgcaggac atatccacgc cctcctacat    4260
cgaagctgaa agcacgagat tcttcgccct ccgagagctg catcaggtcg agacgctgt     4320 cgaacttttc gatcagaaac ttctcgacag acgtcgcggt gagttcaggc tttttcatat    4380
gggtacctga aacatcttg ttgccctgct ttccgtgcga aatactaccg gtactttt      4440 gaaacaaggg aacaggaggg cgctgctgtg cgcggttctg agtgttcagg attgaagctg    4500
aagaaggtgc tgaggaagcg tagaactgtt gcggacgcga gttctgagaa gagctgtacc    4560
gattggtgaa agccgaagaa gtgagttggt gccctgttgc ctggataatg tttgcaactc    4620
gctggttctg cagagacgga gacaaatgct ggctacgatg ttgctgattc aggttgatac    4680
ctcggtcgag atactgtttt ggtttgatag ggtggatttg gttgcagaga agaagaaagg    4740
aaggtcaaag agggaaaact gggcggaggg aaggattttg tatcaggcag caaactgcca    4800
ctgcagtggc cctggcagtg ccgggcgagg cacccacgca cggccgcgca accggttggt    4860
ccttgcccac cacgaaaccc ttctgaaagg tcagatggaa gtgtgcgaca gtgcgcgtcc    4920
ccaagccaat gcaggcgcca tggatccact ccccacccgc aagatttcac tgtgcgttct    4980
tattggttgc cgcaaggcca gccaaggggg gaagtatgag tcacagcacc gatacaagaa    5040
aattgcagaa ctaacatatg gatgcgcgcg ctattctgta gagctctggg caaagcacca    5100
atcctgcggg tcggtacaca cactagcact gccccacctg aggcagtcag ccccgctgac    5160
cgaattgcca agagccaatg gagacggaaa gccaacgctg atggagcacc atctgaatgg    5220
acctcgctcg cttgcctgga agggacaagg gacaccggag acgcggcc               5268
```

<210> SEQ ID NO 30
<211> LENGTH: 23
<212> TYPE: DNA
<213> ORGANISM: Trichoderma reesei

<400> SEQUENCE: 30
gcagttcgac gcttacccac cgg    23

<210> SEQ ID NO 31
<211> LENGTH: 23
<212> TYPE: DNA
<213> ORGANISM: Trichoderma reesei

<400> SEQUENCE: 31
cgacgcttac ccaccgggtg agg                                                 23

<210> SEQ ID NO 32
<211> LENGTH: 23
<212> TYPE: DNA
<213> ORGANISM: Trichoderma reesei

<400> SEQUENCE: 32
gcgcgactac catcacgtct cgg                                                 23

<210> SEQ ID NO 33
<211> LENGTH: 413
<212> TYPE: PRT
<213> ORGANISM: artificial sequence
<220> FEATURE:
<223> OTHER INFORMATION: Buttiauxella sp. phytase variant

<400> SEQUENCE: 33

Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
            20                  25                  30

Asp Val Thr Pro Asn Thr Trp Pro Glu Trp Pro Val Lys Leu Gly Tyr
        35                  40                  45

Ile Thr Pro Arg Gly Glu His Leu Ile Ser Leu Met Gly Gly Phe Tyr
    50                  55                  60

Arg Gln Lys Phe Gln Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr

```
              260                 265                 270
Pro Leu Leu Gln Ala Ile Ser Asn Ala Leu Asn Pro Asn Ala Thr Glu
            275                 280                 285

Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410
```

<210> SEQ ID NO 34
<211> LENGTH: 21
<212> TYPE: DNA
<213> ORGANISM: artificial sequence
<220> FEATURE:
<223> OTHER INFORMATION: nik1 2kb F primer

<400> SEQUENCE: 34
gccatgaacc tcaccacaca g                                           21

<210> SEQ ID NO 35
<211> LENGTH: 21
<212> TYPE: DNA
<213> ORGANISM: artificial sequence
<220> FEATURE:
<223> OTHER INFORMATION: nik1 2kb R primer

<400> SEQUENCE: 35
cggcgtggcc ctgttctcga g                                           21

<210> SEQ ID NO 36
<211> LENGTH: 23
<212> TYPE: DNA
<213> ORGANISM: artificial sequence
<220> FEATURE:
<223> OTHER INFORMATION: 3078 primer

<400> SEQUENCE: 36
aagagatctc tgccctccca ggg                                         23

<210> SEQ ID NO 37
<211> LENGTH: 19
<212> TYPE: DNA
<213> ORGANISM: artificial sequence
<220> FEATURE:
<223> OTHER INFORMATION: 3079 primer

<400> SEQUENCE: 37
gtgatggccg gcttccagg                                              19

<210> SEQ ID NO 38

```
<211> LENGTH: 21
<212> TYPE: DNA
<213> ORGANISM: artificial sequence
<220> FEATURE:
<223> OTHER INFORMATION: 3145 primer

<400> SEQUENCE: 38
ctttgccctc ggacgagtgc t                                              21

<210> SEQ ID NO 39
<211> LENGTH: 23
<212> TYPE: DNA
<213> ORGANISM: artificial sequence
<220> FEATURE:
<223> OTHER INFORMATION: 3146 primer

<400> SEQUENCE: 39
ctgaactcac cgcgacgtct gtc                                            23

<210> SEQ ID NO 40

<400> SEQUENCE: 40

000

<210> SEQ ID NO 41
<211> LENGTH: 20
<212> TYPE: DNA
<213> ORGANISM: artificial sequence
<220> FEATURE:
<223> OTHER INFORMATION: 3148 primer

<400> SEQUENCE: 41
gtgtgcgaca gtgcgcgtcc                                                20

<210> SEQ ID NO 42
<211> LENGTH: 17
<212> TYPE: PRT
<213> ORGANISM: artificial sequence
<220> FEATURE:
<223> OTHER INFORMATION: motif 1

<400> SEQUENCE: 42

Arg Leu Gln Glu Glu Arg Lys Gln Trp Arg Lys Asp His Pro Phe Gly
1               5                   10                  15

Phe

<210> SEQ ID NO 43
<211> LENGTH: 27
<212> TYPE: PRT
<213> ORGANISM: artificial sequence
<220> FEATURE:
<223> OTHER INFORMATION: motif 2

<400> SEQUENCE: 43

Lys Pro Pro Lys Cys Lys Phe Thr Pro Pro Leu Phe His Pro Asn Val
1               5                   10                  15

Tyr Pro Ser Gly Thr Val Cys Leu Ser Ile Leu
            20                  25

<210> SEQ ID NO 44
<211> LENGTH: 27
<212> TYPE: PRT
<213> ORGANISM: artificial sequence
<220> FEATURE:
<223> OTHER INFORMATION: consensus 2
```

<400> SEQUENCE: 44

Lys Pro Pro Lys Cys Lys Phe Val Pro Pro Leu Phe His Pro Asn Val
1               5                   10                  15

Tyr Pro Ser Gly Thr Val Cys Leu Ser Ile Leu
            20                  25

<210> SEQ ID NO 45
<211> LENGTH: 2758
<212> TYPE: DNA
<213> ORGANISM: Aspergillus niger

<400> SEQUENCE: 45

| | | | | | |
|---|---|---|---|---|---|
| tagcgggaag | gaactctgta | tatgatacct | cacaagtttt | gaactgaaga | atacaagcga | 60 |
| gagacatttg | tctcacatct | atccatatct | agcatgttcg | tctggagtgc | acaacaaga | 120 |
| ctactatgag | aatggatacc | ttccaacaac | tcccacttat | taaccaggtc | actgtttgta | 180 |
| ttaccattag | tgcttaagaa | ccaggtagca | tggtttatcc | tatgggtatc | tatactactt | 240 |
| tgaagtcatg | tagcatcaag | cgtgaattag | actggctccc | agaaatgggt | tcggacggct | 300 |
| ccttgcacag | tgattgtggt | ctaaattcac | aaccctcaacg | caagttgtac | gagatgattt | 360 |
| attcaccttg | acaaaaaata | ttcgccgtta | ccataacgca | gctacgcaat | aaaggtgagg | 420 |
| aagttgccgt | cgtggttgga | gagtctaaaa | tagctgtcac | ttagtgccag | taaagttccc | 480 |
| tcgttgggggc | attggtatct | tctactatgt | gctttgagct | ggctcacggc | gatcttctga | 540 |
| actatttact | gcatgtaagc | tgtgtctacc | caataaacta | caatgtacaa | tgcaaggaca | 600 |
| catggaagat | tccattggtc | ctgtaaccca | aggcaaagga | atttagtaaa | tcgaagacgg | 660 |
| gctgatggac | atatcgaccc | aagtacgtag | ttcgatgcgg | atctatgagg | tcatgtgaca | 720 |
| gcgataaacct | gcagcgccgc | cggggactga | ttggctgtgg | ggcatcaaac | ccagcgatga | 780 |
| gcagctgcac | gcccaagaca | gtgttacttc | gtctgcgcat | tcacggccga | ccttaatttg | 840 |
| cctacctcac | tatcctttaa | atacctcaga | ccttgttctc | cccgcctcac | taccttctcc | 900 |
| tcttccctc | tccctcccaa | ccttctcaac | cctctcgccg | tcaacccagc | ttcttcggt | 960 |
| tccagcccac | ctacgtactc | cgaaaccgca | tcccaaaatg | tcgctttgcc | agaatcgtct | 1020 |
| gacggaggag | aggtatgtgg | ctgacaacgt | tgcatatgcc | tcttatggcg | tgtcattcct | 1080 |
| caaactaacc | ccaaacgcga | ctatctacag | aaagcagtgg | cgccgagacc | acccttttgg | 1140 |
| cttctatgca | aagccgcatc | ggactcctca | aggaacactt | gacctcaaac | gatgggagtg | 1200 |
| tggtatcccc | ggaaaggcgc | aaaccctctg | ggaaggcggg | cttttcaagc | ttgacgttac | 1260 |
| tttccccgat | ggtgagtgaa | gtctatcgac | gggtgcttta | tgcgacaaac | ctgctaaccc | 1320 |
| gcgttctatc | gcagaatacc | ccactaagcc | gccgaagtgt | aggttcccct | ctctgccgta | 1380 |
| ctattcccaa | cgccaccctt | ctgcgctatt | tggttttccc | ccctgtggca | cttctcgcac | 1440 |
| agtaagctaa | ccagatcatc | cacattcaac | aggcaaattc | gtgcctccgc | ttttccaccc | 1500 |
| caacgtctat | ccatccggca | ctgtgtgtct | ttcgatcttg | aacgaggagg | aggcatggaa | 1560 |
| gcccgcaatc | acgatcaagc | agatccttct | tggtattcag | gacctgctag | acgaccccaa | 1620 |
| ccctgagtca | ccagctcagg | ctgaagccta | caacttgttc | aagaaggatc | ggccagcgta | 1680 |
| tgagaagcga | gttagacaag | tcgtgaggga | gaacccggcc | ctttaatacc | gctcaacgac | 1740 |
| ggcatgacaa | gttgttatct | taccatgaag | ctactctccc | gctcgtcgtg | tgtttaattc | 1800 |
| ggccccgat | ctcatcccat | gtctgcgaat | ttcacggcgg | atatggcggc | ttgatagtct | 1860 |

```
tagaccagct gttcccacgt ggggtagaag gacgggaagc cttccaagag ggagagcgca    1920
agtacaccca cccgggattt cacgataatg ctgagcgcgc cattcctgtc aaacgggttt    1980
cgaaatgtcg cattggcgca ggtgtgtctt cactaattcc tgtcttggag ggtgtcgaat    2040
actcgggttt cttcttagcg agcagcgtgg cgtacataga actgacaaaa ctgggcggtt    2100
cgggacggcg tttgacactc taatgcgatt tatctagctt atgtctcttc tttctcttgg    2160
gatgctcgca cacttctacg tctaccatag ggggtgcatg ttggtgaccg atttcggat     2220
gatcatacca tagaaagacg gcttgtgccc cctgggtggg gggaagggtc ctctctaatc    2280
gactccaact caaagtgtct ccaatctgtc atccttagtg cgtaaaagta aaacaagttc    2340
cagaaagatc aaaaatctgg agaaagtact tttagtagaa aatgtggggg atgtgcaggc    2400
tgtgaaggga aaatggacaa cagttgaacg ttgggaccag agaccagacc caacctgtca    2460
gggcacaacc aataaggatg acatagaaag aaagtaaccg ttgcagaaat tcagtttctg    2520
tgtacgagtt tcgcggctat cttatcggaa gtgagtcact gagatttgtg gccgaaatcg    2580
cccctcgggt tccgccccgc cgccgcgaac gggtgtcgct tttccaatcc atatttaaga    2640
tttcccgctt catctctctc tcttccccctt ggtctcctat cttcgattag tcaattgctt    2700
cctttctttt cccttttgct gtctacttga gtcggttggt caattgatcg tagtcagc     2758
```

<210> SEQ ID NO 46
<211> LENGTH: 183
<212> TYPE: PRT
<213> ORGANISM: Aspergillus niger

<400> SEQUENCE: 46

Met Ser Leu Cys Gln Asn Arg Leu Thr Glu Glu Arg Tyr Val Ala Asp
1               5                   10                  15

Asn Val Ala Tyr Ala Ser Tyr Gly Val Ser Phe Leu Lys Leu Thr Pro
            20                  25                  30

Asn Ala Thr Ile Tyr Arg Lys Gln Trp Arg Arg Asp His Pro Phe Gly
        35                  40                  45

Phe Tyr Ala Lys Pro His Arg Thr Pro Gln Gly Thr Leu Asp Leu Lys
    50                  55                  60

Arg Trp Glu Cys Gly Ile Pro Gly Lys Ala Gln Thr Leu Trp Glu Gly
65                  70                  75                  80

Gly Leu Phe Lys Leu Asp Val Thr Phe Pro Asp Glu Tyr Pro Thr Lys
                85                  90                  95

Pro Pro Lys Cys Lys Phe Val Pro Pro Leu Phe His Pro Asn Val Tyr
            100                 105                 110

Pro Ser Gly Thr Val Cys Leu Ser Ile Leu Asn Glu Glu Ala Trp
        115                 120                 125

Lys Pro Ala Ile Thr Ile Lys Gln Ile Leu Leu Gly Ile Gln Asp Leu
    130                 135                 140

Leu Asp Asp Pro Asn Pro Glu Ser Pro Ala Gln Ala Glu Ala Tyr Asn
145                 150                 155                 160

Leu Phe Lys Lys Asp Arg Pro Ala Tyr Glu Lys Arg Val Arg Gln Val
                165                 170                 175

Val Arg Glu Asn Pro Ala Leu
            180

<210> SEQ ID NO 47
<211> LENGTH: 500
<212> TYPE: DNA
<213> ORGANISM: Trichoderma reesei

<400> SEQUENCE: 47

```
gtccgctgta ggcctcgctc cccaggcctg tgcagccctg tagcctggtc cctgcaccgc        60
tacaccgtcg cgcgctgccc cgccgccgca ggtcatcaag tgaccgggac atggaggctc       120
ttttcgctac gattgactgc aagggaccga cgggactcaa gagatctctg ccctcccagg       180
gaatcgcact aggcagatcg cggcgctatc cgcagcctcg cctttatccc gggcttcttt       240
ttccatccat ttttaatccg actgtttgcc tcttctatca tcttccgcca ttctaattca       300
cgccctgggt ttgtgttgtc cctcttcttt cttccctcac gagattctca acaacgacaa       360
ggcgttttc ctttcttcat ccgtgcaaga tccgtcgtca cctgcagcag gcagttcgac        420
gcttacccac cgggtgaggc agcgcgacta ccatcacgtc tcgggatccg ttgttggaca       480
atattgtcta gcagtccacc                                                   500
```

<210> SEQ ID NO 48
<211> LENGTH: 672
<212> TYPE: DNA
<213> ORGANISM: Trichoderma reesei

<400> SEQUENCE: 48

```
atggctcttt gccagaacag gttacaggag gagcggtagg cgatgcagac tcttcacagc        60
gcctcagatg gatccacgat gctgacggat acccaaccct tagcaagcaa tggcgacgtg       120
accacccgtt cggattcttt gccaaaccgt cccggacaaa ggagggcgtg ctcgacctga       180
agaactggga atgcggaatt ccgggcaagg aaaagacgat ctgggaggga gggttgttca       240
agctcaacat tgcgtttccc gacggtgagt gctcgccgtg cctaataacg tcttggttgg       300
gcagaaactg acatcagtcc cgtttgtcca gagtacccaa caaagccgcc gaaatgtgag       360
tacagacatc gatcccaggt gctttacggt gtcaatcggt atctaactgt actggcaggc       420
aaatttgtcc ctccgctgtt ccatcccaac gtctacccct cgggcaccgt ctgcctgtcg       480
attctcaacg aggaagaggc ctggaagccg gccatcacgg tcaagcagat tcttctgggc       540
atccaagacc tgctcaacga ccccaacccc gagtcgcccg cccaagccga cgcctacaat       600
ctgttcaaga aagacaagat cgagtacgaa aagcgcatcc ggcgcgtagt tcgcgagaat       660
ccggcgccgt aa                                                            672
```

<210> SEQ ID NO 49
<211> LENGTH: 474
<212> TYPE: DNA
<213> ORGANISM: Trichoderma reesei

<400> SEQUENCE: 49

```
atggctcttt gccagaacag gttacaggag gagcgcaagc aatggcgacg tgaccacccg        60
ttcggattct tgccaaaacc gtcccggaca aggagggcg tgctcgacct gaagaactgg       120
gaatgcggaa ttccgggcaa ggaaaagacg atctgggagg gagggttgtt caagctcaac       180
attgcgtttc ccgacgagta cccaacaaag ccgccgaaat gcaaatttgt ccctccgctg       240
ttccatccca cgtctacccc tcgggcaccg tctgcctgt cgattctcaa cgaggaagag       300
gcctggaagc cggccatcac ggtcaagcag attcttctgg gcatccaaga cctgctcaac       360
gaccccaacc ccgagtcgcc cgcccaagcc gacgcctaca atctgttcaa gaaagacaag       420
atcgagtacg aaaagcgcat ccggcgcgta gttcgcgaga atccggcgcc gtaa             474
```

<210> SEQ ID NO 50

```
<211> LENGTH: 157
<212> TYPE: PRT
<213> ORGANISM: Trichoderma reesei

<400> SEQUENCE: 50

Met Ala Leu Cys Gln Asn Arg Leu Gln Glu Glu Arg Lys Gln Trp Arg
1               5                   10                  15

Arg Asp His Pro Phe Gly Phe Ala Lys Pro Ser Arg Thr Lys Glu
            20                  25                  30

Gly Val Leu Asp Leu Lys Asn Trp Glu Cys Gly Ile Pro Gly Lys Glu
        35                  40                  45

Lys Thr Ile Trp Glu Gly Gly Leu Phe Lys Leu Asn Ile Ala Phe Pro
    50                  55                  60

Asp Glu Tyr Pro Thr Lys Pro Pro Lys Cys Lys Phe Val Pro Pro Leu
65                  70                  75                  80

Phe His Pro Asn Val Tyr Pro Ser Gly Thr Val Cys Leu Ser Ile Leu
                85                  90                  95

Asn Glu Glu Glu Ala Trp Lys Pro Ala Ile Thr Val Lys Gln Ile Leu
            100                 105                 110

Leu Gly Ile Gln Asp Leu Leu Asn Asp Pro Asn Pro Glu Ser Pro Ala
        115                 120                 125

Gln Ala Asp Ala Tyr Asn Leu Phe Lys Lys Asp Lys Ile Glu Tyr Glu
130                 135                 140

Lys Arg Ile Arg Arg Val Val Arg Glu Asn Pro Ala Pro
145                 150                 155

<210> SEQ ID NO 51
<211> LENGTH: 1820
<212> TYPE: DNA
<213> ORGANISM: Myceliophthora thermophila
<220> FEATURE:
<221> NAME/KEY: misc_feature
<222> LOCATION: (1720)..(1720)
<223> OTHER INFORMATION: n is a, c, g, or t

<400> SEQUENCE: 51
cctgcagtcc cttacctatg ggctcctagt ctcgttcctc tttttgatag atttgtattt      60
tgcaacgttg caaaatgaga catttcaatc atatgtagcc gccagctact gttagcgtac     120
tcagcgttgc ccaaacggcg ttttttctgg gtagcactgt gccgcgtgcc cctgagccgt     180
gcgtcgcgga aaccccctta agtagcaagt atgttaccgc cgagaccgac aatgctgttg     240
gttacctcgc tggtccatga ttgcaatcta gatatcgtgc ggggcttttg caatcggttt     300
tccctaccca ctttcttctt tggacacttt tctcttttgg aaaatgccga aatgatgcgg     360
ctcgctcacg ccccgaagtc ccgagctggg gctagatccg tgattgcaac gcggtgcgaa     420
cgcgactggg gcagacctcg ctcagccttg gtcgtgccgg aatggcgggt acctttacca     480
ggtcgggatc aattacatag gatgccatgt gcgtggattt gattgcatcg ctgtcccttt     540
tgtatgtgtc cgagagcgag acatcaacgc gaaaaccgga atgctcccaa cgtcgctctc     600
tgttcatagg gtcttttttt ttcttctgct ccatatcatc tgtcttgaac taagtgatca     660
tctgctgtca cgtcccgccc aatgattgta aagaatgata agtgatgctc gccggggcca     720
ggctctgtga agttccctc tttggttgac gatcaggtag cgccaacgtt gattgggccg     780
cccgtaaaat ccgaccctgt ctcctttcgt tgcaagtctc cgcgagaccg tgccaagcat     840
gttctccgga tccctcaatt acataaggtt tggctccagg gtaggtctgg aagctaccca     900
cctcggccaa gcaaccaatc acaaccagac ctcgcggcgt ttcgaccttc ctggtttgtc     960
```

```
tcagggctgg ccaacgtcct cccgtggcgg gtgcctggtg atcgcaggtc gcaggcgagt    1020
gccgggcacg cggagccccc gtcaaagctt gacccttca gagctaggtt tcattaggcc    1080
ttcgaaaaca acccaaggcc ccgtcgcaac catcacaacc ggccgataac cagatctcgg    1140
taggtccgat aaggatccaa aatggtgtcg gctgacgttg catgtgccca ggcaggagga    1200
tgatccccag ggttgttgcc ggcagctccc gcacgtcggg gaggggagg gggaggggaa     1260 agccctaact aacgttcgtt ctatcacggg ccgaccgggc catgctttcg gcttgtgagc    1320
ggtggggtca agggcaacaa gaaatgctaa gtgcgggacg aagacacgcg gcatgaggt    1380 ctcagggtga cctgcgcaaa accaagtccc actcgccatg cctccagcag caacgttgcc    1440
gtagaagggt caggggggttt gttgtagacc cacgaccatg ctgccggcga gcggagggtt    1500
ggcttgctac aggcgctgaa gggtcaactc ggtgcccaaa gtggctacca agcgtgccat    1560
caagggaaat gagatgatgg tggctcgtgg gcaaagaaaa gacaagggag gtgactctag    1620
agagatgctc tcgagttcac gggtataaga gcactgtgat cgttcacaaa gccggcgtac    1680
tcctctagag catctatcat caacatcacc agaaaggtcn tagaccaggt ggttgccata    1740
tccagtcgca aaagagccaa agagcgaagg agcacgaaag cacagcccaa tcattccctg    1800
ctttgctact tcttctccac                                                 1820

<210> SEQ ID NO 52
<211> LENGTH: 1776
<212> TYPE: DNA
<213> ORGANISM: Myceliophthora thermophila

<400> SEQUENCE: 52
ggtatccgat ttggggaacg tcgatgaaag tattgcaaaa gtgacgagag ttgcgcaact      60
aactcgctgc cgaagaagct gcggaagaaa gagaacaccg aaagtggaat aacgttacgg     120
atgtcctgac ctcaaagttg aaaccagccc ttcctgctct atttgggaaa gcggcttgcc     180
cttgaatgcg ctgcactgtg gcacgactac cagtgatcgg gaggagcaaa ctaccctggt     240
ccgttccttg gtggggcggc actaggccca acttagggtg atcggaggtc gatgccgcgg     300
tcctcgttgg tctgggctct tctcatttcc cggtttgcac ccccgttgc acctgctgat     360 cgcccgccaa cgccgatgag gttcgcccca gaccgacaat caccgcggct gcattcccaa     420
gtatattgaa gatggcacca ggtacccggt tttgcgtccc agtcgtttgg tgccaaattt     480
gggagttttt gagcctcaag atctgggaa atcgacctca acttccatac aagttaaagt      540
cgcacacacg gcgagttcca cgaagagaca cattttttc tgaaggcctc tctcccccgca    600 catcagaaac caccaaatac caagactgca gaagccgggg taagtgggcc accgggacta    660
cactaaaatg cggggagaag cgagatccgt tgcgaaggga agggatgggg tgtgctgcgg    720
cttctcccgc tctcgtgcgc cttttgcttg aatctagtgt acaccagggt aggctccgaa    780
ggagtatcta cggcagcgct gttcgtgctg cgttgagagt cagggcggag cgagcaggc    840 gacaggagcc tcgcaccggc acttcggatc gcatttgcgc ggagcgtcaa atacgctctt    900
ctgcggtcat cagagagcat cgtgaaccaa ggttcttccg cagggcggcc tgggcttcgc    960
agagtcgcac tcggcggacg ccttccgtgt caccctgat aacctggctg ccgcgcccag   1020
actcctccaa tgaggtgtgt ggttgccctc gccgacctt cagcaacctt aatcgcttcc     1080
atcgcacggc tccacgtcct cgaacgatgc cctcagtccg tgcccggccg tgcaaccat     1140 aacgtgacat cgccgcccag cctactagcc gctatcgacc ggttaggctt gtcaccgcag    1200
```

| | |
|---|---|
| cgcccattct ccatcgggcc tctactctga tccacctcac ccaccgcaag cactagcgag | 1260 |
| cctcaccaga gtgcaagcga cacgacccgc ttggcccttc gtccttgact atctcccaga | 1320 |
| cctcttgcca tcttgccgac gccgccccct tttttttctc ctcccctgc cggcaggtcg | 1380 |
| gtggccccag tcccgagatg gcattgctcc gttgtccatg acgacccatc attcgatggc | 1440 |
| tgactggcac actcgtcttg tttgagcatc gacggcccgc ggcccgtctc ccacggtacg | 1500 |
| gaacctcgtt gtacagtacc tctcgtaatg atacccaaca ccggggccga gcgctgggag | 1560 |
| ggcggcgttc ccgagaagcc gggaaggcgg ctggccggct gaccttttgtg acttggcgat | 1620 |
| ggatgcggcc atgagagaatg tccgtccgaa gcgacgcgac aattagcctg ctaccatcg | 1680 |
| atataaattg ggtgattccc agctcttgat gggcgtgtct tctgcctggc agccctcgtc | 1740 |
| ttcagatcaa gcaactgtgt gctgatcctc ttccgt | 1776 |

<210> SEQ ID NO 53
<211> LENGTH: 4164
<212> TYPE: DNA
<213> ORGANISM: artificial sequence
<220> FEATURE:
<223> OTHER INFORMATION: pCHI-phytase-tCBH

<400> SEQUENCE: 53

| | |
|---|---|
| gtcccttacc tatgggctcc tagtctcgtt cctcttttttg atagatttgt attttgcaac | 60 |
| gttgcaaaat gagacatttc aatcatatgt agccgccagc tactgttagc gtactcagcg | 120 |
| ttgcccaaac ggcggttttt ctgggtagca ctgtgccgcg tgcccctgag ccgtgcgtcg | 180 |
| cggaaacccc cttaagtagc aagtatgtta ccgccgagac cgacaatgct gttggttacc | 240 |
| tcgctggtcc atgattgcaa tctagatatc gtgcggggct tttgcaatcg gttttcccta | 300 |
| cccactttct tcttttggac actttctctt ttggaaaatg ccgaaatgat gcggctcgct | 360 |
| cacgccccga agtcccgagc tggggctaga tccgtgattg caacgcggtg cgaacgcgac | 420 |
| tggggcagac ctcgctcagc cttggtcgtg ccggaatggc gggtaccttt accaggtcgg | 480 |
| gatcaattac ataggatgcc atgtgcgtgg atttgattgc atcgctgtcc cttttgtatg | 540 |
| tgtccgagag cgagatatca acgcgaaaac cggaatgctc ccaacgtcgc tctctgttca | 600 |
| tagggtcttt tttttttcttc tgctccatat catctgtctt gaactaagtg atcatctgct | 660 |
| gtcacgtccc gcccaatgat tgtaaagaat gataagtgat gctcgccggg gccaggctct | 720 |
| gtgaaagttc cctctttggt tgacgatcag gtagcgccaa cgttgattgg gccgcccgta | 780 |
| aaatccgacc ctgtctccctt tcgttgcaag tctccgcgag accgtgccaa gcatgttctc | 840 |
| cggatccctc aattacataa ggtttggctc cagggtaggt ctggaagcta cccacctcgg | 900 |
| ccaagcaacc aatcacaacc agacctcgcg gcgtttcgac cttcctggtt tgtctcaggg | 960 |
| ctggccaacg tcctcccgtg gcgggtgcct ggtgatcgca ggtcgcaggc gagtgccggg | 1020 |
| cacgcggagc cccgtcaaa gcttgacccct ttcagagcta ggtttcatta ggccttcgaa | 1080 |
| aacaacccaa ggccccgtcg caaccatcac aaccggccga taaccagatc tcggtaggtc | 1140 |
| cgataaggat ccaaaatggt gtcggctgac gttgcatgtg cccaggcagg aggatgatcc | 1200 |
| ccaggggttgt tgccggcagc tcccgcacgt cggggagggg gagggggagg gaaagcccct | 1260 |
| aactaacgtt cgttctatca cgggccgacc gggccatgct ttcggcttgt gagcggtggg | 1320 |
| gtcaagggca acaagaaatg ctaagtgcgg gacgaagaca cgcgggcatg aggtctcagg | 1380 |
| gtgacctgcg caaaaccaag tcccactcgc catgcctcca gcagcaacgt tgccgtagaa | 1440 |
| gggtcagggg gtttgttgta gacccacgac catgctgccg gcgagcggag ggttggcttg | 1500 |

```
ctacaggcgc tgaagggtca actcggtgcc caaagtggct accaagcgtg ccatcaaggg    1560
aaatgagatg atggtggctc gtgggcaaag aaaagacaag ggaggtgact ctagagagat    1620
gctctcgagt tcacgggtat aagagcactg tgatcgttca caaagccggc gtactcctct    1680
agagcatcta tcatcaacat caccagaaag gtcaagacca ggtggttgcc atatccagtc    1740
gcaaaagagc caaagagcga aggagcacga aagcacagcc caatcattcc ctgctttgct    1800
acttcttctc caccatgcag accttcggtg ctttttctcgt ttccttcctc gccgccaggt    1860
aagttggcct tgatgaacca tatcatatat cgccgagaag tggaccgcgt gctgagactg    1920
agacagcggc ctggccgcgg ccaacgatac ccctgccagc ggctaccagg tcgagaaggt    1980
cgtcatcctc agccgccacg gcgtccgcgc ccctaccaag atgacccaga ccatgcgcga    2040
cgtcaccccc tacacctggc ccgagtggcc cgtcaagctc ggctacatca cccctcgcgg    2100
cgagcacctc atcagcctca tgggcggctt ctaccgccag aagttccagc agcagggcat    2160
cctccctcgc ggctcgtgcc ccacccccaa cagcatctac gtctggaccg acgtcgccca    2220 gcgcacctc aagaccggcg aggccttcct cgccggcctc gccccccagt gcggcctcac    2280
catccaccac cagcagaacc tcgagaaggc cgacccctc ttccacccg tcaaggccgg    2340 catctgcagc atggacaaga cccaggtcca gcaggccgtc gagaaggagg cccagacccc    2400
catcgacaac ctcaaccagc gctacatccc cgagctcgcc ctcatgaaca ccatcctcaa    2460
cttcagcaag agccctggt gccagaagca cagcgccgac aagccctgcg acctcgccct    2520
cagcatgccc agcaagctca gcatcaagga caacggcaac gaggtctccc tcgacggcgc    2580
tatcggcctc agctccaccc tcgccgagat cttcctcctc gagtacgccc agggcatgcc    2640
tcaggtcgcc tggggcaaca tccacagcga gcaggagtgg gccctcctcc tcaagctcca    2700
caacgtctac ttcgacctca tggagcgcac cccctacatc gcccgccaca agggcacccc    2760
cctcctccag gccatcagca acgccctcaa ccccaacgcc accgagagca agctccccga    2820
catcagcccc gacaacaaga tcctcttcat cgccggccac gacaccaaca tcgccaacat    2880
cgccggcatg ctcaacatgc gctggaccct cccccggccag cccgacaaca ccccccctgg    2940
cggcgctctc gtctttgagc gcctcgccga caagtccggc aagcagtacg tcagcgtcag    3000
catggtctac cagaccctcg agcagctccg cagccagacc cccctcagcc tcaaccagcc    3060
tcccggcagc gtccagctca agatccccgg ctgcaacgac cagaccgccg agggctactg    3120 cccccctcagc accttcaccc gcgtcgtcag ccagagcgtc gagcccggct gccagctcca    3180
gtaataaacg aacctctctg aaggaggttc tgagacacgc gcgattcttc tgtatatagt    3240 tttattttc actctggagt gcttcgctcc accagtacat aaaccttttt tttcacgtaa    3300
caaaatggct tcttttcaga ccatgtgaac catcttgatg ccttgacctc ttcagttctc    3360 acttttaacgt agttcgcgtt tgtctgtatg tcccagttgc atgtagttga gataaatacc    3420
cctggaagtg ggtctgggcc tttgtgggac ggagccctct ttctgtggtc tggagagccc    3480
gctctctacc gcctaccttc ttaccacagt acactactca cacattgctg aactgaccca    3540
tcataccgta ctttatcctg ttaattcgtg gtgctgtcga ctattctatt tgctcaaatg    3600
gagagcacat tcatcggcgc agggatacac ggtttatgga ccccaagagt gtaaggacta    3660
ttattagtaa tattatatgc ctctaggcgc cttaacttca acaggcgagc actactaatc    3720 aactttggt agacccaatt acaaacgacc atacgtgccg gaaatttttgg gattccgtcc    3780 gctctcccca accaagctag aagaggcaac gaacagccaa tcccggtgct aattaaatta    3840
```

-continued

| | |
|---|---|
| tatggttcca tttttttaaa aaaatttttt tcttcccatt ttcctctcgc ttttcttttt | 3900 |
| cgcatcgtag ttgatcaaag tccaagtcaa gcgagctatt tgtgctatag ctcggtggct | 3960 |
| ataatcagta cagcttagag aggctgtaaa ggtatgatac cacagcagta ttcgcgctat | 4020 |
| aagcggcact cctagactaa ttgttacggt ctacagaagt aggtaataaa agcgttaatt | 4080 |
| gttctaaata ctagaggcac ttagagaagc tatctaaata tatattgacc ctagcttatt | 4140 |
| atccctatta gtaagttagt tagc | 4164 |

```
<210> SEQ ID NO 54
<211> LENGTH: 4128
<212> TYPE: DNA
<213> ORGANISM: artificial sequence
<220> FEATURE:
<223> OTHER INFORMATION: pCBH-phytase-tCBH

<400> SEQUENCE: 54
```

| | |
|---|---|
| aggtatccga tttggggaac gtcgatgaaa gtattgcaaa agtgacgaga gttgcgcaac | 60 |
| taactcgctg ccgaagaagc tgcggaagaa agagaacacc gaaagtggaa taacgttacg | 120 |
| gatgtcctga cctcaaagtt gaaaccagcc cttcctgctc tatttgggaa agcggcttgc | 180 |
| ccttgaatgc gctgcactgt ggcacgacta ccagtgatcg ggaggagcaa actaccctgg | 240 |
| tccgttcctt ggtggggcgg cactaggccc aacttagggt gatcggaggt cgatgccgcg | 300 |
| gtcctcgttg gtctgggctc ttctcatttc ccggttgca cccccccgttg cacctgctga | 360 |
| tcgcccgcca acgccgatga ggttgcgccc agaccgacaa tcaccgcggc tgcattccca | 420 |
| agtatattga agatgcacc aggtacccgg ttttgcgtcc cagtcgtttg gtgccaaatt | 480 |
| tgggagtttt tgagcctcaa gatctgggga atcgacctc aacttccata caagttaaag | 540 |
| tcgcacacac ggcgagttcc acgaagagac acattttttt ctgaaggcct ctctccccgc | 600 |
| acatcagaaa ccaccaaata ccaagactgc agaagccggg gtaagtgggc caccgggact | 660 |
| acactaaaat gcggggagaa gcgagatccg ttgcgaaggg aagggatggg gtgtgctgcg | 720 |
| gctttctccg ctctcgtgcg cctttttgctt gaatctagtg tacaccaggg taggctccga | 780 |
| aggagtatct acggcagcgc tgttcgtgct gcgttgagag tcaggcgga gacgagcagg | 840 |
| cgacaggagc ctcgcaccgg cacttcggat cgcatttgcg cggagcgtca aatacgctct | 900 |
| tctgcggtca tcagagagca tcgtgaacca aggttcttcc gcagggcggc ctgggcttcg | 960 |
| cagagtcgca ctcggcggac gccttccgtg tcaccctga taacctggct gccgcgccca | 1020 |
| gactcctcca atgaggtgtg tggttgccct cgccgaccct tcagcaacct taatcgcttc | 1080 |
| catcgcacgg ctccacgtcc tcgaacgatg ccctcagtcc gtgcccggcc gtggcaacca | 1140 |
| taacgtgaca tcgccgccca gcctactagc cgctatcgac cggttaggct tgtcaccgca | 1200 |
| gcgcccattc tccatcgggc ctctactctg atccacctca cccaccgcaa gcactagcga | 1260 |
| gcctcaccag agtgcaagcg cacgacccg cttggccctt cgtccttgac tatctcccag | 1320 |
| acctcttgcc atcttgccga cgccgccccc ttttttttct cctcccctg ccggcaggtc | 1380 |
| ggtggcccca gtcccgagat ggcattgctc cgttgtccat gacgacccat cattcgatgg | 1440 |
| ctgactggca cactcgtctt gtttgagcat cgacggcccg cggcccgtct cccacggtac | 1500 |
| ggaacctcgt tgtacagtac ctctcgtaat gatacccaac accggggccg agcgctggga | 1560 |
| gggcggcgtt cccagagaagc cggaaggcg gctggccggc tgacctttgt gacttggcga | 1620 |
| tggatgcggc catggagaat gtccgtccga agcgacgcga caattagcct ggctaccatc | 1680 |
| gatataaatt gggtgattcc cagctcttga tgggcgtgtc ttctgcctgg cagccctcgt | 1740 |

```
cttcagatca agcaactgtg tgctgatcct cttccaccat gcagaccttc ggtgcttttc    1800
tcgtttcctt cctcgccgcc aggtaagttg gccttgatga accatatcat atatcgccga    1860
gaagtggacc gcgtgctgag actgagacag cggcctggcc gcggccaacg ataccnctgc    1920
cagcggctac caggtcgaga aggtcgtcat cctcagccgc cacggcgtcc gcgccctac     1980 caagatgacc cagaccatgc gcgacgtcac cccctacacc tggcccgagt ggcccgtcaa    2040
gctcggctac atcacccctc gcggcgagca cctcatcagc ctcatgggcg gcttctaccg    2100
ccagaagttc cagcagcagg gcatcctccc tcgcggctcg tgccccaccc ccaacagcat    2160
ctacgtctgg accgacgtcg cccagcgcac cctcaagacc ggcgaggcct tcctcgccgg    2220
cctcgccccc cagtgcggcc tcaccatcca ccaccagcag aacctcgaga aggccgaccc    2280
cctcttccac cccgtcaagg ccggcatctg cagcatggac aagacccagg tccagcaggc    2340
cgtcgagaag gaggcccaga cccccatcga caacctcaac cagcgctaca tccccgagct    2400
cgccctcatg aacaccatcc tcaacttcag caagagcccc tggtgccaga agcacagcgc    2460
cgacaagccc tgcgacctcg ccctcagcat gcccagcaag ctcagcatca aggacaacgg    2520
caacgaggtc tccctcgacg gcgctatcgg cctcagctcc accctcgccg agatcttcct    2580
cctcgagtac gcccagggca tgcctcaggt cgcctgggc aacatccaca gcgagcagga    2640
gtgggccctc ctcctcaagc tccacaacgt ctacttcgac ctcatggagc gcacccccta    2700
catcgcccgc cacaagggca ccccctcct ccaggccatc agcaacgccc tcaaccccaa    2760
cgccaccgag agcaagctcc ccgacatcag ccccgacaac aagatcctct tcatcgccgg    2820
ccacgacacc aacatcgcca acatcgccgg catgctcaac atgcgctgga ccctcccgg     2880 ccagcccgac aacaccccc ctggcggcgc tctcgtcttt gagcgcctcg ccgacaagtc     2940
cggcaagcag tacgtcagcg tcagcatggt ctaccagacc ctcgagcagc tccgcagcca    3000 gaccccctc agcctcaacc agcctcccgg cagcgtccag ctcaagatcc ccggctgcaa    3060
cgaccagacc gccgagggct actgcccccct cagcaccttc acccgcgtcg tcagccagag    3120
cgtcgagccc ggctgccagc tccagtaata acgaacctc tctgaaggag gttctgagac     3180
acgcgcgatt cttctgtata tagttttatt tttcactctg gagtgcttcg ctccaccagt    3240
acataaacct tttttttcac gtaacaaaat ggcttctttt cagaccatgt gaaccatctt    3300
gatgccttga cctcttcagt tctcactta acgtagttcg cgtttgtctg tatgtcccag    3360
ttgcatgtag ttgagataaa tacccctgga agtgggtctg ggcctttgtg ggacggagcc    3420
ctctttctgt ggtctggaga gcccgctctc taccgcctac cttcttacca cagtacacta    3480
ctcacacatt gctgaactga cccatcatac cgtactttat cctgttaatt cgtggtgctg    3540
tcgactattc tatttgctca aatggagagc acattcatcg gcgcagggat acacggttta    3600
tggaccccaa gagtgtaagg actattatta gtaatattat atgcctctag gcgccttaac    3660
ttcaacaggc gagcactact aatcaacttt tggtagaccc aattacaaac gaccatacgt    3720
gccggaaatt ttgggattcc gtccgctctc cccaaccaag ctagaagagg caacgaacag    3780
ccaatcccgg tgctaattaa attatatggt tccattttt taaaaaaatt ttttcttcc     3840 catttttcctc tcgcttttct ttttcgcatc gtagttgatc aaagtccaag tcaagcgagc    3900
tatttgtgct atagctcggt ggctataatc agtacagctt agagaggctg taaaggtatg    3960
```

```
ataccacagc agtattcgcg ctataagcgg cactcctaga ctaattgtta cggtctacag    4020
aagtaggtaa taaaagcgtt aattgttcta aatactagag gcacttagag aagctatcta    4080
aatatatatt gaccctagct tattatccct attagtaagt tagttagc                 4128
```